United States Patent
Yarden et al.

(10) Patent No.: US 10,526,416 B2
(45) Date of Patent: Jan. 7, 2020

(54) ANTI-HER3 ANTIBODIES AND USES OF SAME

(71) Applicant: Yeda Research and Development Co. Ltd., Rehovot (IL)

(72) Inventors: Yosef Yarden, Rehovot (IL); Nadège Gaborit, Rehovot (IL); Moshit Lindzen, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 164 days.

(21) Appl. No.: 15/508,112

(22) PCT Filed: Sep. 8, 2015

(86) PCT No.: PCT/IL2015/050915
§ 371 (c)(1),
(2) Date: Mar. 2, 2017

(87) PCT Pub. No.: WO2016/038609
PCT Pub. Date: Mar. 17, 2016

(65) Prior Publication Data
US 2017/0306049 A1      Oct. 26, 2017

Related U.S. Application Data

(60) Provisional application No. 62/047,168, filed on Sep. 8, 2014.

(51) Int. Cl.
*C07K 16/00* (2006.01)
*A61K 39/395* (2006.01)
*C07K 16/32* (2006.01)
*A61K 47/68* (2017.01)
*C07K 16/30* (2006.01)
*G01N 33/574* (2006.01)
*A61K 39/00* (2006.01)
*C07K 16/28* (2006.01)

(52) U.S. Cl.
CPC .......... *C07K 16/32* (2013.01); *A61K 47/6871* (2017.08); *C07K 16/30* (2013.01); *G01N 33/5748* (2013.01); *A61K 2039/505* (2013.01); *A61K 2039/507* (2013.01); *C07K 16/2863* (2013.01); *C07K 2317/24* (2013.01); *C07K 2317/565* (2013.01); *C07K 2317/73* (2013.01); *C07K 2317/732* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 7,498,142 B2 | 3/2009 | Yarden et al. |
| 2010/0016296 A1 | 1/2010 | Singh et al. |
| 2013/0195870 A1 | 8/2013 | Jaiswal et al. |
| 2016/0152712 A1 | 6/2016 | Yarden et al. |

FOREIGN PATENT DOCUMENTS

| EP | 2727943 | 5/2014 |
| WO | WO 2011/022727 | 2/2011 |
| WO | WO 2011/060206 | 5/2011 |
| WO | WO 2011/136911 | 11/2011 |
| WO | WO 2011/144749 | 11/2011 |
| WO | WO 2012/031198 | 3/2012 |
| WO | WO 2012/059224 | 5/2012 |
| WO | WO 2012/059857 | 5/2012 |
| WO | WO 2012/059858 | 5/2012 |
| WO | WO 2012/125864 | 9/2012 |
| WO | WO 2012/156532 | 11/2012 |
| WO | WO 2012/156975 | 11/2012 |
| WO | WO 2013/048883 | 4/2013 |
| WO | WO 2013/164689 | 11/2013 |
| WO | WO 2016/038609 | 3/2016 |
| WO | WO 2016/038610 | 3/2016 |

OTHER PUBLICATIONS

Communication Pursuant to Article 94(3) EPC dated Feb. 16, 2018 From the European Patent Office Re. Application No. 15781155.5. (8 Pages).
Communication Relating to the Results of the Partial International Search dated Dec. 21, 2015 From the International Searching Authority Re. Application No. PCT/IL2015/050916.
International Preliminary Report on Patentability dated Mar. 23, 2017 From the International Bureau of WIPO Re. Application No. PCT/IL2015/050915. (13 Pages).
International Preliminary Report on Patentability dated Mar. 23, 2017 From the International Bureau of WIPO Re. Application No. PCT/IL2015/050916. (15 Pages).
International Search Report and the Written Opinion dated Jan. 18, 2016 From the International Searching Authority Re. Application No. PCT/IL2015/050915.
International Search Report and the Written Opinion dated Feb. 26, 2016 From the International Searching Authority Re. Application No. PCT/IL2015/050916.
Official Action dated Mar. 30, 2017 From the U.S. Patent and Trademark Office Re. U.S. Appl. No. 14/956,585. (32 pages).

(Continued)

*Primary Examiner* — Mark Halvorson

(57) ABSTRACT

An isolated polypeptide is provided. The isolated polypeptide comprising an antigen recognition domain specifically binding human HER-3 with a $K_D$ value of 10 nM or lower, wherein the polypeptide inhibits neuregulin (NRG) binding to the human HER3 and NRG-induced cancer cell migration and proliferation. Additionally clones NG83 and NG140 are provided which bind human HER-3 with a $K_D$ value of 10 nM or lower.

11 Claims, 21 Drawing Sheets
(10 of 21 Drawing Sheet(s) Filed in Color)
Specification includes a Sequence Listing.

(56) References Cited

OTHER PUBLICATIONS

Bean et al. "MET Amplification Occurs With or Without T790M Mutations in EGFR Mutant Lung Tumors With Acquired Resistance to Gefinitib or Erlotinib", Proc. Natl. Acad. Sci. USA, PNAS, 104(52): 20932-20937, Dec. 26, 2007.
Beckman et al. "Antibody Constructs in Cancer Therapy", Cancer 109(2):170-179, Jan. 15, 2007.
Cespdes et al. "Mouse Models in Oncogenesis and Cancer Therapy", Clinical and Translational Oncology, 8(5):318-329, May 1, 2006.
Chen et al. "An Immunological Approach Reveals Biological Differences Between the Two NDF/Heregulin Receptors, ErbB-3 ad ErbB-4", The Journal of Biological Chemistry, 271(13):7620-2629, Mar. 29, 1996.
Citri et al. "EGF-ERBB Singalling: Towards the Systems Level", Nature Reviews Molecular Cell Biology, 7: 505-516, Jul. 2006.
Clinical Trials "Retrospective Analysis of the Expression of the Neurotensin Receptor by Metastatic Lung Adenocarcinomas (NTS)", Retrive from Clinical Trials, 3 Pages, Aug. 24, 2016.
Dennis "Off by a Whisker", Nature 442 (7104): 739-741, Aug. 17, 2006.
Engelman et al. "MET Amplification Leads to Gefinitib Resistance in Lung Cancer by Activating ERBB3 Signaling", Science, 316: 1039-1043, May 18, 2007.
Fujimori et al. "A Modeling Analysis of Monoclonal Antibody Percolation Through Tumors: A Binding-Site Barrier", Journal of Nuclear Medicine, 31(7): 1191-1198, Jul. 1990.
Gaborit et al. "Emerging Anti-Cancer Antibodies and Combination Therapies Targeting HER3/ERBB3", Human Vaccines and Immunotherapeutics, 12(3): 576-592, Mar. 3, 2016.
Gaborit et al. "Examination of HER3 Targeting in Cancer Using Monoclonal Antibodies", Proc. Nat. Acad. Sci. USA, PNAS, 112(3): 839-844, Jan. 20, 2015.
Hirsch et al. "Epidermal Growth Factor Receptor Inhibition in Lung Cancer. Status 2012", Journal of Thoracic Oncology, 8(3):373-384, Mar. 2013.
Huang et al. "Dual Targeting of EGFR and HER3 With MEHD7945A Overcomes Acquired Resistance to EGFR Inhibitors and Radiation", Cancer Research, XP055101487, 73(2): 824-833, Published Online Nov. 20, 2012. Abstract, Discussion.
Huang et al. "Recombinant Immunotherapeutics: Current State and Perspectives Regarding the Feasibility and Market",Applied Microbiology and Biotechnology, 87(2): 401-410, Jun. 1, 2010.
Jiang et al. "Advances in Targeting HER3 as an Anticancer Therapy", Chemotherapy Research and Practice, 2012(Art.817304): 1-9, 2012.
Kruser et al. "Mechanisms of Resistance to HER Family Targeting Antibodies", Experimental Cell Research, XP009155414, 316(2010): 1083-1100, Published Online Jan. 11, 2010. p. 1093, r-h Col, Para 2.
Lazrek et al. "Anti-HER3 Domain 1 and 3 Antibodies Reduce Tumor Growth by Hindering HER2/HER3 Dimerization and AKT-Induced MDM2, XIAP, and Fox01 Phosphorylation", Neoplasia, XP002727137, 15(3): 335-347, Mar. 2013. Abstract, P. 343, r-h Col, Para 3, Fig 5.
Ma et al. "Targeting of ErbB3 Receptor to Overcome Resistance in Cancer Treatment", Molecular Cancer, 13(105): 1-9, 2014.
Mancini et al. "Combining Three Antibodies Nullifies Feedback—Mediated Resistance to Erlotinib in Lung Cancer", Cancer, 8(379): ra53, 1-11, Jun. 2, 2015.
Mok et al. "Gefitinib or Carboplatin-Paclitaxel in Pulmonary Adenocarcinoma", The New England Journal of Medicine, 361(10): 947-957, Sep. 3, 2009.

Ohashi et al. "Epidermal Growth Factor Receptor Tyrosine Kinase Inhibitor-Resistant Disease", Journal of Clinical Oncology, 31(8): 1070-1080, Mar. 10, 2013.
Pirker et al. "Cetuximab Plus Chemotherapy in Patients With Advanced Non-Small-Cell Lung Cancer (FLEX): An Open-Label Randomised Phase III Trial", The Lancet, 373: 1525-1531, May 2, 2009.
Rexer et al. "Human Breast Cancer Cells Harboring a Gatekeeper T798M Mutation in HER2 Overexpress EGFR Ligands and Are Sensitive to Dual Inhibition of EGFR and HER2", Clinical Cancer Research, XP002751926, 19(19):5390-5401, Published Online Aug. 15, 2013. Abstract, Fig 51.
Rosell et al. "Screening for Epidermal Growth Factor Receptor Mutations in Lung Cancer", The New England Journal of Medicine, 361(10): 958-967, Sep. 3, 2009.
Rudnick et al. "Affinity and Avidity in Antibody-Based Tumor Targeting", Cancer Biotherapy and Radiopharmaceuticals, 24(2): 155-162, Apr. 1, 2009.
Sarup et al. "Human Epidermal Growth Factor Receptor (HER-1:HER-3) Fc- Mediated Heterodimer Has Broad Antiproliferative Activity In Vitro and in Human Tumor Xenografts", Molecular Cancer Therapeutics, 7(10): 3223-3236, Oct. 2008.
Schoeberl et al "An ErbB3 Antibody, MM-1231, Is Active in Cancers With Ligand-Dependent Activation", Cancer Research, XP002581703, 70(6): 2485-2494, Mar. 15, 2010. Abstract, Discussion, Last Para.
Sergina et al. "Escape From HER Family Tyrosine Kinse Inhibitor Therapy by the Kinase Inactive HER3", Nature, 445(7126): 437-441, Jan. 25, 2007.
Takezawa et al. "HER2 Amplification: A Potential Mechanism of Acquired Resistance to EGFR Inhibition in EGFR-Mutant Lung Cancers That Lack the Second-Site EGFR[T790M] Mutation", Cancer Discovery, 2(10): 922-933, Published OnlineFirst Sep. 5, 2012.
Talmadge et al. "Murine Models to Evaluate Novel and Conventional Therapeutic Strategies for Cancer", The American Journal of Pathology, 170(3): 793-804, Mar. 31, 2007.
Thurber et al. "Antibody Tumor Penetration: Transport Opposed by Systemic and Antigen-Mediated Clearance", Advanced Drug Delivery Reviews, 60(12): 1421-1434, Sep. 15, 2008.
Voskoglou-Nomikos et al. "Clinical Predictive Value of the in Vitro Cell Line, Human Xenograft, and Mouse Allograft Preclinical Cancer Models", Clinical Cancer Reseach, 9(11): 4227-4239, Sep. 15, 2003.
Wang et al. "Mechanisms of Resistance to ErbB-Targeted Cancer Therapeutics", The Journal of Clinical Investigation, 118(7): 2389-2392, Jul. 2008.
Wheeler et al. "Mechanisms of Acquired Resistance to Cetuximab: Role of HER (ErbB) Family Members", Oncogene, 27: 3944-3956, Published Online Feb. 25, 2008.
Yarden et al. "Cancer Immunotherapy: More Is (Much) Better", Clinical Cancer Research, 21(18): 4030-2, 9 Pages, 2015.
Official Action dated Sep. 27, 2017 From U.S. Appl. No. 14/956,585. (17 pages).
Communication Pursuant to Article 94(3) EPC Dated Jan. 11, 2019 From the European Patent Office Re. Application No. 16201602.6. (7 Pages).
Communication Pursuant to Article 94(3) EPC Dated Feb. 1, 2018 From the European Patent Office Re. Application No. 16201602.6. (7 Pages).
European Search Report and the European Search Opinion dated May 2, 2017 From the European Patent Office Re. Application No. 16201602.6. (9 Pages).

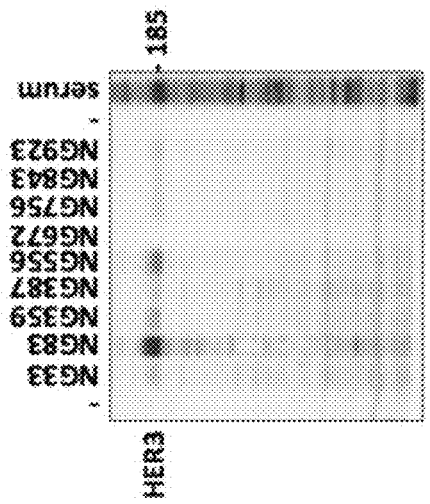
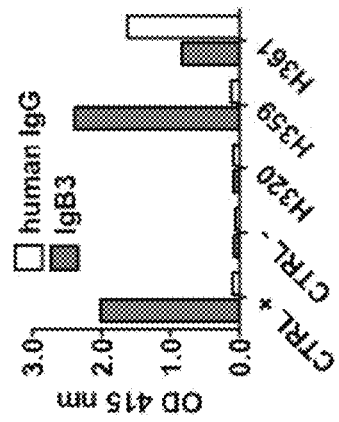
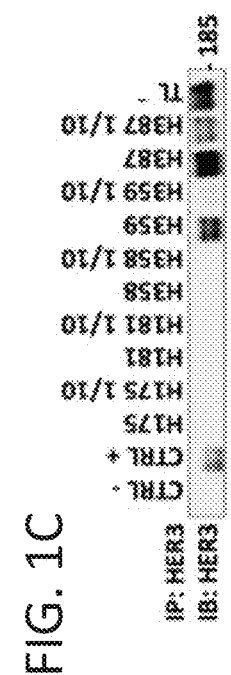
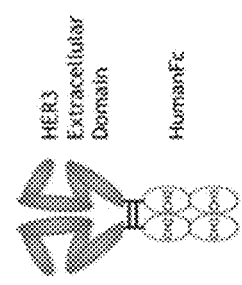
FIG. 1A  FIG. 1B  FIG. 1C  FIG. 1D  FIG. 1E

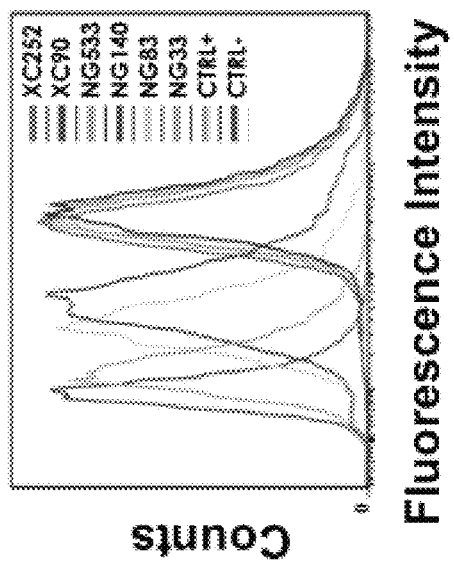
FIG. 2A
FIG. 2B
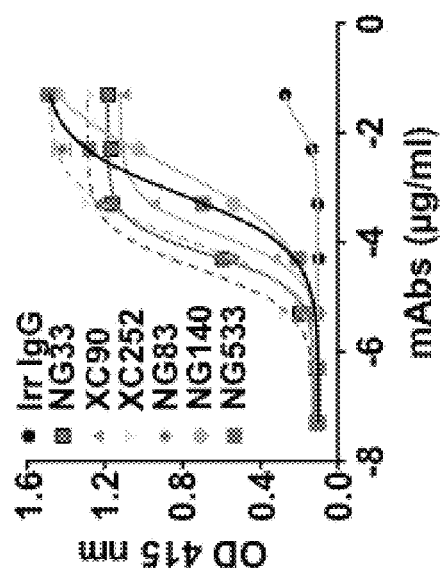
FIG. 2C
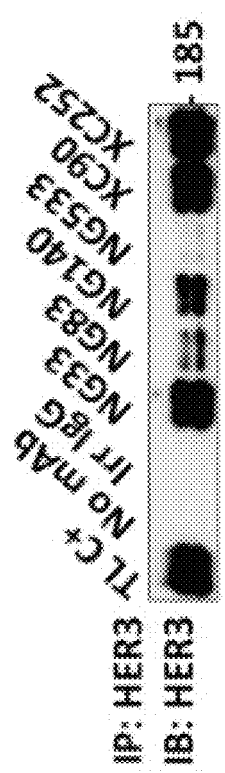
FIG. 2D

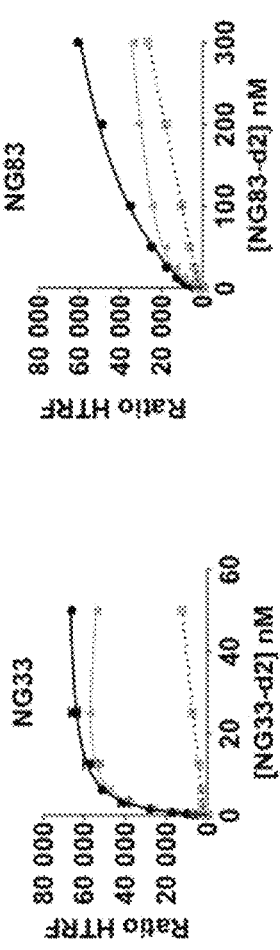
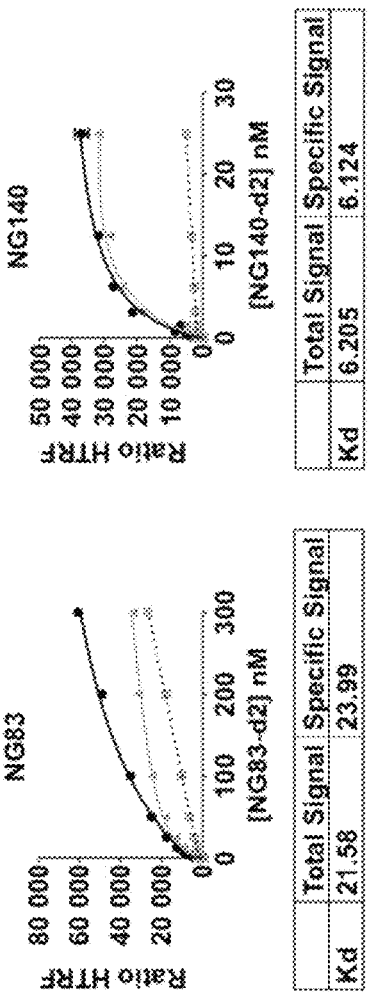
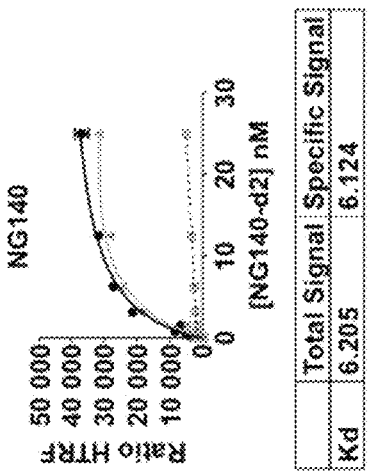
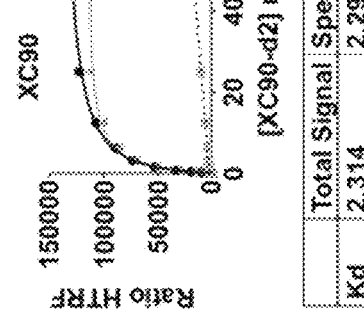
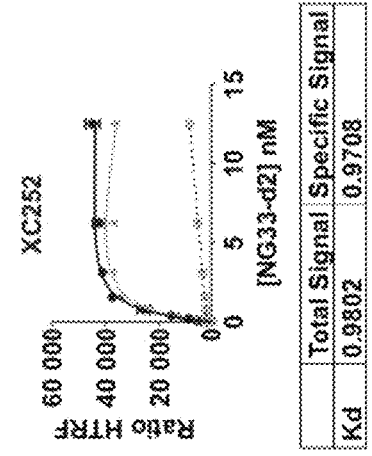
FIG. 3A  FIG. 3B  FIG. 3C
FIG. 3D  FIG. 3E

| mAbs | EGFR | | | HER2 | | | HER3 | | | EGFR/HER4 | | |
|---|---|---|---|---|---|---|---|---|---|---|---|---|
| CTRL+ | 3986 | +/- | 83 | 6869 | +/- | 51 | 2832 | +/- | 93 | 3349 | +/- | 129 |
| CTRL - | 170 | +/- | 59 | 205 | +/- | 38 | 147 | +/- | 55 | 245 | +/- | 89 |
| NG33 | 142 | +/- | 77 | 238 | +/- | 41 | 7365 | +/- | 85 | 249 | +/- | 88 |
| NG83 | 164 | +/- | 75 | 242 | +/- | 37 | 1524 | +/- | 79 | 326 | +/- | 96 |
| NG140 | 120 | +/- | 70 | 223 | +/- | 37 | 3980 | +/- | 87 | 184 | +/- | 92 |
| NG533 | 119 | +/- | 74 | 212 | +/- | 39 | 200 | +/- | 61 | 177 | +/- | 84 |
| XC90 | 122 | +/- | 61 | 193 | +/- | 37 | 8031 | +/- | 76 | 157 | +/- | 86 |
| XC252 | 128 | +/- | 77 | 220 | +/- | 40 | 6593 | +/- | 80 | 177 | +/- | 98 |

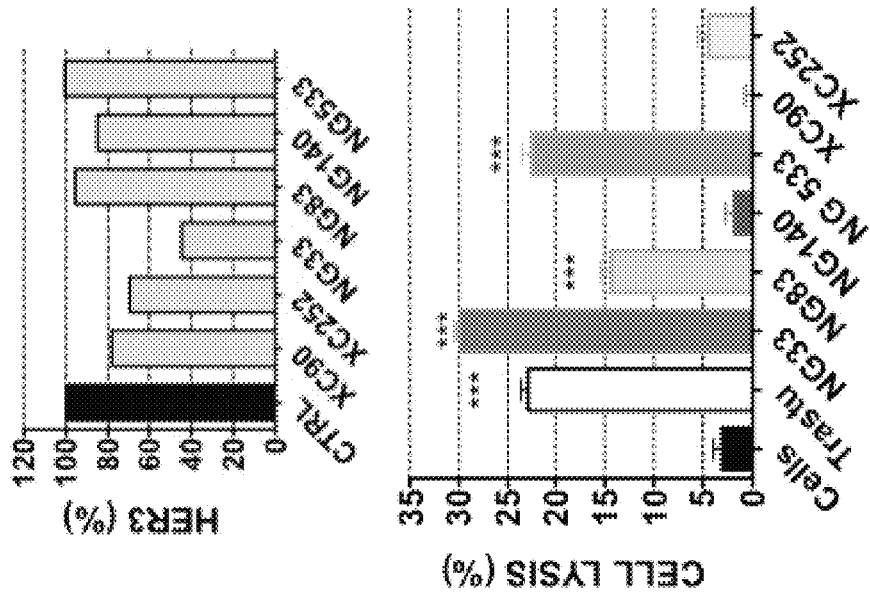
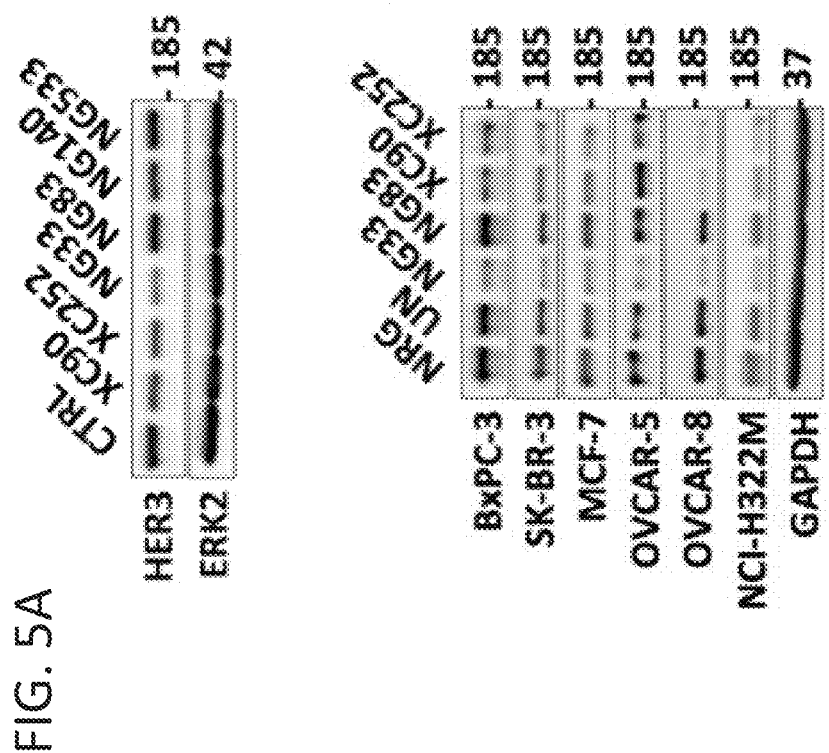
FIG. 5A  FIG. 5B  FIG. 5C  FIG. 5D

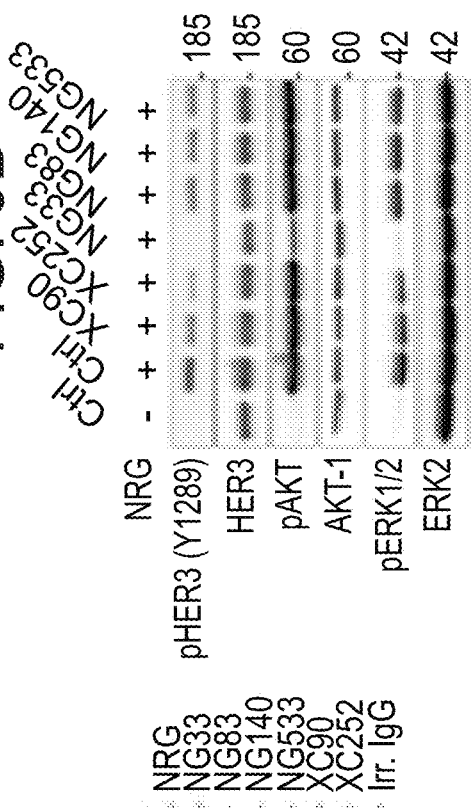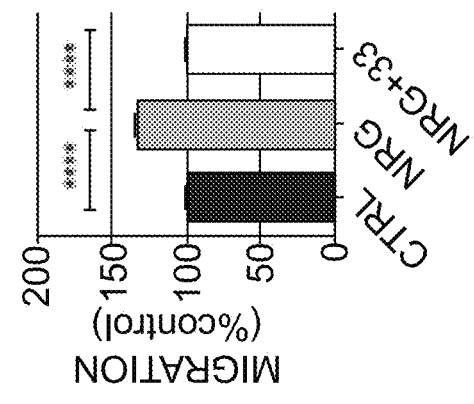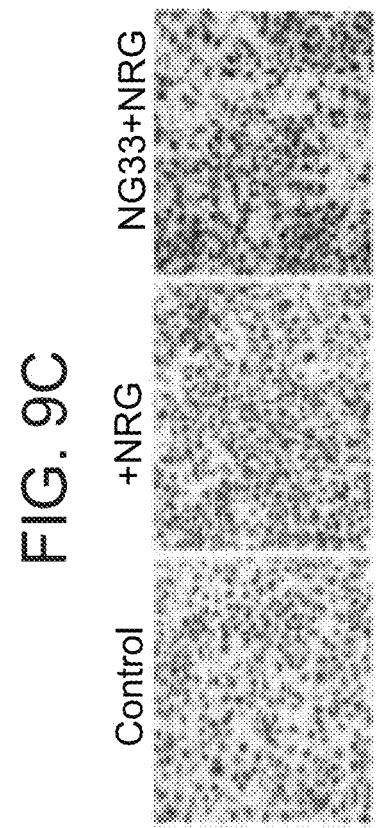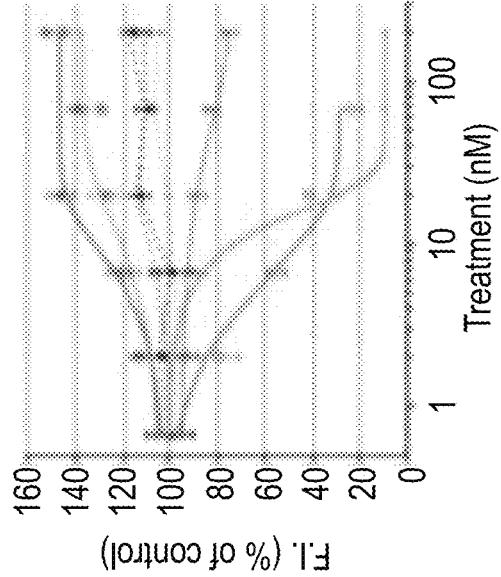
FIG. 9A
FIG. 9B
FIG. 9C

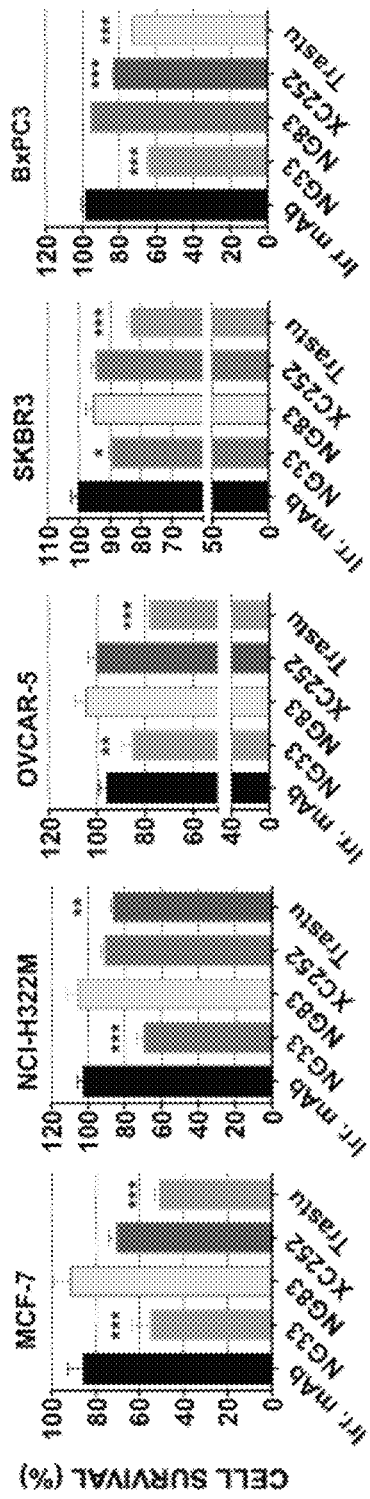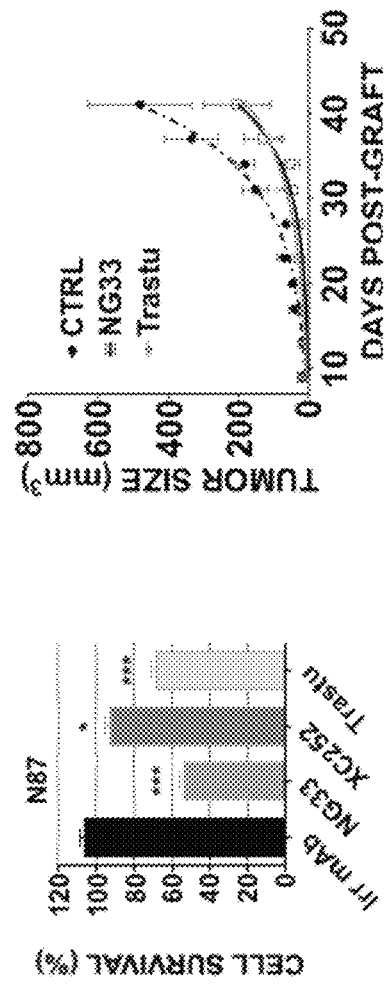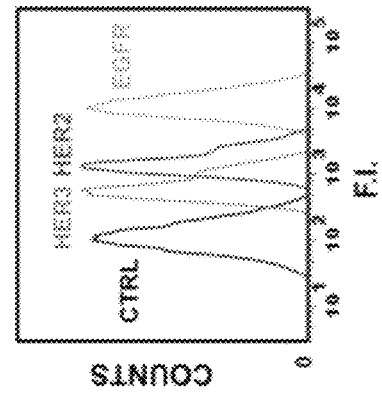
FIG. 10A
FIG. 10B
FIG. 10C
FIG. 10D

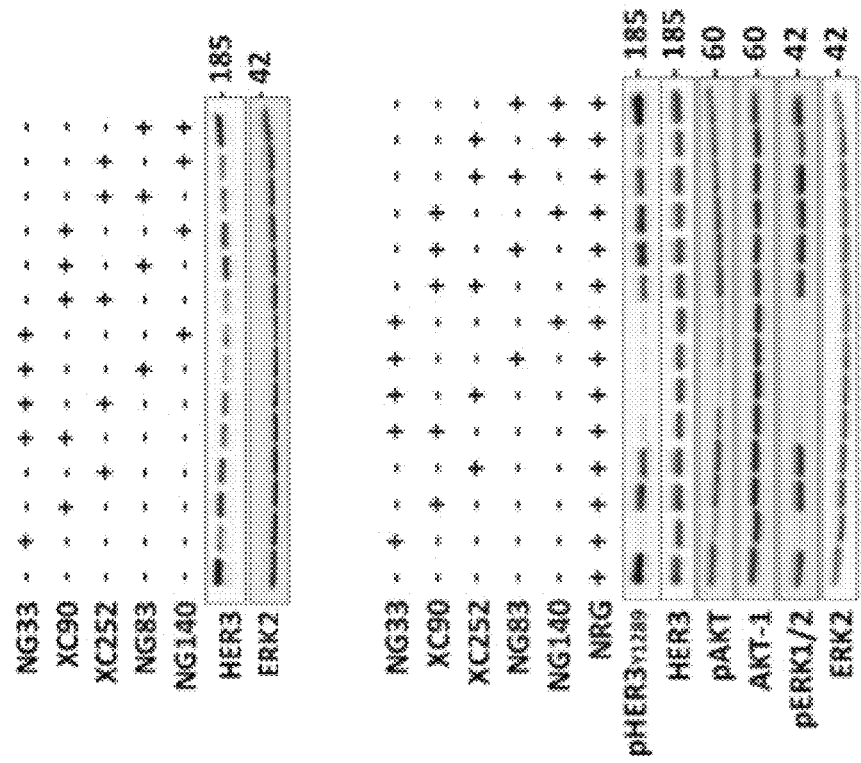
FIG. 12C
FIG. 12D
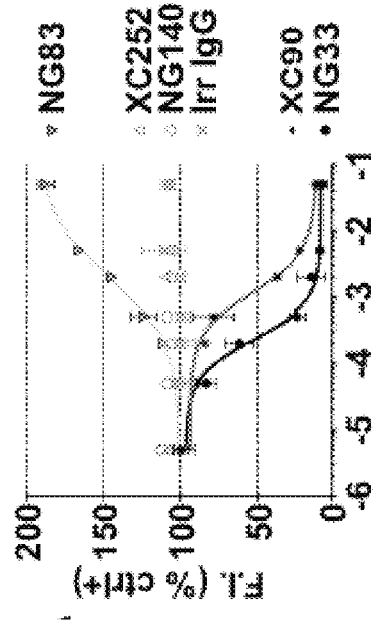
FIG. 12A
FIG. 12B

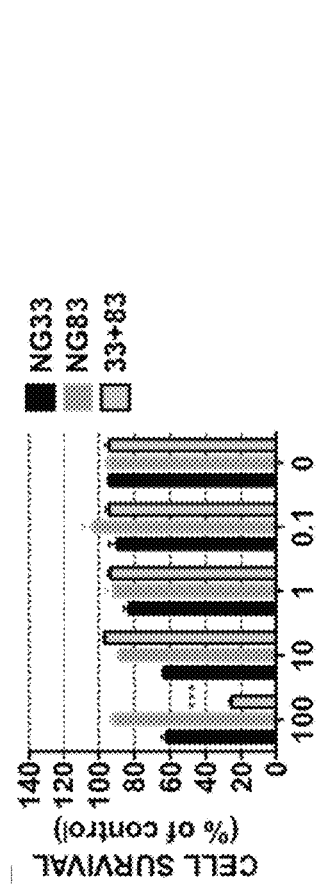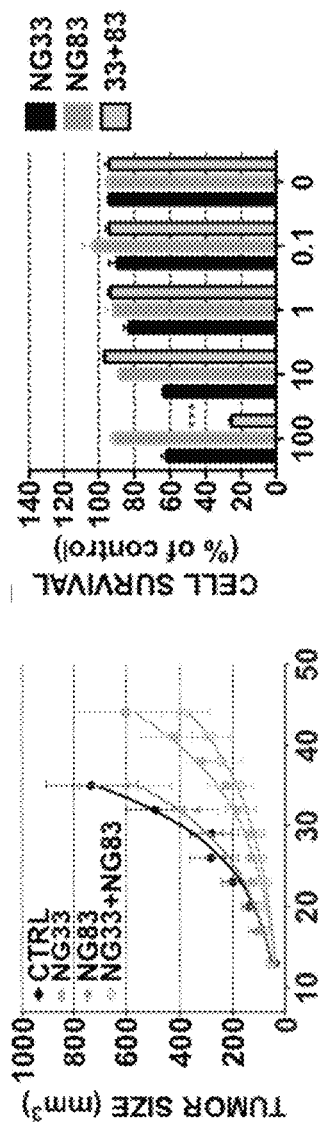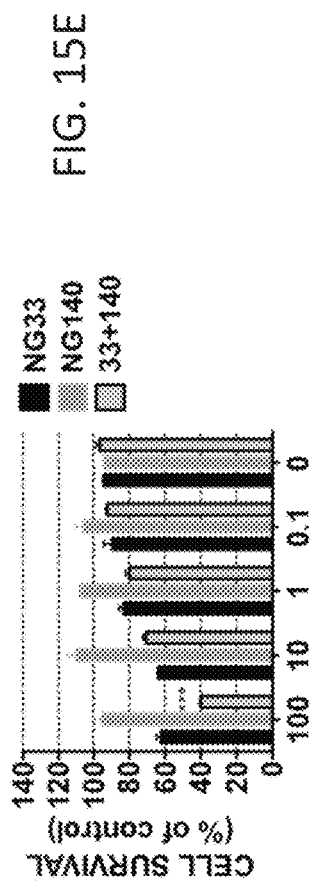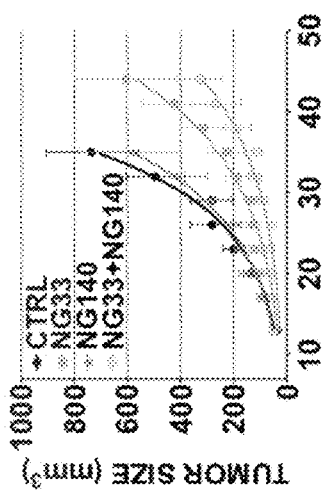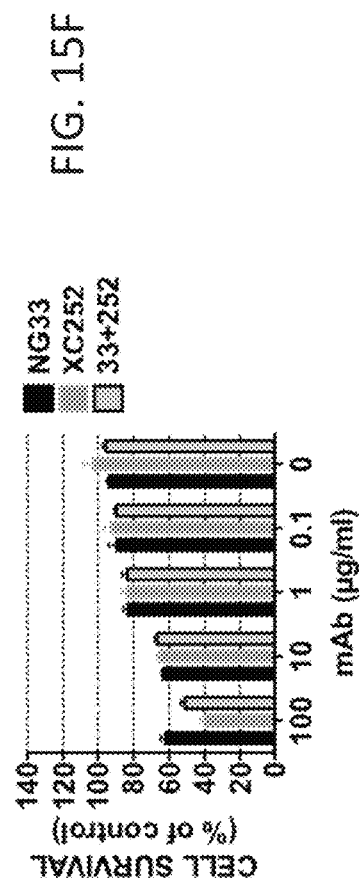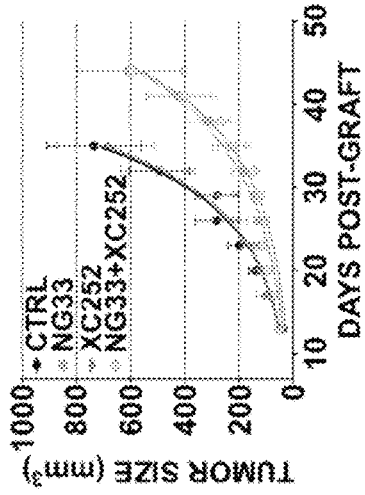

NG33 - VH (SEQ ID NO: 19):
NG33 - VK (SEQ ID NO: 20):

NG83 - VH (SEQ ID NO: 29):
NG83 - VK (SEQ ID NO: 30):

XC252 - VH (SEQ ID NO: 49)

XC252 - VK (SEQ ID NO: 53)

SEQUENCE LISTING

<160> NUMBER OF SEQ ID NOS: 56

<210> SEQ ID NO 1

```
<211> LENGTH: 9
<212> TYPE: PRT
<213> ORGANISM: Artificial sequence
<220> FEATURE:
<223> OTHER INFORMATION: CDR Amino Acid sequence

<400> SEQUENCE: 1

Gly Tyr Ser Ile Thr Ser Gly Phe Tyr
1               5

<210> SEQ ID NO 2
<211> LENGTH: 7
<212> TYPE: PRT
<213> ORGANISM: Artificial sequence
<220> FEATURE:
<223> OTHER INFORMATION: CDR Amino Acid sequence

<400> SEQUENCE: 2

Ile Ala Tyr Asp Gly Thr Ser
1               5

<210> SEQ ID NO 3
<211> LENGTH: 13
<212> TYPE: PRT
<213> ORGANISM: Artificial sequence
<220> FEATURE:
<223> OTHER INFORMATION: CDR Amino Acid sequence

<400> SEQUENCE: 3

Ala Arg Gly Gly Gly Tyr Tyr Gly Gln Leu Leu Asp Tyr
1               5                   10

<210> SEQ ID NO 4
<211> LENGTH: 6
<212> TYPE: PRT
<213> ORGANISM: Artificial sequence
<220> FEATURE:
<223> OTHER INFORMATION: CDR Amino Acid sequence

<400> SEQUENCE: 4

Gln Asp Ile Ser Asn Tyr
1               5

<210> SEQ ID NO 5
<211> LENGTH: 3
<212> TYPE: PRT
<213> ORGANISM: Artificial sequence
<220> FEATURE:
<223> OTHER INFORMATION: CDR Amino Acid sequence

<400> SEQUENCE: 5

Asn Thr Ala
1

<210> SEQ ID NO 6
<211> LENGTH: 9
<212> TYPE: PRT
<213> ORGANISM: Artificial sequence
<220> FEATURE:
<223> OTHER INFORMATION: CDR Amino Acid sequence

<400> SEQUENCE: 6

Gln Gln Gly Lys Thr Leu Pro Trp Thr
1               5

<210> SEQ ID NO 7
<211> LENGTH: 6
```

```
<212> TYPE: PRT
<213> ORGANISM: Artificial Sequence
<220> FEATURE:
<223> OTHER INFORMATION: CDR Amino Acid sequence

<400> SEQUENCE: 7

Gln Asp Ile Arg Asn Tyr
1               5

<210> SEQ ID NO 8
<211> LENGTH: 3
<212> TYPE: PRT
<213> ORGANISM: Artificial Sequence
<220> FEATURE:
<223> OTHER INFORMATION: CDR Amino Acid sequence

<400> SEQUENCE: 8

Tyr Thr Ser
1

<210> SEQ ID NO 9
<211> LENGTH: 9
<212> TYPE: PRT
<213> ORGANISM: Artificial Sequence
<220> FEATURE:
<223> OTHER INFORMATION: CDR Amino Acid sequence

<400> SEQUENCE: 9

Gln Gln Gly Asn Thr Leu Pro Trp Thr
1               5

<210> SEQ ID NO 10
<211> LENGTH: 8
<212> TYPE: PRT
<213> ORGANISM: Artificial Sequence
<220> FEATURE:
<223> OTHER INFORMATION: CDR Amino Acid sequence

<400> SEQUENCE: 10

Gly Tyr Thr Phe Thr Asn Tyr Gly
1               5

<210> SEQ ID NO 11
<211> LENGTH: 8
<212> TYPE: PRT
<213> ORGANISM: Artificial Sequence
<220> FEATURE:
<223> OTHER INFORMATION: CDR Amino Acid sequence

<400> SEQUENCE: 11

Ile Asn Thr Tyr Ala Gly Glu Pro
1               5

<210> SEQ ID NO 12
<211> LENGTH: 11
<212> TYPE: PRT
<213> ORGANISM: Artificial Sequence
<220> FEATURE:
<223> OTHER INFORMATION: CDR Amino Acid sequence

<400> SEQUENCE: 12

Ala Arg Gly Gly Ile Thr Gly Ala Met Asp Tyr
1               5                   10

<210> SEQ ID NO 13
<211> LENGTH: 6
<212> TYPE: PRT
```

<213> ORGANISM: Artificial Sequence
<220> FEATURE:
<223> OTHER INFORMATION: CDR Amino Acid sequence

<400> SEQUENCE: 13

Asp His Ile Asn Asn Trp
1               5

<210> SEQ ID NO 14
<211> LENGTH: 3
<212> TYPE: PRT
<213> ORGANISM: Artificial Sequence
<220> FEATURE:
<223> OTHER INFORMATION: CDR Amino Acid sequence

<400> SEQUENCE: 14

Gly Ala Thr
1

<210> SEQ ID NO 15
<211> LENGTH: 9
<212> TYPE: PRT
<213> ORGANISM: Artificial Sequence
<220> FEATURE:
<223> OTHER INFORMATION: CDR Amino Acid sequence

<400> SEQUENCE: 15

Gln Gln Tyr Trp Ser Ile Pro Trp Thr
1               5

<210> SEQ ID NO 16
<211> LENGTH: 9
<212> TYPE: PRT
<213> ORGANISM: Artificial Sequence
<220> FEATURE:
<223> OTHER INFORMATION: CDR Amino Acid sequence

<400> SEQUENCE: 16

Gly Tyr Ser Ile Thr Ser Gly Tyr Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: CDR Amino Acid sequence

<400> SEQUENCE: 17

Ile Tyr Tyr Asp Gly Ser Asn
1               5

<210> SEQ ID NO 18
<211> LENGTH: 12
<212> TYPE: PRT
<213> ORGANISM: Artificial Sequence
<220> FEATURE:
<223> OTHER INFORMATION: CDR Amino Acid sequence

<400> SEQUENCE: 18

Ala Arg Asp Tyr Asp Val Gly Tyr Ala Met Asp Tyr
1               5                   10

<210> SEQ ID NO 19
<211> LENGTH: 120
<212> TYPE: PRT
<213> ORGANISM: Artificial Sequence
<220> FEATURE:
<223> OTHER INFORMATION: VH chain of NG 33 polypeptide

<400> SEQUENCE: 19

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Ser Trp Ile Arg Gln Phe Pro Gly Asn Lys Leu Glu Trp
        35                  40                  45

Met Gly Tyr Ile Ala Tyr Asp Gly Thr Ser Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Lys Ser Val Thr Asn Glu Asp Thr Pro Thr Tyr Tyr Cys
                85                  90                  95

Ala Arg Gly Gly Gly Tyr Tyr Gly Gln Leu Leu Asp Tyr Trp Gly Gln
            100                 105                 110

Gly Thr Ser Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: VL chain of NG 33 polypeptide

<400> SEQUENCE: 20

Asp Ala Arg Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Asn Thr Ala Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Lys Thr Leu Pro Trp
                85                  90                  95

Thr Phe Gly Gly Gly Thr Lys Leu Glu Leu Lys
            100                 105

<210> SEQ ID NO 21
<211> LENGTH: 361
<212> TYPE: DNA
<213> ORGANISM: Artificial Sequence
<220> FEATURE:
<223> OTHER INFORMATION: nucleic acids sequence of heavy chain of Clone
      NG33

<400> SEQUENCE: 21
gatgtgcagc tgcaggagtc aggacctggc ctcgtgaaac cttctcagtc tctgtctctc      60
acctgctctg tcactggcta ctccatcacc agtggttttt actggagctg gatccggcag     120
tttccaggaa acaagttgga atggatgggc tatatagcct acgacggtac cagtaactac     180
aatccatctc tcaaaaatcg aatctccatc actcgtgaca catctaagaa tcagtttttc     240

```
ctgaagttga aatctgtgac taatgaggac acacctacat attactgtgc aagaggggggg    300 ggctactatg gtcagcttct ggactactgg ggtcaaggaa cctcagtcac cgtgtcctca    360
g                                                                     361
```

<210> SEQ ID NO 22
<211> LENGTH: 322
<212> TYPE: DNA
<213> ORGANISM: Artificial Sequence
<220> FEATURE:
<223> OTHER INFORMATION: nucleic acids sequence of light chain of Clone
      NG33

<400> SEQUENCE: 22

```
gatgcgcgca tgactcagtc tccatcctcc ctgtctgcct ctctgggaga cagagtcacc     60
atcagttgca gggcaagtca ggacattagc aattatttaa actggtatca gcagaaacca    120
gatggaactg ttaaagtcct gatctacaac acagcaaaat tacactcagg agtcccatca    180
aggttcagtg gcagtgggtc tggaacagat tattctctca ccattagtaa cctggagcaa    240
gaagattttg ccacttactt ttgccaacag ggtaaaacgc ttccgtggac gttcggtgga    300
ggcaccaagc tcgagctaaa ac                                             322
```

<210> SEQ ID NO 23
<211> LENGTH: 18
<212> TYPE: DNA
<213> ORGANISM: Artificial sequence
<220> FEATURE:
<223> OTHER INFORMATION: CDR Nucleic Acid sequence

<400> SEQUENCE: 23

```
caggacatta gcaattat                                                   18
```

<210> SEQ ID NO 24
<211> LENGTH: 9
<212> TYPE: DNA
<213> ORGANISM: Artificial sequence
<220> FEATURE:
<223> OTHER INFORMATION: CDR Nucleic Acid sequence

<400> SEQUENCE: 24

```
aacacagca                                                              9
```

<210> SEQ ID NO 25
<211> LENGTH: 27
<212> TYPE: DNA
<213> ORGANISM: Artificial sequence
<220> FEATURE:
<223> OTHER INFORMATION: CDR Nucleic Acid sequence

<400> SEQUENCE: 25

```
caacagggta aaacgcttcc gtggacg                                         27
```

<210> SEQ ID NO 26
<211> LENGTH: 27
<212> TYPE: DNA
<213> ORGANISM: Artificial sequence
<220> FEATURE:
<223> OTHER INFORMATION: CDR Nucleic Acid sequence

<400> SEQUENCE: 26

```
ggctactcca tcaccagtgg tttttac                                         27
```

<210> SEQ ID NO 27

<211> LENGTH: 21
<212> TYPE: DNA
<213> ORGANISM: Artificial sequence
<220> FEATURE:
<223> OTHER INFORMATION: CDR Nucleic Acid sequence

<400> SEQUENCE: 27
atagcctacg acggtaccag t                                              21

<210> SEQ ID NO 28
<211> LENGTH: 39
<212> TYPE: DNA
<213> ORGANISM: Artificial sequence
<220> FEATURE:
<223> OTHER INFORMATION: CDR Nucleic Acid sequence

<400> SEQUENCE: 28
gcaagagggg ggggctacta tggtcagctt ctggactac                           39

<210> SEQ ID NO 29
<211> LENGTH: 118
<212> TYPE: PRT
<213> ORGANISM: Artificial Sequence
<220> FEATURE:
<223> OTHER INFORMATION: VH chain of NG83 polypeptide

<400> SEQUENCE: 29

Gln Ile Gln Leu Val Gln Ser Gly Pro Glu Leu Lys Lys Arg Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Cys Met
        35                  40                  45

Gly Trp Ile Asn Thr Tyr Ala Gly Glu Pro Thr Tyr Ala Asp Asp Phe
    50                  55                  60

Lys Gly Arg Phe Ala Phe Ser Leu Asp Ser Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Gly Ile Thr Gly Ala Met Asp Tyr Trp Gly Gln Gly Thr
            100                 105                 110

Ser Val Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: VL chain of NG83 polypeptide

<400> SEQUENCE: 30

Asp Val Val Met Thr Gln Lys Thr Ser Ser Leu Ser Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asp Leu Glu Gln

```
            65                  70                  75                  80
        Glu Asp Ile Ala Thr Tyr Phe Cys Gln Gln Gly Asn Thr Leu Pro Trp
                        85                  90                  95

Thr Phe Gly Gly Gly Thr Lys Leu Ala Ile Lys
                        100                 105
```

<210> SEQ ID NO 31
<211> LENGTH: 355
<212> TYPE: DNA
<213> ORGANISM: Artificial Sequence
<220> FEATURE:
<223> OTHER INFORMATION: nucleic acids sequence of heavy chain of NG83

<400> SEQUENCE: 31

```
cagatccagt tggtgcagtc tggacctgaa ctgaagaaac gtggagagac agtcaagatc    60
tcctgcaagg cttctggata taccttcaca aactatggaa tgaactgggt gaggcaggct   120
cccggaaagg gtttaaagtg catgggctgg ataaacacct acgctggaga gccaacatat   180
gctgatgact tcaagggacg gtttgccttc tctttggatt cctctgccag cactgcctat   240
ttgcagatca caacctcaa aaatgaggac atggctacat atttctgtgc aagaggggg    300 attacggggg ctatggacta ctggggtcaa ggaacctcag tcaccgtctc ctcag        355
```

<210> SEQ ID NO 32
<211> LENGTH: 322
<212> TYPE: DNA
<213> ORGANISM: Artificial Sequence
<220> FEATURE:
<223> OTHER INFORMATION: nucleic acids sequence of light chain of NG83

<400> SEQUENCE: 32

```
gatgtagtta tgacacagaa aacatcctcc ctatctacct ctctgggaga cagagtcacc    60
atcagttgca gggcaagtca agacattcgc aattatttaa actggtatca gcagaaacca   120
gatggaactg ttaaactcct gatctactac acatcaagat acactcaggg gtcccatca    180 aggttcagtg gcagtgggtc tggaacagat tattctctca ccattagtga cctggagcaa   240
gaagatattg ccacttactt ttgccaacag ggtaatacgc ttccgtggac gttcggtgga   300
ggcaccaagc tggcaatcaa ac                                            322
```

<210> SEQ ID NO 33
<211> LENGTH: 24
<212> TYPE: DNA
<213> ORGANISM: Artificial Sequence
<220> FEATURE:
<223> OTHER INFORMATION: nucleic acid sequence encoding CDR of NG83

<400> SEQUENCE: 33

```
ggatatacct tcacaaacta tgga                                           24
```

<210> SEQ ID NO 34
<211> LENGTH: 24
<212> TYPE: DNA
<213> ORGANISM: Artificial Sequence
<220> FEATURE:
<223> OTHER INFORMATION: nucleic acid sequence encoding CDR of NG83

<400> SEQUENCE: 34

```
ataaacacct acgctggaga gcca                                           24
```

<210> SEQ ID NO 35
<211> LENGTH: 33

```
<212> TYPE: DNA
<213> ORGANISM: Artificial Sequence
<220> FEATURE:
<223> OTHER INFORMATION: nucleic acid sequence encoding CDR of NG83

<400> SEQUENCE: 35
gcaagagggg ggattacggg ggctatggac tac                                33

<210> SEQ ID NO 36
<211> LENGTH: 18
<212> TYPE: DNA
<213> ORGANISM: Artificial Sequence
<220> FEATURE:
<223> OTHER INFORMATION: nucleic acid sequence encoding CDR of NG83

<400> SEQUENCE: 36
caagacattc gcaattat                                                 18

<210> SEQ ID NO 37
<211> LENGTH: 9
<212> TYPE: DNA
<213> ORGANISM: Artificial Sequence
<220> FEATURE:
<223> OTHER INFORMATION: nucleic acid sequence encoding CDR of NG83

<400> SEQUENCE: 37 tacacatca                                                            9

<210> SEQ ID NO 38
<211> LENGTH: 27
<212> TYPE: DNA
<213> ORGANISM: Artificial Sequence
<220> FEATURE:
<223> OTHER INFORMATION: nucleic acid sequence encoding CDR of NG83

<400> SEQUENCE: 38
caacagggta atacgcttcc gtggacg                                       27

<210> SEQ ID NO 39
<211> LENGTH: 119
<212> TYPE: PRT
<213> ORGANISM: Artificial Sequence
<220> FEATURE:
<223> OTHER INFORMATION: VH chain of NG140 polypeptide

<400> SEQUENCE: 39

Gln Val Gln Leu Lys Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Ser Ile Tyr Tyr Asp Gly Ser Asn Asn Tyr Asn Pro Ser Leu
    50                  55                  60

Lys Asn Arg Ile Ser Val Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Asp Tyr Asp Val Gly Tyr Ala Met Asp Tyr Trp Gly Gln Gly
            100                 105                 110

Ala Ser Val Thr Val Ser Ser
        115
```

<210> SEQ ID NO 40
<211> LENGTH: 107
<212> TYPE: PRT
<213> ORGANISM: Artificial Sequence
<220> FEATURE:
<223> OTHER INFORMATION: VL chain of NG140 polypeptide

<400> SEQUENCE: 40

```
Asp Ile Val Leu Thr Gln Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ile Pro Trp
                85                  90                  95

Thr Phe Gly Gly Gly Thr Lys Leu Glu Ile Lys
            100                 105
```

<210> SEQ ID NO 41
<211> LENGTH: 358
<212> TYPE: DNA
<213> ORGANISM: Artificial Sequence
<220> FEATURE:
<223> OTHER INFORMATION: nucleic acids sequence of heavy chain of NG140

<400> SEQUENCE: 41

```
caggtgcagc ttaaggagtc aggacctggc ctcgtgaaac cttctcagtc tctgtctctc      60
acctgctctg tcactggcta ctccatcacc agtggttatt actggaactg gatccggcag     120
tttccaggaa acaaactgga atggatgggc tccatatatt acgacggtag caataactac     180
aacccatctc tcaaaaatcg aatctccgtc actcgtgaca catctaagaa ccagttttc      240 ctgaagttga attctgtgac tactgaggac acagctacat tactgtgc aagagattat       300 gacgtagggt atgctatgga ctactggggt caaggagcct cagtcaccgt ctcctcag       358
```

<210> SEQ ID NO 42
<211> LENGTH: 322
<212> TYPE: DNA
<213> ORGANISM: Artificial Sequence
<220> FEATURE:
<223> OTHER INFORMATION: nucleic acids sequence of light chain of NG140

<400> SEQUENCE: 42

```
gacatcgtgc tgacacaatc ttcatcctac ttgtctgtat ctctaggagg cagagtcacc      60
attacttgca aggcaagtga ccacattaat aattggttag cctggtatca gcagaaacca     120
ggaaatgctc ctaggctctt aatatctggt gcaaccagtt tggaaactgg ggttccttca     180
agattcagtg gcagtggatc tggaaaggac tacactctca gcattaccag tcttcagact     240
gaagatgttg ctacttatta ctgtcaacag tattggagta ttccgtggac gttcggtgga     300
ggcaccaagc tagaaatcaa ac                                              322
```

<210> SEQ ID NO 43
<211> LENGTH: 27
<212> TYPE: DNA

```
<213> ORGANISM: Artificial Sequence
<220> FEATURE:
<223> OTHER INFORMATION: nucleic acid sequence encoding CDR of NG140

<400> SEQUENCE: 43
ggctactcca tcaccagtgg ttattac                                      27

<210> SEQ ID NO 44
<211> LENGTH: 21
<212> TYPE: DNA
<213> ORGANISM: Artificial Sequence
<220> FEATURE:
<223> OTHER INFORMATION: Artificial Sequence

<400> SEQUENCE: 44
atatattacg acggtagcaa t                                            21

<210> SEQ ID NO 45
<211> LENGTH: 36
<212> TYPE: DNA
<213> ORGANISM: Artificial Sequence
<220> FEATURE:
<223> OTHER INFORMATION: nucleic acid sequence encoding CDR of NG140

<400> SEQUENCE: 45
gcaagagatt atgacgtagg gtatgctatg gactac                            36

<210> SEQ ID NO 46
<211> LENGTH: 18
<212> TYPE: DNA
<213> ORGANISM: Artificial Sequence
<220> FEATURE:
<223> OTHER INFORMATION: Artificial Sequence

<400> SEQUENCE: 46
gaccacatta ataattgg                                                18

<210> SEQ ID NO 47
<211> LENGTH: 9
<212> TYPE: DNA
<213> ORGANISM: Artificial Sequence
<220> FEATURE:
<223> OTHER INFORMATION: nucleic acid sequence encoding CDR of NG140

<400> SEQUENCE: 47 ggtgcaacc                                                           9

<210> SEQ ID NO 48
<211> LENGTH: 27
<212> TYPE: DNA
<213> ORGANISM: Artificial Sequence
<220> FEATURE:
<223> OTHER INFORMATION: nucleic acid sequence encoding CDR of NG140

<400> SEQUENCE: 48
caacagtatt ggagtattcc gtggacg                                      27

<210> SEQ ID NO 49
<211> LENGTH: 119
<212> TYPE: PRT
<213> ORGANISM: Artificial Sequence
<220> FEATURE:
<223> OTHER INFORMATION: VH chain of XC252 polypeptide

<400> SEQUENCE: 49

Glu Val Gln Leu Gln Gln Ser Gly Ala Glu Leu Val Arg Pro Gly Val
```

```
                1               5                  10                  15
        Ser Val Lys Ile Ser Cys Lys Gly Ser Gly Tyr Thr Phe Thr Asp Tyr
                        20                  25                  30

Ala Met His Trp Val Lys Gln Ser His Ala Lys Ser Leu Glu Trp Ile
                        35                  40                  45

Gly Val Ile Ser Thr Tyr Tyr Gly Asp Pro Arg Asp Asn Gln Lys Phe
                        50                  55                  60

Lys Gly Lys Ala Thr Met Thr Val Asp Lys Ser Ser Thr Ala Tyr
                        65          70                  75              80

Met Glu Leu Ala Arg Leu Thr Ser Glu Asp Ser Ala Ile Tyr Tyr Cys
                                85                  90                  95

Ala Arg Gly Asp Tyr Asp Trp Tyr Ala Ile Asp Tyr Trp Gly Gln Gly
                        100                 105                 110

Thr Ser Val Thr Val Ser Ser
                    115
```

<210> SEQ ID NO 50
<211> LENGTH: 8
<212> TYPE: PRT
<213> ORGANISM: Artificial Sequence
<220> FEATURE:
<223> OTHER INFORMATION: heavy CDR1 of XC252 polypeptide

<400> SEQUENCE: 50

```
        Gly Tyr Thr Phe Thr Asp Tyr Ala
        1               5
```

<210> SEQ ID NO 51
<211> LENGTH: 8
<212> TYPE: PRT
<213> ORGANISM: Artificial Sequence
<220> FEATURE:
<223> OTHER INFORMATION: heavy chain CDR2 of XC252 polypeptide

<400> SEQUENCE: 51

```
        Ile Ser Thr Tyr Tyr Gly Asp Pro
        1               5
```

<210> SEQ ID NO 52
<211> LENGTH: 12
<212> TYPE: PRT
<213> ORGANISM: Artificial Sequence
<220> FEATURE:
<223> OTHER INFORMATION: heavy chain CDR3 of XC252 polypeptide

<400> SEQUENCE: 52

```
        Ala Arg Gly Asp Tyr Asp Trp Tyr Ala Ile Asp Tyr
        1               5                   10
```

<210> SEQ ID NO 53
<211> LENGTH: 112
<212> TYPE: PRT
<213> ORGANISM: Artificial Sequence
<220> FEATURE:
<223> OTHER INFORMATION: VL chain of XC252 polypeptide

<400> SEQUENCE: 53

```
        Asp Val Val Met Thr Gln Thr Pro Leu Ser Leu Pro Val Ser Leu Gly
        1               5                   10                  15

Asp Gln Ala Ser Ile Ser Cys Arg Ser Ser Gln Ser Ile Val His Ser
                        20                  25                  30

Asp Gly Asn Thr Tyr Leu Glu Trp Tyr Leu Gln Lys Pro Gly Gln Ser
```

```
                35                  40                  45
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 54
<211> LENGTH: 11
<212> TYPE: PRT
<213> ORGANISM: Artificial Sequence
<220> FEATURE:
<223> OTHER INFORMATION: light chain CDR1 of XC252 polypeptide

<400> SEQUENCE: 54

Gln Ser Ile Val His Ser Asp Gly Asn Thr Tyr
1               5                   10

<210> SEQ ID NO 55
<211> LENGTH: 3
<212> TYPE: PRT
<213> ORGANISM: Artificial Sequence
<220> FEATURE:
<223> OTHER INFORMATION: light chain CDR2 of XC252 polypeptide

<400> SEQUENCE: 55

Lys Val Ser
1

<210> SEQ ID NO 56
<211> LENGTH: 9
<212> TYPE: PRT
<213> ORGANISM: Artificial Sequence
<220> FEATURE:
<223> OTHER INFORMATION: light chain CDR3 of XC252 polypeptide

<400> SEQUENCE: 56

Phe Gln Gly Ser His Val Pro Pro Thr
1               5
```

ANTI-HER3 ANTIBODIES AND USES OF SAME

RELATED APPLICATIONS

This application is a National Phase of PCT Patent Application No. PCT/IL2015/050915 having International filing date of Sep. 8, 2015, which claims the benefit of priority under 35 USC § 119(e) of U.S. Provisional Patent Application No. 62/047,168 filed on Sep. 8, 2014. The contents of the above applications are all incorporated by reference as if fully set forth herein in their entirety.

SEQUENCE LISTING STATEMENT

The ASCII file, entitled 69203SequenceListing.txt, created on Mar. 2, 2017, comprising 21,118 bytes, submitted concurrently with the filing of this application is incorporated herein by reference.

FIELD AND BACKGROUND OF THE INVENTION

The present invention, in some embodiments thereof, relates to anti-HER3 antibodies and uses of same.

Growth factors and their transmembrane receptor tyrosine kinases regulate cellular proliferation and migration during both embryogenesis and oncogenesis. The HER family (1) includes four members, the epidermal growth factor receptor, EGFR (ErbB1/HER1), HER2 (c-Neu, ErbB2), HER3 (ErbB3) and HER4 (ErbB4). HER receptors harbor an extracellular domain consisting of four structural subdomains, referred to as domains I-IV (2), followed by a transmembrane domain and an intracellular domain, which provides tyrosine kinase activity. Kinase activation of the HER family members has generally been considered to involve ligand-induced active dimer formation. In this model, except in HER2, structural changes from a tethered to an untethered conformation exposing a dimerization arm (domain II) are induced following ligand induced activation. Therefore, HER proteins are able to form active homodimers or heterodimers or higher class oligomers (3-6). Additional studies revealed the existence of ligand-independent activated dimers, reported in case of receptor overexpression (7). Moreover, other studies reported inactive preformed free or half-free-ligand dimers presenting asymmetric arrangement of the intracellular kinase domain. These inactive dimers can subsequently be activated by ligand binding (8).

HER3, which presents a very low tyrosine kinase activity (9), has an influence on signaling pathways, via its preferential dimerization with EGFR or HER2 and its subsequent phosphorylation by these active tyrosine kinases. These receptors and their many ligands form a layered signaling network, which is multiply involved in human cancer (6). HER3 is activated upon neuregulin (NRG) binding, mainly NRG1β, but unlike EGFR, HER2 and HER4, HER3 does not form homodimers upon ligand binding (10). Similar to EGFR and HER2, the identification of somatic mutations in HER3 was recently reported in colon and in gastric cancer (11), reflecting the importance of this receptor for tumor progression.

Targeted therapies against HER family members using monoclonal antibodies (mAbs) are widely and commonly used in cancer therapy. For example, trastuzumab (Herceptin) that targets HER2 is currently employed routinely in breast cancer therapy (12, 13). However, due to the adaptive character of this disease, the majority of breast cancers become trastuzumab-resistant after prolonged treatment. Several studies reported that trastuzumab resistant tumors show strong expression of HER3 (14). Moreover, HER3 is also implicated in the development of resistance to treatment with other HER-targeted therapies (e.g., cetuximab or kinase inhibitors such as Lapatinib) (15, 16), IGFR-targeted therapies (17) or chemotherapeutic agents (18).

Anti-HER3 antibodies are already in development in several laboratories (19) and some of them are currently in phase I clinical trials. These are MM-121 (20) from Merrimack, U3-1287/AMG888 (21) from U3-Pharma/AMGEN, AV-203 (19) from Aveo and RO5479599 (22) from Roche. In addition, some bispecific molecules targeting HER3 and another receptor have been developed and three of them are currently in phase I clinical trials. These are MM-111 (23) (HER2/HER3; Merrimack), MEHD7945A (24, 25) (EGFR/HER3; Genentech) and MM-141 (26) (IGFR1/HER3; Merrimack). These bispecific strategies are based on the assumption that the dual targeting of two receptors from the EGFR family might be effective in terms of tumor inhibition.

Drugs targeting HER3 that are currently developed or in clinical trials show promising results, but their efficacy can be viewed as modest (32). It is therefore imperative to develop new strategies to improve the benefit of HER3 targeting.

SUMMARY OF THE INVENTION

According to an aspect of some embodiments of the present invention there is provided an isolated polypeptide comprising an antigen recognition domain specifically binding human HER-3 with a $K_D$ value of 10 nM or lower, wherein the polypeptide inhibits neuregulin (NRG) binding to the human HER3 and NRG-induced cancer cell migration and proliferation.

According to some embodiments of the invention, the isolated polypeptide induces HER3 degradation.

According to some embodiments of the invention, the isolated polypeptide induces HER3 degradation faster than NRG stimulation.

According to some embodiments of the invention, the isolated polypeptide of induces HER3 internalization.

According to some embodiments of the invention, the isolated polypeptide induces antibody dependent cell mediated cytotoxicity (ADCC).

According to some embodiments of the invention, the isolated polypeptide inhibits NRG-induced HER3 phosphorylation and optionally AKT and/or ERK activation.

According to some embodiments of the invention, the isolated polypeptide is as efficient as trastuzumab in inhibiting N87 (ATCC® CRL-5822™) proliferation.

According to some embodiments of the invention, the antigen recognition domain comprises complementarity determining region (CDR) amino acid sequences as set forth in:

SEQ ID NOs: 1 (CDR1), 2 (CDR2) and 3 (CDR3), (sequentially arranged from N to C on a light chain of the polypeptide) and 4 (CDR1), 5 (CDR2) and 6 (CDR3) (sequentially arranged from N to C on a heavy chain of the polypeptide) (Clone NG33).

According to an aspect of some embodiments of the present invention there is provided an isolated polypeptide comprising an antigen recognition domain which specifically binds human HER-3, wherein the antigen recognition domain comprises complementarity determining region (CDR) amino acid sequences as set forth in:

SEQ ID NOs: 1 (CDR1), 2 (CDR2) and 3 (CDR3), (sequentially arranged from N to C on a light chain of the polypeptide) and 4 (CDR1), 5 (CDR2) and 6 (CDR3) (sequentially arranged from N to C on a heavy chain of the polypeptide) (Clone NG33);

SEQ ID NOs: 7 (CDR1), 8 (CDR2) and 9 (CDR3), (sequentially arranged from N to C on a light chain of the polypeptide) and 10 (CDR1), 11 (CDR2) and 12 (CDR3) (sequentially arranged from N to C on a heavy chain of the polypeptide) (Clone NG83); or SEQ ID NOs: 13 (CDR1), 14 (CDR2) and 15 (CDR3), (sequentially arranged from N to C on a light chain of the polypeptide) and 16 (CDR1), 17 (CDR2) and 18 (CDR3) (sequentially arranged from N to C on a heavy chain of the polypeptide) (Clone NG140).

According to some embodiments of the invention, the isolated polypeptide is an antibody or a fragment thereof.

According to some embodiments of the invention, the antibody is a monoclonal antibody.

According to some embodiments of the invention, the antibody is a monospecific antibody.

According to some embodiments of the invention, the antibody is a multispecific antibody.

According to some embodiments of the invention, the multispecific antibody is a bispecific antibody.

According to some embodiments of the invention, the antibody is a humanized antibody.

According to some embodiments of the invention, the antibody is attached to a heterologous moiety.

According to some embodiments of the invention, the heterologous moiety is a pharmaceutical agent.

According to some embodiments of the invention, the pharmaceutical agent comprises a cytotoxic agent.

According to some embodiments of the invention, the cytotoxic agent is an enzymatically active toxin.

According to some embodiments of the invention, the cytotoxic agent is a chemotherapeutic agent or a radioactive isotope.

According to some embodiments of the invention, the antibody is immobilized to a solid phase.

According to some embodiments of the invention, the antibody is an IgG1 subtype.

According to some embodiments of the invention, the multispecific antibody binds a HER polypeptide selected from the group consisting of HER1, HER2 and HER4.

According to some embodiments of the invention, the multispecific antibody binds a HER polypeptide selected from the group consisting of HER1 and HER2.

According to some embodiments of the invention, the multispecific antibody binds HER2.

According to some embodiments of the invention, the multispecific antibody binds an epitope in the HER3 which is distinct from the epitope bound by the antigen recognition domain.

According to an aspect of some embodiments of the present invention there is provided a pharmaceutical composition comprising the isolated polypeptide of any one of claims and a pharmaceutically acceptable carrier or diluent.

According to an aspect of some embodiments of the present invention there is provided a cell line which produces the isolated polypeptide.

According to an aspect of some embodiments of the present invention there is provided a method of determining presence of HER3 polypeptide in a cell suspected of containing the HER3 polypeptide, the method comprising contacting the cell with the isolated polypeptide under conditions which allow formation of an immunocomplex comprising the HER3 polypeptide and the isolated polypeptide, and determining presence of the immunocomplex, thereby determining presence of HER3 polypeptide in the cell.

According to an aspect of some embodiments of the present invention there is provided a kit comprising the isolated polypeptide and instructions for using the isolated polypeptide to detect a HER3 polypeptide.

According to an aspect of some embodiments of the present invention there is provided a kit comprising the isolated polypeptide and a pharmaceutical agent.

According to some embodiments of the invention, the pharmaceutical agent is a cytotoxic agent selected from a chemotherapy and a radioisotope.

According to an aspect of some embodiments of the present invention there is provided a method of treating a HER3 associated medical condition in a subject in need thereof, the method comprising administering to the subject a therapeutically effective amount of the isolated polypeptide, thereby treating the HER3 associated medical condition.

According to an aspect of some embodiments of the present invention there is provided use of the isolated polypeptide in the manufacture of a medicament identified for treating a HER3 associated medical condition.

According to an aspect of some embodiments of the present invention there is provided the isolated polypeptide in the treatment of a HER3 associated medical condition.

According to some embodiments of the invention, the HER3 associated medical condition is a hyperproliferative disease.

According to some embodiments of the invention, the hyperproliferative disease is cancer.

According to some embodiments of the invention, the cancer is selected from the group consisting of melanoma, breast cancer, ovarian cancer, renal carcinoma, gastrointestinal/colon cancer, lung cancer, clear cell sarcoma and prostate cancer.

According to some embodiments of the invention, the cancer exhibits autocrine NRG-induced signaling.

According to some embodiments of the invention, the method further comprising analyzing expression of the HER3 and/or NRG in cells of the cancer.

According to some embodiments of the invention, the method further comprising administering to the subject an additional polypeptide, wherein such that the polypeptide comprises the CDRs of clone NG33 and the additional polypeptide comprises the CDRs of clone NG140 or NG83.

According to an aspect of some embodiments of the present invention there is provided a method of producing the isolated polypeptide, comprising culturing a host cell expressing the polypeptide so that the polypeptide is produced.

According to some embodiments of the invention, the method further comprising isolating the polypeptide from the culture.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 4A, 4B:
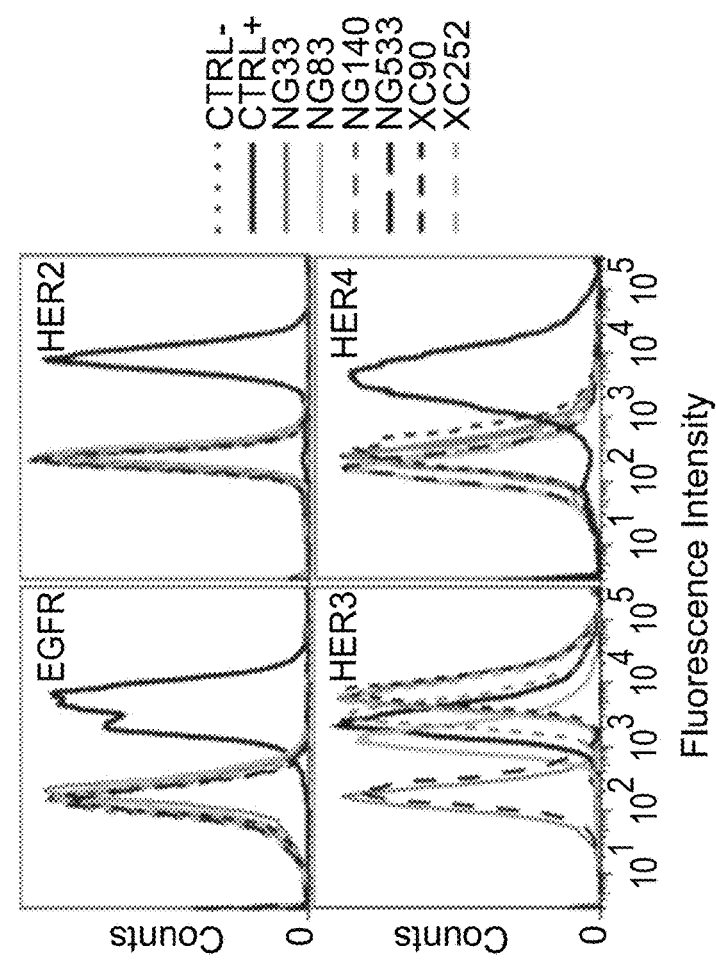

FIGS. 1A-E show hybridoma Screening and mAb Isotyping. (FIG. 1A) Mice were immunized with recombinant IgB3. (FIG. 1B) The hybridoma supernatant screening using ELISA, was performed on 96 well-plate coated with IgB3 (1 µg/ml) or with a human IgG. The plates were blocked with PBS-1% BSA and incubated for 1 h with hybridoma supernatants, followed by a second incubation for 1 h with HRP-labeled anti-mouse IgG and subsequently detected by 2,2'-azino-bis (3-ethylbenzothiazoline-6-sulfonic acid) addition. The OD at 415 nm was then measured using an ELISA microplate reader. (FIG. 1C) The second step of the screening was performed by immunoprecipitation (IP). Anti-mouse IgG beads were incubated first with the hybridoma supernatant and subsequently with total cell lysate from HER3-expressing T47D cells. (FIG. 1D) The mAbs directed to HER3 were isotyped using ELISA. 96 well-plate were coated with IgB3 (1 µg/ml) and after blocking, incubated with the indicated mAbs for 1 h. After washing the plate were incubated for 1 h with various secondary HRP coupled-antibodies able to bind specifically, IgG1, IgG2a, IgG2b, IgG3, IgM, IgA, Kappa chain or Lambda chain. The detection was performed as shown in FIG. 1B. (FIG. 1E) Finally the ability of the mAbs to detect HER3, used as primary Ab in a Western Blot experiment, was determined on cell lysate from T47D cells.

FIGS. 2A-D show monoclonal antibody targeting HER3 extracellular domain. (FIG. 2A) 96 well-plates were coated with 1.5 µg/ml of IgB3, blocked with PBS-BSA (1% weight/vol) and incubated for 1 h with various concentrations of purified mAbs under gentle shaking at RT. After washing, a second 1 h-incubation with HRP-labelled anti-mouse IgG was performed and followed by incubation with 2,2'-azino-bis (3-ethylbenzothiazoline-6-sulfonic acid) for 10 min. The OD at 415 nm was measured using by an ELISA microplate reader. (FIGS. 2B and 2C) NIH/3T3-R2R3 cells were incubated with 10 µg/ml of each mAb for 1 h at 4° C. After 2 washes, the cells were incubated for 1 h at 4° C. (in the dark) with a secondary anti-mouse IgG Ab coupled to AlexaFluor 488. The fluorescence intensity (F.I.) was measured on the LSRII flow cytometer. (FIG. 2D) Protein G beads were incubated first with the indicated mAb (5 µg) for 2 h at 4° C. under gentle shaking and following two washes, the beads were incubated with cleared cell lysate from N87 cells. After 4 washes, the content bound to the beads was eluted and analyzed by immunoblotting (IB) with an antibody to HER3/ErbB-3.

FIGS. 3A-E show Kd determination of mAb to HER3 using the Tag-Lite technology. Cells are transfected with HER3-SNAP-Tag and labeled with BG-Lumi4(Tb), a SNAP-tag subtract. Following incubation with increasing concentrations of indicated d2 labeled mAb directed to HER3, the Kd was determined from the binding curve fitting. The binding curve was obtained by measuring the FRET between the donor Lumi4(Tb) and the acceptor d2-dye. The unspecific binding was evaluated by adding an excess of unlabelled Ab.

FIGS. 4A-B show specificity of monoclonal antibodies directed to HER3. (FIG. 4A) NIH/3T3-EGFR, -HER2, -HER3 or -EGFR/HER4 cells were incubated with 25 µg/ml of each mAb for 1.5 h at 4° C. After 2 washes, the cells were incubated for 1 h at 4° C. (in the dark) with a secondary anti-mouse IgG Ab coupled to AlexaFluor 488. The fluorescence intensity (F.I.) was measured on the LSRII flow cytometer. The negative control is made using an irrelevant mouse IgG as primary Ab. The positive control are the following mAb 565 (anti-EGFR), mAb L26 (anti-HER2), mAb 9F7 (anti-HER3), mAb 77 (anti-HER4). (FIG. 4B) The panel presents the geometric mean and the CV of the fluorescence intensity.

FIGS. 5A-D show that the monoclonal Antibody induces HER3 degradation and Antibody-Dependent Cell-mediated Cytotoxicity. (FIGS. 5A and 5B) The mAb ability to degrade HER3 after cell treatment was determined as follows. N87 cells were treated for 3 h at 37° C. with 10 µg/ml mAb. After cell lysis and protein extraction, the samples were subjected to immunoblotting with the indicated Ab. (FIG. 5C) The experiment shown in FIG. 5A was performed on 6 other cancer cell lines. (FIG. 5D) The mAb capacity to induce ADCC is reported. BXPC3-luc cells were incubated with the indicated mAbs and secondarily with human PBMC cells for 24 h. Cell killing was detected by measuring the luminescence after final addition of luciferine. *** $p>0.001$, ANOVA and post hoc tests.

Figure 6:
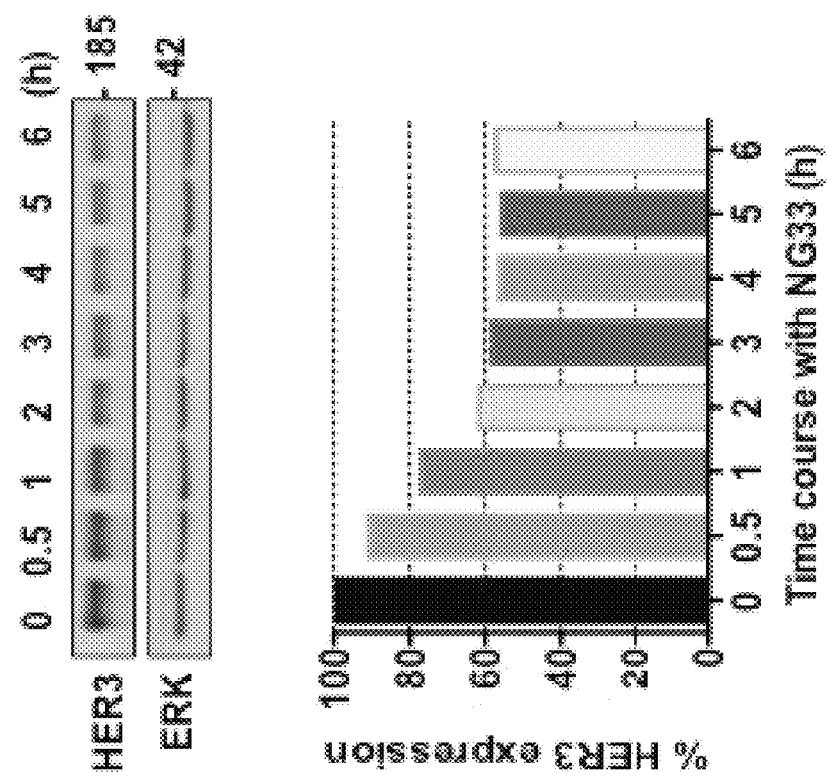

FIG. 6 shows that the anti-HER3 mAb NG33 induces HER3 degradation. SKBR-3 human mammary cancer cells were treated for the indicated times at 37° C. with 10 µg/ml NG33. Following cell lysis and protein extraction, the samples were subjected to immunoblotting using the indicated antibodies followed by and quantification.

Figure 7A:
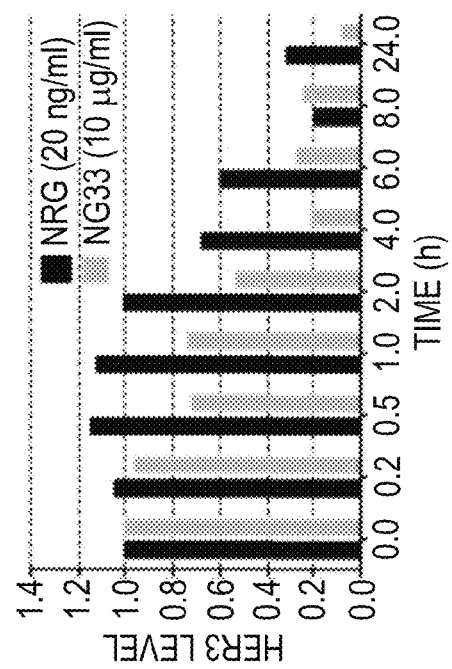
Figure 7B:
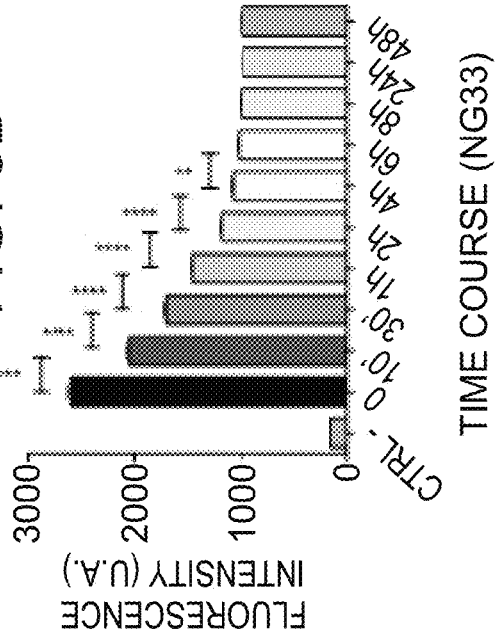

FIGS. 7A-B show that NG33 mAb treatment induces HER3 degradation faster than NRG stimulation. NG33 and NRG abilities to degrade HER3 after cell treatment were determined as follows. N87 cells were treated for the indicated time at 37° C. with 10 µg/ml mAb or 20 ng/ml NRG. After cell lysis and protein extraction, the samples were subjected to immunoblotting with the indicated Ab. (FIG. 7A) Immunoblot photographs. FIG. 7B) HER3 levels were compared and reported in a histogram for comparison.

Figure 8A:
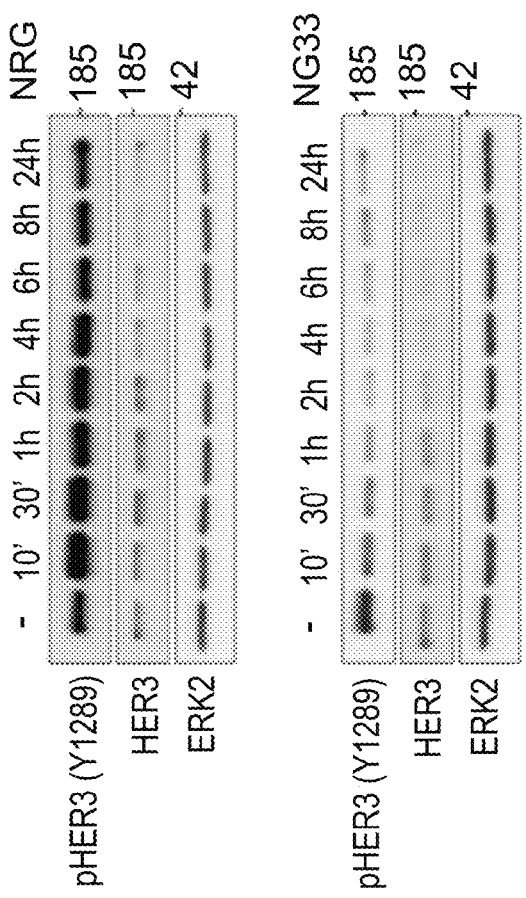
Figure 8B:
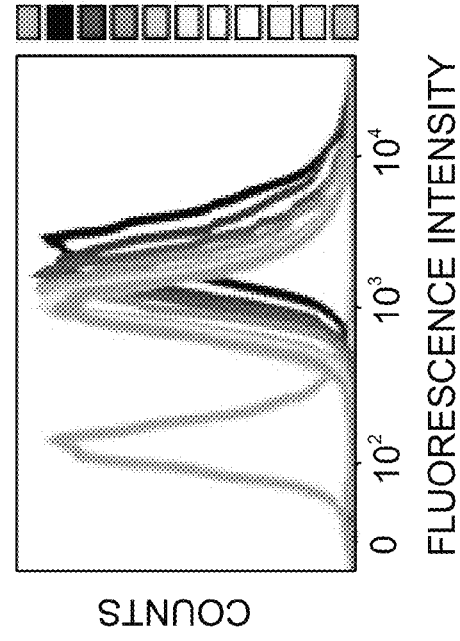

FIGS. 8A-B show that NG33 mAb treatment induces HER3 internalization. N87 cells were incubated for different time intervals with NG33 mAb (10 µg/ml), followed by incubation with a non-competitive anti-HER3 mAb labeled with Vhycoerythrin (PE) and flow cytometry analysis. (FIG. 8A) Flow cytometry histograms. (FIG. 8B) A graph comparing fluorescence intensity at the indicated incubation time points ** $p>0.0001$,  $p>0.01$ (ANOVA and post hoc tests).

FIGS. 9A-C show that the anti-HER3 mAb NG33 decreased NRG-induced phosphorylation of HER3, AKT and ERK, and NRG-induced migration. (FIG. 9A) The indicated mAbs were checked for their capacity to compete with fluorescent dye labeled NRG. NIH/3T3-R2R3 cells were plated on black microplate and incubated 45 min at 4° C. with increasing concentrations of mAbs to HER3. After washes, the labeled-NRG was added and incubated for 30 min at 4° C. Fluorescence intensity at 670 nm was determined following 3 final washes. (FIG. 9B) The ability of the mAbs to avoid NRG-induced phosphorylation of HER3, AKT and ERK, was studied with N87 cells. After 20 min treatment with the indicated mAbs (10 μg/ml) at 37° C., NRG (20 ng/ml) was added to the cells for 10 min. The cells were then lysed, and equal quantities of protein lysates were run on 9% bisacrylamide gel before immunoblotting with the indicated primary antibodies. (FIG. 9C) The capacity of mAb NG33 to avoid NRG-induced migration was checked with OVCAR-5 cells and the quantification reported in a histogram. OVCAR-5 cells were seeded in the upper compartment of migration chambers. The lower compartment of each chamber was filled with medium supplemented with NRG (10 ng/ml). After 24 h-treatment, cells that reached the lower side of the filter were fixed, permeabilized and stained with GIEMSA solution. Signals of triplicates were quantified. **** p>0.0001 (ANOVA and post hoc tests).

FIGS. 10A-D show that the anti-HER3 mAb NG33 decreased NRG-induced tumor cell survival as efficiently as Trastuzumab in vitro and in vivo. (FIGS. 10A and 10C) Proliferation assays using MTT were performed on 5 different cell lines, MCF-7, NCI-H322M, OVCAR-5, SKBR-3, BxPC3 and N87. 5,000 cells per well were plated the day before and treated for 72 h with the various agents (each at 10 μg/ml) in medium supplemented with NRG (10 ng/ml). Trastu indicate a humanized mAb to HER2/ErbB-2, Trastuzumab. (FIG. 10B) N87 cells were incubated with 10 μg/ml of mAb directed to EGFR (565), HER2 (L26) or HER3 (XC252) for 1 h at 4° C. After 2 washes, the cells were incubated for 1 h at 4° C. (in the dark) with a secondary anti-mouse IgG Ab coupled to AlexaFluor 488. The fluorescence intensity (F.I.) was measured on the LSRII flow cytometer. (FIG. 10D) CD1-Nude mice were grafted subcutaneously with $5 \times 10^6$ N87 cells. Once the tumors became palpable (after 13 days) the mice were randomized into group of 6 mice and treated twice a week for 5 weeks. The control group (CTRL) was injected intra-peritoneally (IP) with 200 μl PBS. The other groups were treated with mAb at the final concentration of 0.2 mg/0.2 ml of PBS per mouse. The mice were weighted once a week and the tumors measured twice a week. An average tumor size of 6 mice (+/−SEM) is shown.

Figure 11:
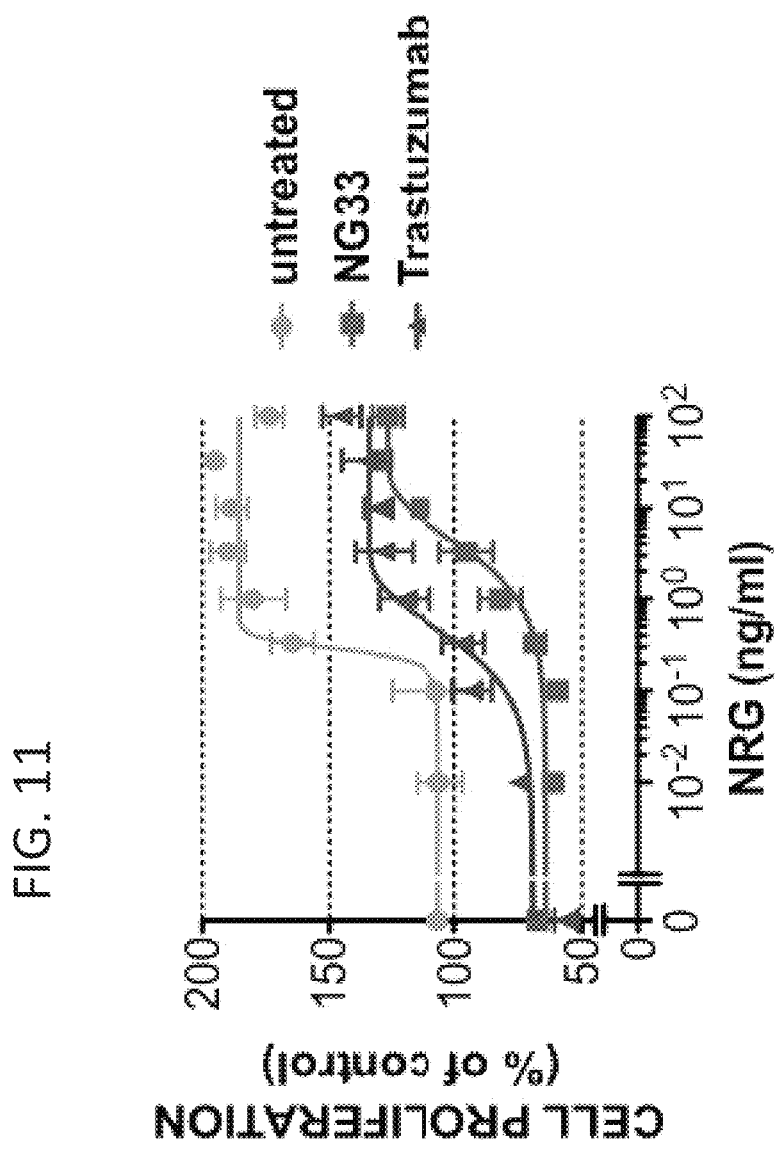

FIG. 11 is a graph showing that the anti-HER3 mAb NG33 decreased NRG-induced gastric cancer cell survival in vitro as efficiently as Trastuzumab as shown in an MTT assay performed on N87 cells. 5,000 cells per well were plated the day before and treated for 72 hours with the indicated mAbs (each at 10 μg/ml) in medium supplemented with the indicated concentrations of NRG.

FIGS. 12A-D show a combination of two mAbs directed to two different epitopes of HER3. (FIGS. 12A and 12B) The antibodies NG33 and XC252 were labeled with the fluorescent dye Lumi4® Tb Cryptate (K2). 96 well-plate were coated with IgB3 (1.5 μg/ml), blocked with PBS-BSA and incubated for 1 h with various concentrations of mAbs under gentle shaking at RT. The labeled mAb, NG33-K2 (FIG. 12A) or XC252-K2 (FIG. 12B), was then added at 1 nM final concentration. After ah incubation, the plate was washed 4 times with KREBS buffer, and the fluorescence intensity at 610 nm was measured using a fluorescence microplate reader. (FIG. 12C) The various anti-HER3 mAb combinations were studied for their ability to trigger HER3 degradation using N87 cells. Cells were treated for 2 h at 37° C. with mAb (10 μg/ml). After cell lysis and protein extraction, the samples were subjected to immunoblotting with the indicated antibodies. (FIG. 12D) The combination's capacity to modulate NRG-induced phosphorylation of HER3, AKT and ERK was evaluated using N87 cells. After 20 min treatment at 37° C. with 10 μg/ml of mAbs, NRG (20 ng/ml) was added to the cells for 10 min. The cells were then lysed, and equal quantities of lysate protein were electrophoresed before immunoblotting, as indicated.

Figure 13:
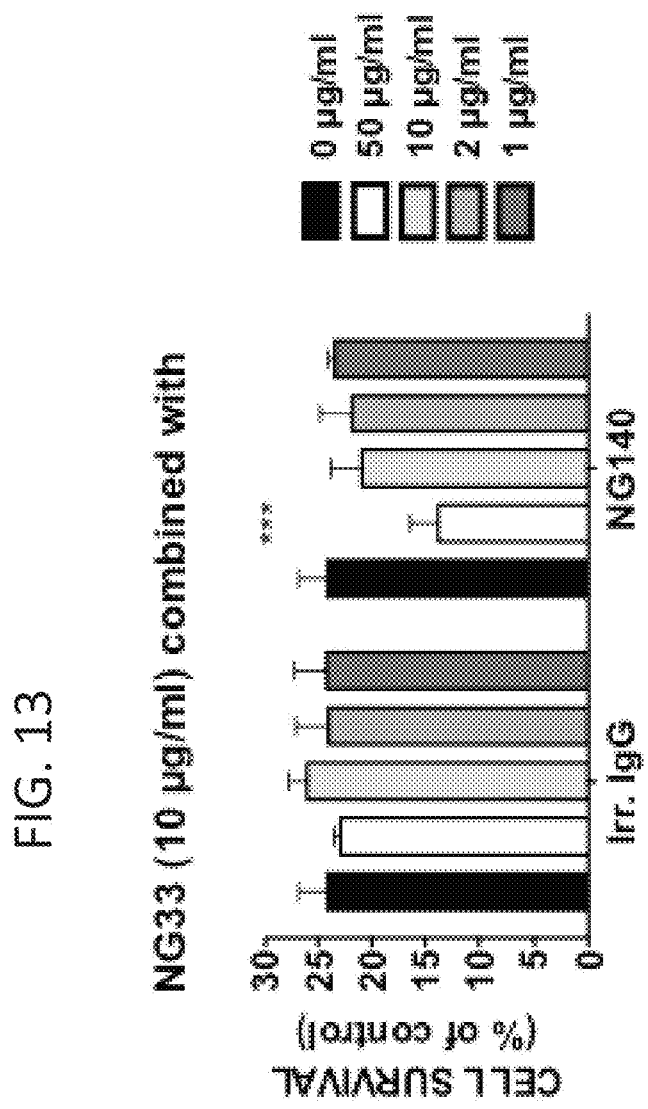

FIG. 13 is a graph showing that combining the anti-HER3 mAbs NG33 and NG140 enhances the inhibitory effect of a single NG33 treatment on proliferation of NRG-induced gastric cancer cell survival in vitro. as shown in an MTT assay performed on N87 cells. 5,000 cells per well were plated the day before and treated for 72 hours with the indicated mAbs at the indicated concentrations in medium supplemented with NRG (1 ng/ml) and NG33 (10 μg/ml). A sample incubated in a medium without NG33 was used for normalization.

Figure 14:
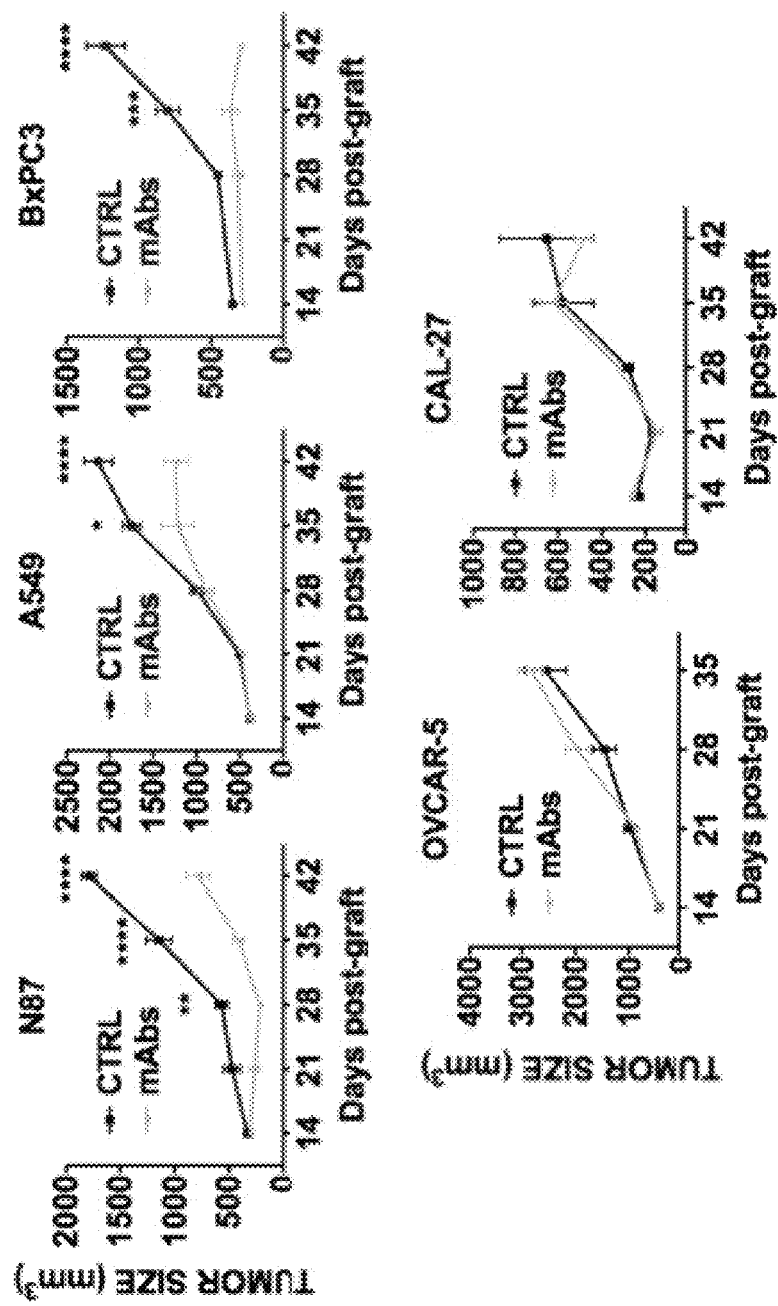

FIG. 14 shows in vivo tests determining the effect of anti-HER3 mAb combinations on several types of carcinomas. CD1-Nude mice were grafted subcutaneously with $5 \times 10^6$ cells. Once tumors became palpable, the mice were randomly divided into groups of 3 mice and were injected twice a week, intra-peritoneally (IP) with the indicated treatments for 5 weeks. The control group (CTRL) was injected with 200 μl PBS, while the "mAbs" group were treated with the NG33+XC252 combination at a final concentration of 0.2 mg/0.2 ml of PBS per mouse. The mice were weighted and the tumors measured once a week. The average tumor size of 3 mice (+/−SEM) is reported.

FIGS. 15A-F show the effects of a mixture of two anti HER3 mAbs, in vivo on BxPC3 cell xenografts and in vitro. (FIGS. 15A-C) CD1-Nude mice were grafted subcutaneously with $5 \times 10^6$ BxPC3 cells. Once tumors became palpable (after 13 days), the mice were randomized into group of 8 mice and treated every 3 days for 5 weeks. The control group (CTRL) was injected intra-peritoneally (IP) with 200 μl PBS. The other groups were treated with mAb alone or in combination at a final concentration of 0.2 mg/0.2 ml of PBS per mouse. The mice were weighted once a week and the tumors measured twice a week. An average tumor size of 7-8 mice (+/−SEM) is shown. (FIGS. 15D-F) Proliferation assays using MTT were performed on BxPC-3. 5,000 cells per well were plated the day before and treated for 72 h with the indicated mAb treatment. Decreasing concentrations of the indicated mAb (alone or in combination) were used in medium supplemented with 1% serum and NRG (10 ng/ml).

Figure 16:
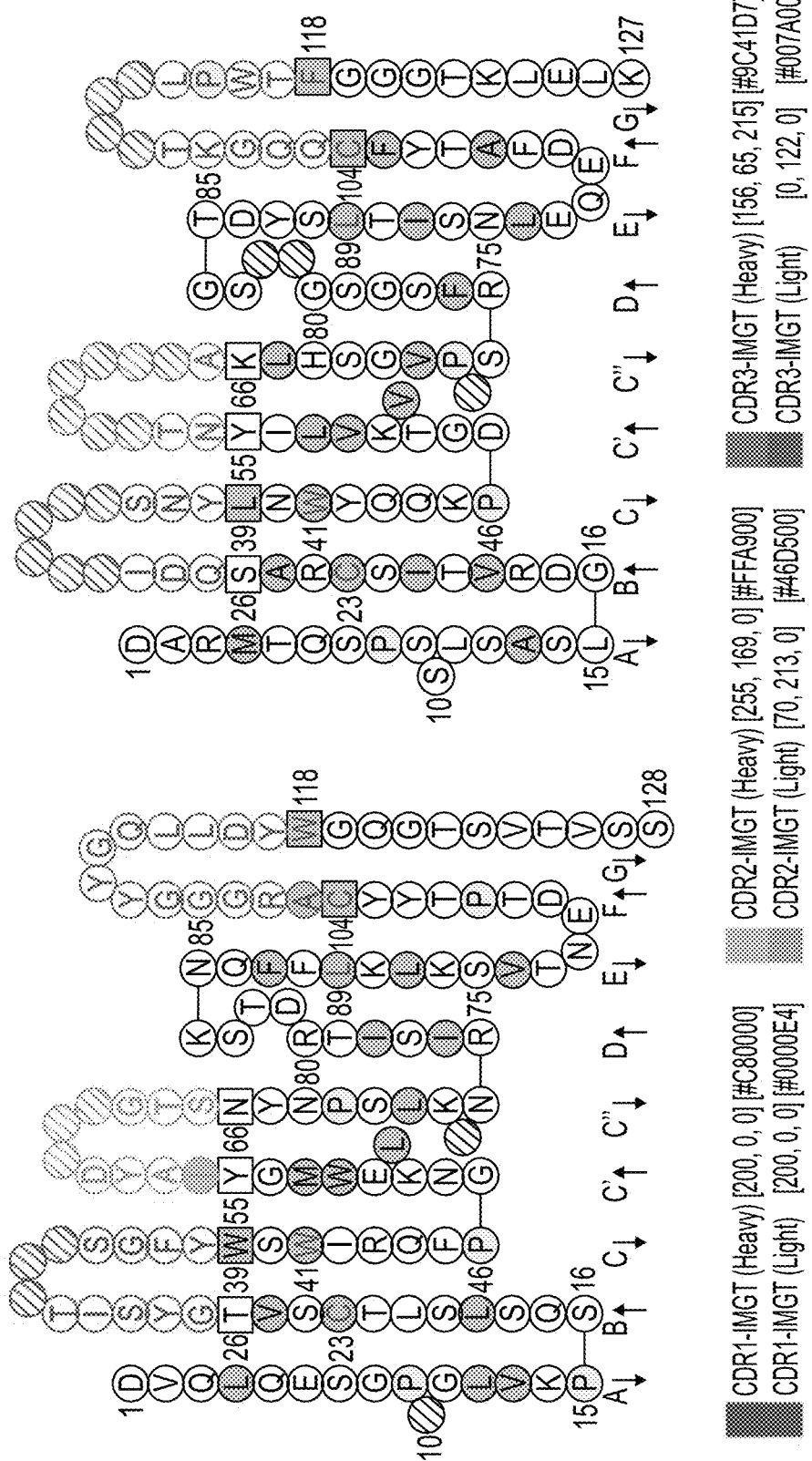
Figure 17:
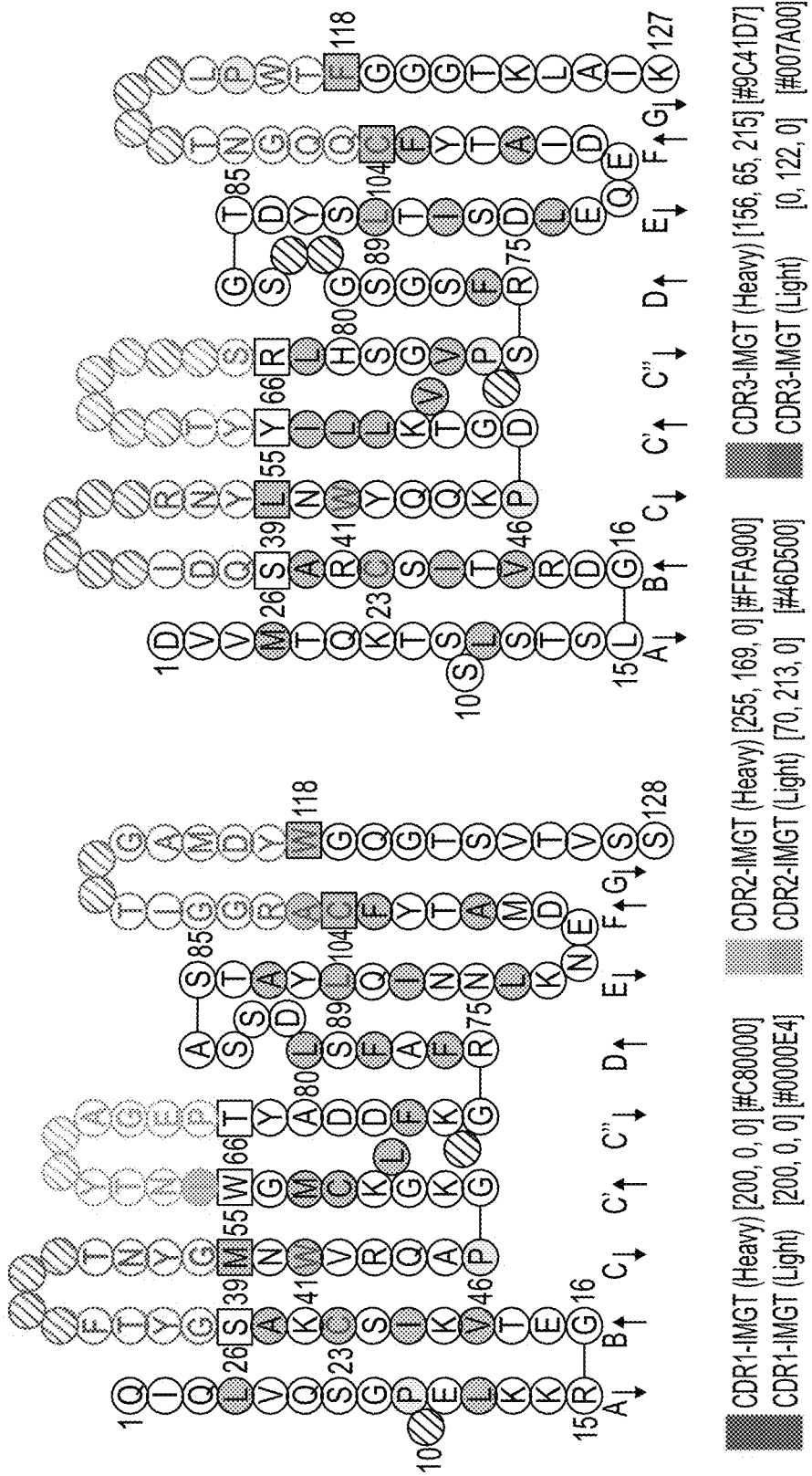
Figure 18:
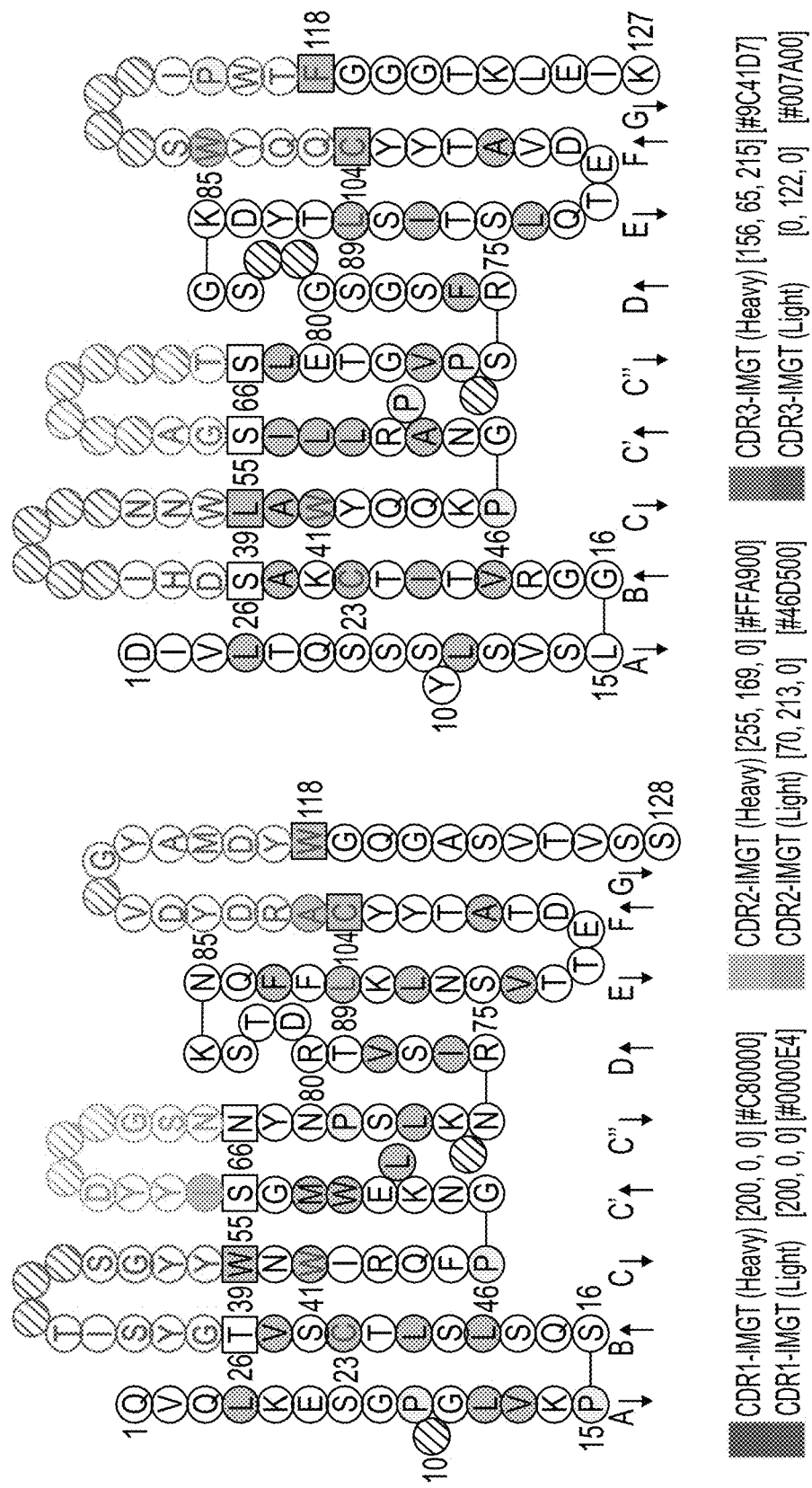
Figure 19:
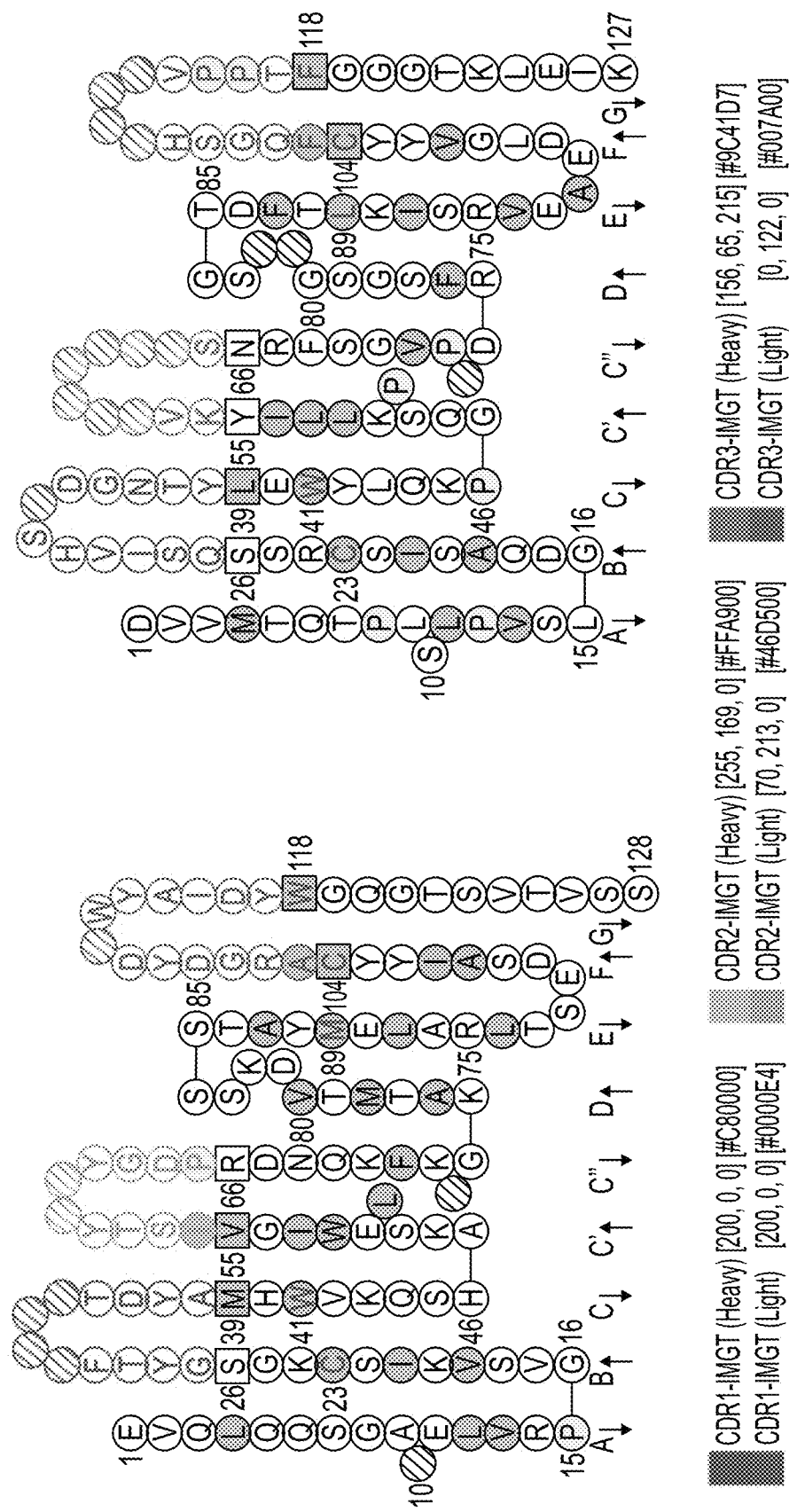
Figure 20:
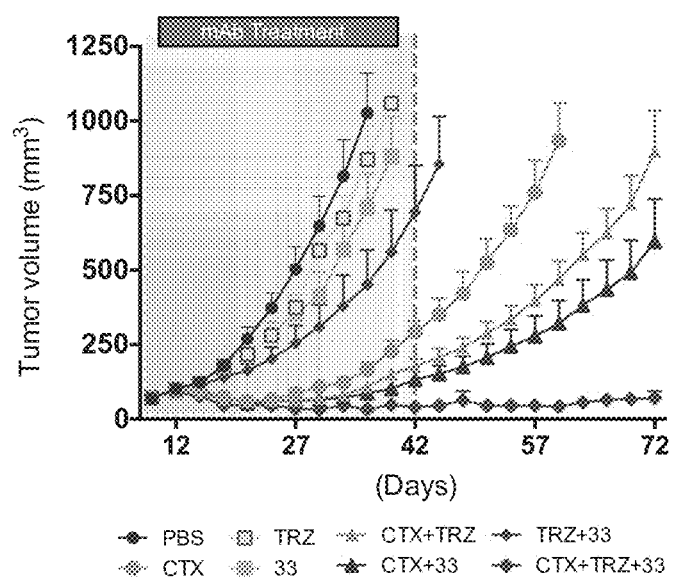

FIG. 16 is a schematic illustration of the NG33 antibody.
FIG. 17 is a schematic illustration of the NG83 antibody.
FIG. 18 is a schematic illustration of the NG140 antibody.
FIG. 19 is a schematic illustration of the XC252 antibody.
FIG. 20 shows the in-vivo effect of treatment with PBS or cetuximab (denoted CTX), trastuzumab (denoted TRZ) and anti-HER3 (mAb 33, denoted 33) and combinations of the three on tumor growth in mice inoculated with PC9ER NSCLC cells. The graph represents tumor volumes following treatment. Data is presented as mean±SE (n=9).

Figure 21A:
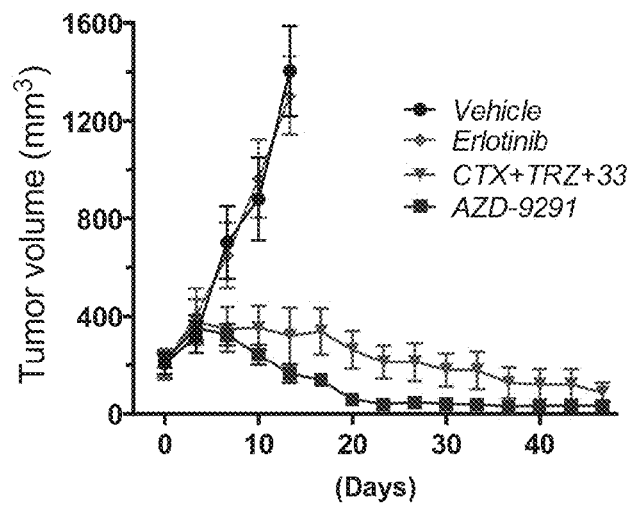
Figure 21B:
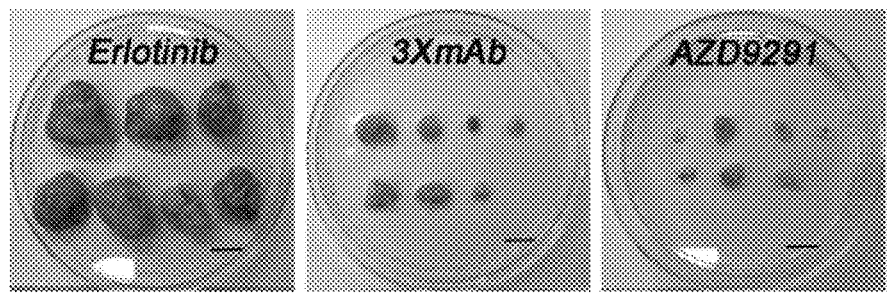
Figure 21C:
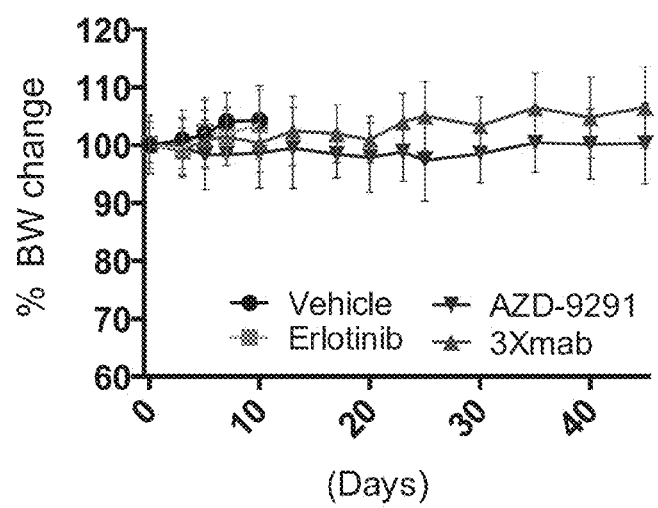

FIGS. 21A-C show that treatment with AZD-9291 (a third generation TKI) and combined treatment with cetuximab (denoted CTX), Trastuzumab (denoted TRZ) and anti-HER3 (mAb 33, denoted 33) comparably inhibit erlotinib resistant NSCLC tumor growth in-vivo. CD1-nu/nu mice were inoculated with H1975 NSCLC cells and treated with Vehicle, Erlotinib or AZD9291 (5 mg/kg/day) or with the triple combination of antibodies (CTX+TRZ+33). FIG. 21A is a graph representing tumor volumes following treatment. Data is presented as mean±SE (n=8). FIG. 21B show photographs demonstrating tumors harvested from the tumor bearing mice. The images show tumors harvested from Erlotinib treated mice on day 14 and from AZD9291 or the triple combination of antibodies (denoted as 3×mAb) treated mice on day 43. Scale bar represents 1 cm. FIG. 21C is a graph representing body weight changes following treatment.

Figure 22:
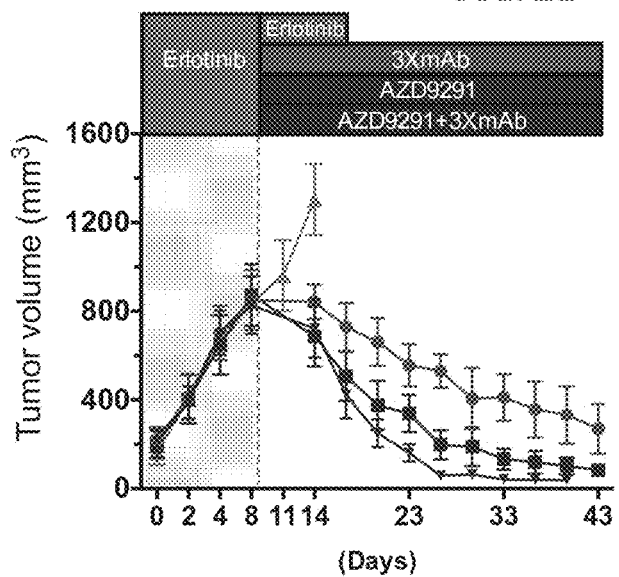

FIG. 22 shows the in-vivo effect of a combined treatment with AZD-9291 and the triple antibody combination (cetuximab+trastuzumab+mAb 33, denoted 3×mAb) on erlotinib resistant NSCLC tumor growth in mice inoculated with H1975 cells. CD1-nu/nu mice were first treated with Erlotinib until tumors reached a size of 800 mm³ followed by treatment with, Erlotinib or AZD9291 (5 mg/kg/day), 3×mAb or 3×mAb in combination with AZD9291 (1 mg/kg/day). The graph represents tumor volumes following treatment. Data is presented as mean±SE (n=7).

Figure 23:
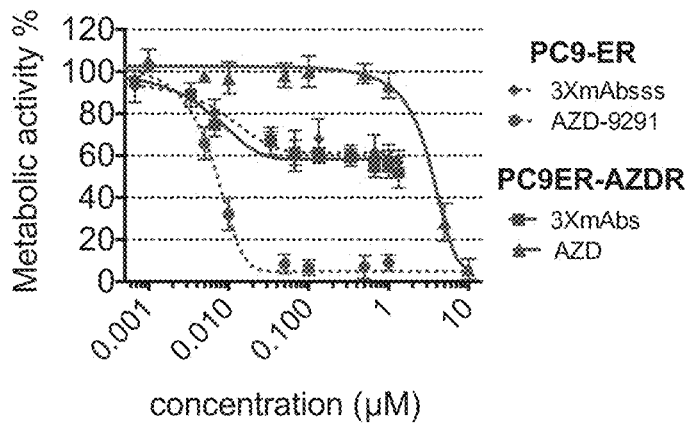

FIG. 23 demonstrates that NSCLC cells develop resistance to AZD-9291 (denoted AZD) but remain sensitive to treatment with the triple mAb combination (cetuximab+trastuzumab+mAb33, denoted 3×mAb). The graph represents metabolic activity percentages of PC9ER and PC9ER-AZDR cells following 72 hours treatment with increasing doses of AZD-9291 or 3×mAb, as evaluated by MTT assay. Data is presented as average±SD (n=3 independent experiments).

Figure 24:
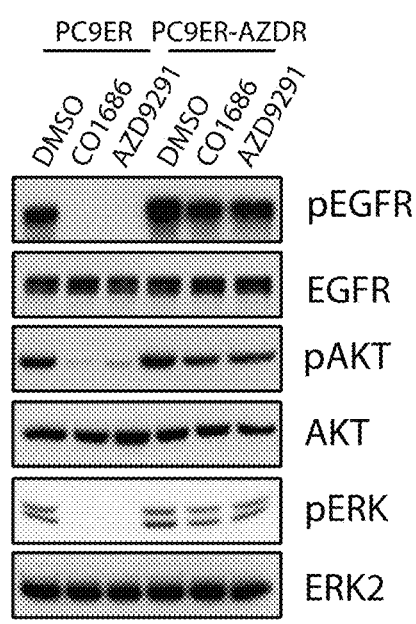

FIG. 24 shows western-blot photographs demonstrating expression of EGFR, AKT, ERK2 and their phosphorylated forms in NSCLC PC9ER and PC9ER-AZDR cells following 6 hours treatment with DMSO control, 1 µM CO-1686 or 1 µM AZD-9291.

DESCRIPTION OF SPECIFIC EMBODIMENTS OF THE INVENTION

The present invention, in some embodiments thereof, relates to anti-HER3 antibodies and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The epidermal growth factor receptor (EGFR) family serves as a key target for cancer therapy. Specifically, EGFR and HER2 have been intensely targeted; due to their overexpression in several tumor types. Therapeutic interest in HER3 targeting has long been underestimated due to relatively low expression in tumor and impaired kinase activity.

Drugs targeting HER3 that are currently developed or in clinical trials show promising results, but their efficacy can be viewed as modest (32).

Whilst reducing the present invention to practice, the present inventors have developed a novel panel of anti HER3 antibodies and characterized the antibodies regarding their ability to degrade HER3 and to decrease HER3 activity. NG33 (also referred to herein as 33), a mAb targeting the NRG binding site of HER3 emerge as the most potent (illustrated in FIG. 16). Secondly, competition assays against NG33 were performed to identify several mAbs to use in combination with NG33, also known as the double targeting approach. Eventually, three different combinations (i.e., N33+N140, NG33+NG83 and NG33+XC252) were selected and their efficacy to decrease tumor cell proliferation compared to the one of NG33 single treatment was found unprecedented. In addition, the present inventors have shown that a combined treatment comprising NG33 with cetuximab (anti-EGFR) and trastuzumab (anti-HER2) exerted synergistically strong and lasting inhibitory effects on tumor growth both in-vitro and in-vivo. Furthermore, the present inventors have uncovered that a combination of NG33 with cetuximab and trastuzumab and a low dose of a third generation TKI which inhibits mutated EGFR while sparring wild-type EGFR e.g., AZD-9291 had an improved anti-tumor effect on erlotinib resistant NSCLC tumors as compared to the triple mAb therapy or to a high dose AZD-9291 therapy.

These results place the antibodies either as single agents or in combinations as important clinical tools for the diagnosis and treatment of HER3 associated medical conditions such as cancer.

Thus, according to an aspect of the invention there is provided an isolated polypeptide comprising an antigen recognition domain specifically binding human HER-3 with a $K_D$ value of 10 nM or lower, wherein said polypeptide inhibits neuregulin (NRG) binding to said human HER3 and NRG-induced cancer cell migration and proliferation.

As used herein, "a protein" refers to an isolated polypeptide molecule having a high affinity towards HER3.

As used herein "a high affinity molecule" which is interchangeably referred to as "the protein" or "the isolated protein" refers to a naturally-occurring or synthetic essentially proteinacious molecule, which binds specifically a target protein molecule (i.e., HER3) with an affinity higher than $10^{-6}$ M. Specific binding can be detected by various assays as long as the same assay conditions are used to quantify binding to the target versus control.

According to a specific embodiment, the protein is an antibody.

The general affinity of the protein is preferably higher than about, $10^{-9}$ M, $10^{-10}$ M and as such is stable under physiological (e.g., in vivo) conditions.

According to a specific embodiment the affinity is preferably between $0.1\text{-}10^{-9}$ M, $1\text{-}10\times10^{-9}$ M or $0.1\text{-}10\times10^{-9}$ M. According to a specific embodiment the affinity is between $1\text{-}10\times10^{-9}$ M. According to another specific embodiment the affinity is between $0.1\text{-}5\times10^{-9}$ M.

As used herein the term "isolated" refers to a level of purity such that the protein of the invention is the predominant form (e.g., more than 50%) in the preparation. In other words, other high affinity molecules which are characterized by low or no affinity to HER3 are altogether present in the preparation in less than 50% of the total high affinity molecules of the preparation. According to a specific embodiment, the protein is isolated from the physiological embodiment e.g., from the body (e.g., human or animal). According to a specific embodiment, the term isolated also means isolated from a library, such as a phage display library.

As used herein "HER3" refers to a receptor tyrosine kinase (RTK) of the epidermal growth factor receptor family E.C. 2.7.10.1, also referred to as ErbB-3. According to a specific embodiment, the HER3 is ERBB3_HUMAN, P21860.

According to a specific embodiment, the protein does not bind another HER family member i.e., HER1, HER2 or HER4 with a clinically relevant affinity i.e., higher than $10^{-8}$ M.

As used herein "EGF-R" refers to a receptor tyrosine kinase (RTK) of the epidermal growth factor receptor family, also referred to as HER1, mENA and ErbB-1. According to a specific embodiment the EGFR is human EGFR i.e., EGFR_HUMAN, P00533.

As used herein "HER2" refers to a receptor tyrosine kinase (RTK) of the epidermal growth factor receptor family, also referred to as ErbB-2, NEU and p185erbB-2. According to a specific embodiment the HER2 is human HER2 i.e., ERBB2_HUMAN, P04626.

As used herein, the term "HER4" refers to a receptor tyrosine kinase (RTK) of the epidermal growth factor receptor family, also referred to as ErbB-4. According to a specific embodiment the HER4 is human HER4 i.e., ERBB4_HUMAN, Q15303.

As mentioned the isolated polypeptide is capable of inhibiting binding of neuregulin to HER3.

As used herein, the term "neuregulin" or NRG refers to Neuregulin 1 (NRG1).

NRG activates the ErbB2-ErbB3 protein complex (i.e. induces phosphorylation of tyrosine residues in the ErbB2-ErbB3 complex upon binding thereto). The term includes biologically active fragments and/or variants of a naturally occurring NRG polypeptide, such as an EGF-like domain fragment thereof (e.g. NRGbeta$_1$ 177-244).

According to a specific embodiment, "capable of inhibiting binding of neuregulin to HER3" means that the protein binds to the binding site of NRG on HER3 and competes with NRG binding, similarly to a competitive inhibitor. Thus binding of the protein to HER3 prevents NRG binding to HER3. Accordingly, the apparent affinity of NRG to HER3 in the presence of the protein is increased. Alternatively, the antibody may induce conformational changes in HER3 thus inhibiting NRG binding to the receptor.

As mentioned, the isolated polypeptide is capable of inhibiting NRG-induced cancer cell migration and/or proliferation.

According to a further specific embodiment, the isolated polypeptide inhibits NRG induced HER2-HER3 heterodimerization.

As used herein "inhibiting" refers to at least 10%, 20%, 30%, 50%, 60%, 70%, 80%, 90% or even complete blockade of the biological activity.

Cancer cell migration and proliferation can be detected using methods which are well known in the art including in vivo and in vitro methods.

Thus, NRG-induced cancer cell migration can be determined by the migration chamber method which is described in details in the Examples section which follows. NRG-induced cell proliferation can be determined by analyzing cell proliferation as well known in the art. Examples include, but are not limited to, the Alamar blue assay, BrdU incorporation assay, the MTT assay and the thymidine incorporation assay. The MTT assay is described in details in the Examples section which follows.

The cancer cell can be of any cancer which expresses HER3. The cell can be of a primary tumor or a metastatic tumor.

The cell can be a non-cultured cell, a product of primary culturing or a cell line.

According to a specific embodiment, the isolated polypeptide is capable of inducing HER3 degradation. This is of specific significance, as removal of HER3 from the cell membrane and its degradation renders it inaccessible for further signaling.

Thus, according to a specific embodiment, the isolated polypeptide induces an increase of at least 10%, 20%, 30%, 50%, 60%, 70%, 80%, 90% or even complete degradation (100%) of HER3, as compared to the level of the protein in cells of the same strain in the absence of the isolated polypeptide (control).

Methods of determining HER3 protein level are well known in the art, such as immunoprecipitation and Western blotting as described in the Examples section which follows.

Interestingly, the present inventors have found that the protein may induce faster and higher HER3 degradation than NRG. Methods of determining this feature are well known in the art and described in details in Example 3 of the Examples section which follows.

According to a specific embodiment, the isolated polypeptide is capable of inducing internalization of the HER3 receptor. This is of specific significance, as removal of HER3 from the cell membrane renders it inaccessible for further signaling.

Thus, according to a specific embodiment, the isolated polypeptide induces an increase of at least 10%, 20%, 30%, 50%, 60%, 70%, 80%, 90% or even complete (100%) internalization of HER3, as compared to the level of HER3 on the surface of the cells of the same strain in the absence of the isolated polypeptide (control).

Methods of determining HER3 cell surface protein level are well known in the art, such as immunohistochemistry, flow cytometry and radiolabeling. Specific examples of such assays are further described in the Examples section which follows. According to a specific embodiment, the isolated polypeptide is capable of inducing antibody dependent cell mediated cytotoxicity (ADCC).

The antibody-dependent cell-mediated cytotoxicity (ADCC) is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. For example, eosinophils can kill certain parasitic worms known as helminths through ADCC. ADCC is part of the adaptive immune response due to its dependence on a prior antibody response.

ADCC recruitment is an important arm for combating tumors in vivo.

This heterodimer conformation of HER3 allows the signaling complex to activate multiple pathways including the MAPK (ERK), PI3K/Akt, and PLCγ The intracellular domain of HER3 contains 6 recognition sites for the SH2 domain of the p85 subunit of PI3K. HER3 binding causes the allosteric activation of p110, the lipid kinase subunit of PI3K, a function not found in either EGFR or ErbB2.

According to a specific embodiment, the isolated polypeptide is capable of inhibiting NRG-induced HER3 phosphorylation and optionally AKT and/or ERK activation.

Methods of determining activation of signaling pathways are well known in the art and include in-vitro kinase assays and the use of antibodies directed at the phosphorylated forms of the substrates. Some of these methods are described in the Examples section which follows.

A specific embodiment, related to ERK is discussed infra. Extracellular signal-regulated kinases (ERKs) 1 and 2 (ERK1/2) are members of the mitogen-activated protein kinase (MAPK) family of cell signaling enzymes controlling cell fates such as embryogenesis, cell differentiation, cell proliferation, and cell death. ERK1/2 are activated via dual phosphorylation on specific tyrosine (Tyr$^{204}$) and threonine (Thr$^{202}$) residues by mitogen-activated or extracellular signal-regulated protein kinase (MAPK).

Methods of analyzing Erk (also referred to as MAPK) phosphorylation are well known in the art. Such are described in length in the Examples section which follows. Erk phosphorylation kits are typically based on the use of a phospho-specific ERK/MAPK (Phospho-Thr$^{202}$ and Tyr$^{204}$) primary antibody together with a labeled secondary antibody in a ready-to-use format. Such kits are available from various vendors including, but not limited to, Sigma-Aldrich, Perkin-Elmer, Cayman Chemicals and Millipore.

According to a specific embodiment, the isolated polypeptide (e.g., NG33) is (strikingly) as efficient as trastuzumab in inhibiting N87 (ATCC® CRL-5822™) proliferation, as described in the Examples section which follows. Thus the use of the same molar amounts of the isolated protein and trastuzumab (an anti HER2 antibody) result in at least as the same inhibition of tumor cell proliferation.

According to a specific embodiment, the isolated polypeptide having any and all of the aforementioned features comprises an antigen recognition domain which comprises complementarity determining region (CDR) amino acid sequences as set forth in:

SEQ ID NOs: 1 (CDR1), 2 (CDR2) and 3 (CDR3), (sequentially arranged from N to C on a light chain of said polypeptide) and 4 (CDR1), 5 (CDR2) and 6 (CDR3) (sequentially arranged from N to C on a heavy chain of said polypeptide) (Clone NG33).

According to another embodiment, the isolated polypeptide comprises an antigen recognition domain which specifically binds human HER-3, wherein said antigen recognition domain comprises complementarity determining region (CDR) amino acid sequences as set forth in:

SEQ ID NOs: 1 (CDR1), 2 (CDR2) and 3 (CDR3), (sequentially arranged from N to C on a light chain of said polypeptide) and 4 (CDR1), 5 (CDR2) and 6 (CDR3) (sequentially arranged from N to C on a heavy chain of said polypeptide) (Clone NG33);

SEQ ID NOs: 7 (CDR1), 8 (CDR2) and 9 (CDR3), (sequentially arranged from N to C on a light chain of said polypeptide) and 10 (CDR1), 11 (CDR2) and 12 (CDR3) (sequentially arranged from N to C on a heavy chain of said polypeptide) (Clone NG83); or SEQ ID NOs: 13 (CDR1), 14 (CDR2) and 15 (CDR3), (sequentially arranged from N to C on a light chain of said polypeptide) and 16 (CDR1), 17 (CDR2) and 18 (CDR3) (sequentially arranged from N to C on a heavy chain of said polypeptide) (Clone NG140).

Combinations of these proteins are also contemplated according to the present teachings, essentially, NG33+NG140, NG140+NG83, NG83+NG33 either as a single molecule (multispecific e.g., bispecific or trispecific configurations) or as monospecific antibodies.

Other combinations are further described hereinbelow.

As used herein, the terms "complementarity-determining region" or "CDR" are used interchangeably to refer to the antigen binding regions. In antibodies, the "CDRs" refer to the antigen binding region found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular polypeptide that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996), the "conformational definition" (see, e.g., Makabe et al., Journal of Biological Chemistry, 283:1156-1166, 2008) and IMGT [Lefranc M P, et al. (2003) IMGT unique numbering for immunoglobulin and T cell receptor variable domains and Ig superfamily V-like domains. Dev Comp Immunol 27: 55-77].

As used herein, the "variable regions" and "CDRs" may refer to variable regions and CDRs defined by any approach known in the art, including combinations of approaches.

According to a specific embodiment, the "variable regions" and "CDRs" refer to variable regions and CDRs defined by the IMGT approach.

It will be appreciated that the proteins of the invention comprise native proteins (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body, as long as the function is essentially retained i.e., at least 80% of the activity e.g., HER3 binding. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

According to a specific embodiment, the protein binds HER3 but does not bind HER1, HER2 or HER4, as determined by FACS.

According to a specific embodiment, the protein binds the native form of HER3, e.g., as determined by FACS (e.g., clone NG33).

According to a specific embodiment, the protein does not bind the denatured form of HER3, e.g., as determined by Western Blot analysis (clone NG33).

According to a specific embodiment, the protein binds the denatured form of HER3, e.g., as determined by Western Blot analysis and SDS-PAGE (clone NG83 as evidenced in FIG. 1E).

According to a specific embodiment, the protein binds the native and the denatured form of HER3, according to the measures described above (FACS and Western blot).

The term "antibody" as used in this invention includes intact molecules as well as functional fragments thereof, such as Fab, F(ab')2, Fv and a single chain Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

According to a specific embodiment, the antibody is a monoclonal antibody of any subtype e.g., IgG, IgM, IgA etc. According to a specific embodiment the antibody is IgG1 or IgG4.

Anti HER3 antibodies of some embodiments of the present invention can be selected from a plurality of antibodies (e.g., antibody library) and screening by testing at least one of:

(i) binding human HER-3 with a $K_D$ value of 10 nM or lower;
(ii) inhibiting neuregulin (NRG) binding to human HER3;
(iii) inhibiting NRG-induced cancer cell migration and proliferation;
(iv) inhibiting NRG induced ERK and/or AKT activation;
(v) inducing HER3 degradation faster than NRG; and
(vi) inducing HER3 internalization.

According to a specific embodiment, the antibody qualifies all (i)-(vi) qualification criteria.

Methods of analyzing these properties are described in length hereinabove and in the Examples section which follows.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

It will be appreciated that the CDR sequences described herein can be implemented in a multispecific e.g., bispecific antibody configuration.

As used herein "bispecific" or "bifunctional" antibody, refers to an artificial hybrid antibody having two different heavy/light chain pairs and two different binding sites. Bispecific antibodies can be produced by a variety of methods including fusion of hybridomas. See e.g., Songsivilai and Lachmann (1990) Clin. Exp. Immunol. 79:315-321; Kostelny et al. (1992) J. Immunol. 148:1547-1553. The bispecific antibody may bind HER3 at one epitope (e.g., NG33) and another target which is expected to cooperate with HER3 in biological processes, such as cell proliferation or Erk activation.

Thus, according to an exemplary embodiment, the bispecific antibody of the invention binds HER3 (with the CDRs of NG33 described herein) and at least one other HER family member such as EGFR, HER2 or HER4. Such antibodies are described in length in WO2012/156975. Alternatively a trispecific configuration may target three ErbB proteins in a single molecule e.g., EGFR, HER2 and HER3.

Alternatively, the bispecific antibody binds distinct epitopes on HER3 such as NG33 and NG140 or NG83.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to a specific embodiment, the protein is generated using recombinant DNA techniques. Thus there is provided a method of producing the isolated polypeptide described herein, comprising culturing a host cell expressing the polypeptide so that the polypeptide is produced.

To this end a polynucleotide encoding the protein is introduced into a nucleic acid construct suitable for recombinant expression and introduced into the host cell. Such a polynucleotide will comprise the nucleic acid sequences encoding the CDRs. Examples of such nucleic acid sequences are provided in SEQ ID NOs: 21-22, 31-32, 41-42 or 23-28, 33-38, 43-48.

A host cell comprising a nucleic acid sequence encoding the polypeptide of the invention is also contemplated herein. The host cell may be a primary cell or a cell-line. According to a specific embodiment the host cell is a hybridoma cell.

According to a specific embodiment, the protein is isolated (purified) from the culture.

According to specific embodiments, the isolated recombinant polypeptide is essentially free from contaminating cellular components such as carbohydrate, lipid or other impurities.

Methods for isolation and purification of polypeptides are well known in the art, see for example Chromatography, 5$^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science B V, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

According to specific embodiments, at least 80%, at least 90%, at least 95% or at least 99% of the total protein in the preparation is the recombinant polypeptide of interest.

According to specific embodiments, the isolated recombinant polypeptide is purified to a pharmaceutically acceptable purity.

Methods for evaluating protein purity are well known in the art and include SEC-HPLC, peptide mapping, SDS gel analysis and ELISA for specific contaminants.

The proteins (e.g., antibodies) of the invention can be used in a variety of clinical applications. By virtue of their high affinity to HER3 they can be used in diagnostic applications and in personalized treatments which require the testing of HER3 expression.

Accordingly, the protein is attached to a heterologous moiety e.g., a pharmaceutical agent.

As used herein the term "heterologous moiety" refers to a chemical substance which is non-native to the protein e.g., antibody.

As used herein a pharmaceutical agent can be a pharmaceutical agent e.g., drug (used in therapy or research) or a detectable moiety (used in diagnosis or research).

As used herein "drug" refers to a therapeutically active ingredient such as a small molecule (e.g., chemotherapy), a protein, a lipid, a carbohydrate or a combination of same.

According to a specific embodiment, the pharmaceutical agent comprises a cytotoxic agent.

According to a further specific embodiment, the cytotoxic agent is an enzymatically active toxin.

Enzymatically active toxins and fragments thereof which can be used include diphtheria A chain, nonbinding active fragments of diphtheria toxin, exotoxin A chain (from *Pseudomonas aeruginosa*); ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. Methods of conjugating the toxin are described in US 20130209495.

According to a further specific embodiment, the cytotoxic agent is a chemotherapeutic agent or a radioactive isotope.

According to a specific embodiment, the chemotherapy is a tyrosine kinase inhibitor.

As used herein the term "tyrosine kinase inhibitors (TKIs)" refers to a small molecule capable of inhibiting an ErbB signaling pathway. Typically, TKIs contemplated herein may be categorized to four groups: (1) ATP-competitive inhibitors, which bind predominantly to the ATP-binding site of the kinase when this site is in the active conformation; (2) inhibitors that recognize and bind to the non-active conformation of the ATP-binding site of the kinase, thus making activation energetically unfavorable; (3) allosteric inhibitors, that bind outside of the ATP-binding site, modifying the tridimensional structure of the receptor and disrupting the interaction between the ATP and the kinase pocket; and (4) covalent inhibitors, that bind irreversibly by covalently bonding to the ATP-binding site of the target kinase. The TKI can be specific to a specific ErbB family member or can inhibit multiple ErbB family members. The TKI can recognize wild type ErbB family member and/or a mutated ErbB family member.

Non limiting examples of TKI include erlotinib HCL (OSI-774; Tarceva®; OSI Pharma), gefitinib (Iressa®, Astra7eneca and Teva), lapatinib (Tykerb®, GlaxoSmithKline), canertinib (CI-1033, PD183805; Pfizer), PKI-166 (Novartis); PD158780; pelitinib; and AG 1478 (4-(3-Chloroanillino)-6,7-dimethoxyquinazoline), vandetanib (Zactima, ZD6474), imatinib mesylate (STI571; Gleevec), semaxinib (SU5416), vatalanib (PTK787/ZK222584), sorafenib (BAY 43-9006), sutent (SU11248), leflunomide (SU101), perlitinib (EKB-569), neratinib (HKI-272), afatinib, dacomitinib, AZD9291, rociletinib (CO-1686), HM61713 and WZ4002.

According to a specific embodiment, the TKI is pan-ErbB inhibitor, i.e., inhibiting more than one receptor in the family, such as lapatinib.

According to specific embodiments, the TKI is an irreversible TKI. Non-limiting examples of irreversible TKIs include perlitinib (EKB-569), neratinib (HKI-272), canertinib (CI-1033), vandetanib (ZD6474), afatinib and dacomitinib.

According to specific embodiments, the irreversible TKI is typically used when the cancer exhibit resistance to a reversible first generation TKI such as erlotinib, gefitinib and lapatinib.

According to specific embodiments, the TKI binds an ErbB receptor having a mutation in a kinase domain of said receptor such as but not limited to the T790M mutation in the EGFR kinase domain. Non-limiting examples of TKIs that bind and inhibit mutated ErbB receptor include WZ4002, AZD9291, rociletinib (CO-1686) and HM61713 that binds and inhibits mutated EGF-R. According to specific embodiments the TKI does not bind a wild-type ErbB receptor (e.g. EGF-R).

According to specific embodiments, the TKI is selected from the group consisting of perlitinib (EKB-569), neratinib (HKI-272), canertinib (CI-1033), vandetanib (ZD6474), afatinib, dacomitinib, AZD9291, rociletinib (CO-1686), HM61713 and WZ4002.

According to specific embodiments, the TKI is AZD9291.

Other chemotherapeutic agents which can be used in accordance with the present teachings (either as a conjugate with the protein e.g., antibody, or used together as a co-formulation or separate formulations) are listed in Table 1 below.

TABLE 1

Chemotherapeutic Agents Useful in Neoplastic Disease[1]

| Class | Type of Agent | Name | Disease[2] |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan | Multiple myeloma, breast, ovary |
| | | Chlorambucil | Chronic lymphocytic leukemia, primary macroglobulinemia, Hodgkin's disease, non-Hodgkin's lymphomas |
| | | Estramustine | Prostate |
| | Ethylenimines and Methylmelamines | Hexamethyl-melamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine Procarbazine Aziridine | Malignant melanoma, Hodgkin's disease, soft-tissue sarcomas |
| Antimetabolites | Folic Acid Analogs | Methotrexate Trimetrexate | lymphocytic leukemia, choriocarcinoma, mycosis fungoides, breast, head and neck, lung, osteogenic sarcoma |
| | Pyrimidine Analogs | Fluorouracil | Breast, colon, stomach, pancreas, |
| | | Floxuridine | ovary, head and neck, urinary bladder, premalignant skin lesions (topical) |

TABLE 1-continued

Chemotherapeutic Agents Useful in Neoplastic Disease[1]

| Class | Type of Agent | Name | Disease[2] |
|---|---|---|---|
| | Purine Analogs and Related Inhibitors | Cytarabine Azacitidine Mercaptopurine | Acute granulocytic and acute lymphocytic leukemias lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyl-Lotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| | | Doxorubicin 4'-Deoxydoxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | Asparaginase | Acute lymphocytic leukemia |
| | Taxanes | Docetaxel Paclitaxel | Breast, ovarian |
| | Biological Response Modifiers | Interferon Alfa | Hairy cell leukemia, Kaposi's sarcoma, melanoma, carcinoid, cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |

TABLE 1-continued

Chemotherapeutic Agents Useful in Neoplastic Disease[1]

| Class | Type of Agent | Name | Disease[2] |
|---|---|---|---|
| | Methyl Hydrazine Derivative | Procarbazine | Hodgkin's disease |
| | Adrenocortical Suppressant | Mitotane | Adrenal cortex |
| Hormones and Antagonists | costeroids | Aminoglutethimide | Breast Acute and chronic lymphocytic leukemias, non-Hodgkin's lymphomas, Hodgkin's disease, breast |
| | Progestins | Hydroxy-progesterone caproate Medroxy-progesterone acetate Megestrol acetate | Endometrium, breast |
| | Estrogens | Diethylstilbestrol Ethinyl estradiol | Breast, prostate |
| | Antiestrogen | Tamoxifen | |
| | Androgens | tosterone propionate Fluoxymesterone | |
| | Antiandrogen | Flutamide | Prostate |
| | Gonadotropin-Releasing hormone analog | Leuprolide Goserelin | Prostate, Estrogen-receptor-positive breast |

[1]Adapted from Calabresi, P., and B. A. Chabner, "Chemotherapy of Neoplastic Diseases" Section XII, pp 1202-1263 in: Goodman and Gilman's The Pharmacological Basis of Therapeutics, Eighth ed., 1990 Pergamin Press, Inc.; and Barrows, L. R., "Antineoplastic and Immunoactive Drugs", Chapter 75, pp 1236-1262, in: Remington: The Science and Practice of Pharmacy, Mack Publishing Co. Easton, PA, 1995.; both references are incorporated by reference herein, in particular for treatment protocols.
[2]Neoplasms are carcinomas unless otherwise indicated.

Various types of detectable or reporter moieties may be conjugated to the proteins of the invention. These include, but not are limited to, a radioactive isotope (such as $^{[125]}$ iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, U K. (2001); U.S. Pat. No. 6,350,466 to Targesome, Inc. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

An affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996.

Protein Engineering 9:203; Pearce L A. et al., 1997. Biochem Molec Biol Intl 42:1179-1188.

Functional moieties, such as fluorophores, conjugated to streptavidin are commercially available from essentially all major suppliers of immunofluorescence flow cytometry reagents (for example, Pharmingen or Becton-Dickinson).

Alternatively or additionally, the proteins can be attached (or conjugated) to non-proteinacious moieties which increase their bioavailability and half-life in the circulation.

The phrase "non-proteinaceous moiety" as used herein refers to a molecule not including peptide bonded amino acids that is attached to the above-described protein. Exemplary non-proteinaceous and preferably non-toxic moieties which may be used according to the present teachings include, but are not limited to, polyethylene glycol (PEG), Polyvinyl pyrrolidone (PVP), poly(styrene comaleic anhydride) (SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

Thus, such non-proteinaceous non-toxic moieties may also be attached to the above mentioned proteins to promote stability and possibly solubility of the molecules.

Bioconjugation of such a non-proteinaceous moiety (such as PEGylation) can confer the proteins amino acid sequence with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the protein of the present invention (e.g., HER3 binding).

Bioconjugation of the protein with PEG (i.e., PEGylation) can be effected using PEG derivatives such as N-hydroxysuccinimide (NHS) esters of PEG carboxylic acids, monomethoxyPEG2-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (mPEG) form. In general, the PEG added to the anti HER3 antibody amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-AC is made under argon by reacting a DCM solution of the PEG-OH with acryloyl chloride and triethylamine (molar ratios: OH 1: acryloyl chloride 1.5: triethylamine 2, at 0.2 gram PEG/mL DCM). Such chemical groups can be attached to linearized, 2-arm, 4-arm, or 8-arm PEG molecules. It will be appreciated that the antibodies of the invention may be produced using recombinant DNA technology (where a polynucleotide encoding the antibody of the invention is introduced into an appropriate host cell where the antibody is synthesized. Exemplary sequences are provided in SEQ ID NOs: 21-22, 31-32, 41-42 or 23-28, 33-38, 43-48.

Typically for diagnostic and research purposes the protein (e.g., antibody) is immobilized to a solid phase (e.g., ELISA plate).

When needed and in the absence of an adequate ADCC activity, it may be desirable to modify the antibody of the invention with respect to effector function, so as to enhance the effectiveness of the protein in treating cancer, for example. For example in the case of the protein being an antibody, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

The high affinity of the present protein to HER3 renders it an important tool for clinical and research applications.

Thus according to an aspect of the invention there is provided a method of determining presence of HER3 polypeptide in a cell suspected of containing the HER3 polypeptide, the method comprising contacting the cell with the isolated polypeptide as described herein (e.g., having the CDRs of NG33) under conditions which allow formation of an immunocomplex comprising the HER3 polypeptide and the isolated polypeptide, and determining presence or level of said immunocomplex, thereby determining presence of HER3 polypeptide in the cell.

Accordingly, there is also provided an immunocomplex as described above for the diagnosis of a HER3-associated medical condition. In these cases, a biological sample suspected of comprising HER3 (either in cells or in cell lysates) is provided. As used herein "a biological sample" refers to, body fluids such as whole blood, serum, plasma, cerebrospinal fluid, urine, lymph fluids, and various external secretions of the respiratory, intestinal and genitourinary tracts, tears, saliva, milk as well as white blood cells, malignant tissues, amniotic fluid and chorionic villi. Alternatively for research applications, the biological sample may comprise primary cells or cell lines which may be cancerous.

Methods of detecting presence or level of an immunocomplex are well known in the art and include, but are not limited to ELISA and immunoblotting.

The protein(s) e.g., having the CDRs of NG33, NG140 or NG83 may be packed in a kit with further instructions for using the isolated polypeptide to detect a HER3 polypeptide.

Thus, according to an aspect of the invention there is provided a method of treating a HER3 associated medical condition in a subject in need thereof, the method comprising administering to the subject a therapeutically effective amount of the isolated polypeptide, thereby treating the HER3 associated medical condition.

Alternatively, there is provided use of the isolated polypeptide in the manufacture of a medicament identified for treating a HER3 associated medical condition.

Alternatively, there is provided the isolated polypeptide in the treatment of a HER3 associated medical condition, i.e., condition that would benefit from treatment with the protein e.g., anti-ErbB3 antibody.

These include chronic and acute disorders or diseases including those pathological conditions which predispose the mammal to the disorder in question. Generally, the disorder will be one in which excessive activation of the HER2-HER3 or EGFR-HER3 protein complex is occurring.

According to a specific embodiment, the HER3 associated medical condition is a hyperproliferative disease.

According to a specific embodiment, the hyperproliferative disease is cancer.

Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer (NSCLC), gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland.

According to a specific embodiment, the cancer is selected from the group consisting of melanoma, breast cancer, ovarian cancer, renal carcinoma, gastrointestinal/colon cancer, lung cancer, clear cell sarcoma and prostate cancer.

According to specific embodiments, the cancer is an NSCLC.

According to a specific embodiment, the cancer exhibits autocrine NRG-induced signaling.

According to specific embodiments, the cancer is a tyrosine kinase inhibitor (TKI) resistant cancer.

As used herein, the phrase "resistance to a tyrosine kinase inhibitor (TKI)" refers to non-responsiveness to TKI treatment as may be manifested by tumor size, in-vitro activity assays and/or patient survival.

According to a specific embodiment, resistance refers to no amelioration in disease symptoms or progression according to a regulatory agency guidelines (e.g., FDA) for the specific TKI used. Resistance to treatment can be primary resistance or acquired resistance.

According to specific embodiments the resistance is an acquired resistance.

As used herein the term "acquired resistance" refers to progression of resistance following initial positive response to therapy.

According to specific embodiments the patient further exhibits resistance to an anti-ErbB monoclonal such as but not limited to anti-EGFR (e.g. cetuximab).

The main known molecular mechanism of acquired resistance to TKIs include mutations in the e.g. EGFR kinase domain, including T790M; gene amplification, such as MET, leading to overproduction of the TK; over-expression of RTK ligands that mediates uncontrolled tumor cells activation; modification of signaling pathways, such as PTEN instability that mediates constitutive Akt activation; and increased efflux or decreased influx of TKIs from the cancer cell, mediated by membrane transporters such as MDR1 or hOCT1 [see e.g. Chen and Fu, Acta Pharmaceutica Sinica B, (2011) 1(4): 197-207].

Thus, according to a specific embodiment, the cancer cells express an ErbB receptor having a mutation in a kinase domain of said receptor.

Methods of analyzing sequence alterations such as in the kinase domain of an ErbB are well known in the art, basically including analysis (e.g., by PCR and sequencing) of genomic DNA, or cDNA encoding the ErbB using a biological sample obtained from the subject exhibiting the resistance (e.g., biopsy). Analysis at the polypeptide level can also be done such as using antibodies which specifically recognize the mutated form of the protein and not the wild-type form. Analysis at the protein level can also be done by an activity assay.

Such biological samples include, but are not limited to, body fluids such as whole blood, serum, plasma, cerebrospinal fluid, urine, lymph fluids, and various external secretions of the respiratory, intestinal and genitourinary tracts, tears, saliva, milk as well as white blood cells, malignant tissues, amniotic fluid and chorionic villi.

According to one embodiment the sample comprises a fluid, such as for example, blood, plasma, saliva etc.

The sample may comprise cells including, but not limited to blood cells, bone marrow cells, pancreatic cells, lung cells, hepatic cells, spleen cells, kidney cells, cardiac cells, ovarian cells, breast tissue cells, skin cells (e.g., epithelial cells, fibroblasts, keratinocytes), lymph node cells.

According to a particular embodiment the cells comprise cancer cells. Such cells can be obtained using methods known in the art, including, but not limited to, fine needle biopsy, needle biopsy, core needle biopsy and surgical biopsy (e.g., lung biopsy), buccal smear and lavage.

Mutations in the kinase domain of the receptor may alter the kinase activity.

According to specific embodiments, the mutation does not substantially affect a kinase activity of said ErbB.

As used herein, the term "substantially affect" refers to an un-altered kinase activity (+/−10%, or 20%) in the presence of absence of the mutation.

Determining the kinase activity can be achieved using methods well known in the art, such as Western-blot and in-vitro kinase assay.

Non limiting examples of mutations in a kinase domain of an ErbB include the following EGFR mutations: G719C, G719S, L858R, L861Q, T790M and an exon 20 insertion; and the T798M mutation in HER2.

According to specific embodiments the mutation comprises the T790M mutation.

As used herein, the term "T790M" refers to a substitution of Threonine to Methionine at position 790 (T790M) in the EGFR kinase domain. This substitution was shown to preserve (i.e., not substantially affect) the kinase activity of the receptor.

The present teachings suggest the use of the isolated polypeptides disclosed herein in combination with other proteins targeting additional members of the ErbB family such as anti-EGFR and anti-HER2 antibodies.

According to another aspect of the present invention there is provided the isolated polypeptide of the present invention and at least one antibody specifically binding an ErbB family member selected from the group consisting of EGFR, HER2 and HER4 for use in treating a HER3 associated medical condition.

According to specific embodiments, the ErbB family member is selected from the group consisting of EGFR and HER2.

The antibody, which binds the ErbB family member, may comprise a mono-specific antibody and/or a multi-specific antibody as further disclosed hereinbelow. The at least one antibody may be to a single target or to a plurality of targets According to specific embodiments the at least one antibody comprises an anti-EGFR antibody and an anti-HER2 antibody.

According to specific embodiments, the anti-EGFR comprises cetuximab.

As used herein the term "cetuximab", trademarked as Erbitux®, refers to an immunotherapy drug that contains the active ingredient cetuximab, an anti-EGF-R monoclonal antibody According to specific embodiments, the anti-HER2 comprises Trastuzumab.

As used herein the term "Trastuzumab", trademarked as Hercelon or Herceptin®, refers to an immunotherapy drug that contains the active ingredient Trastuzumab, an anti-HER2 monoclonal antibody.

Thus, the combination may comprise, NG33, trastuzumab and cetuximab.

According to an aspect of the invention, there is provided a method of treating a subject having cancer exhibiting a resistance to a tyrosine kinase inhibitor (TKI), wherein said TKI is directed to an ErbB family member and wherein cells of the cancer express said ErbB family member, the method comprising administering to the subject a therapeutically effective amount of antibodies comprising an anti-EGFR antibody, an anti-HER2 antibody and an anti-HER3 antibody, wherein:

(i) said anti-EGFR antibody comprises cetuximab; and said anti-HER3 antibody comprises an antigen recognition domain having complementarity determining region (CDR) amino acid sequences as set forth in: SEQ ID NOs: 1 (CDR1), 2 (CDR2) and 3 (CDR3), (sequentially arranged from N to C on a light chain of said polypeptide) and 4 (CDR1), 5 (CDR2) and 6 (CDR3) (sequentially arranged from N to C on a heavy chain of said polypeptide) (Clone NG33);

(ii) said anti-HER2 antibody comprises trastuzumab; and said anti-HER3 antibody comprises an antigen recognition domain an antigen recognition domain having complementarity determining region (CDR) amino acid sequences as set forth in: SEQ ID NOs: 1 (CDR1), 2 (CDR2) and 3 (CDR3), (sequentially arranged from N to C on a light chain of said polypeptide) and 4 (CDR1), 5 (CDR2) and 6 (CDR3) (sequentially arranged from N to C on a heavy chain of said polypeptide) (Clone NG33); and/or (iii) said anti-EGFR antibody comprises cetuximab, said anti-HER2 antibody comprises trastuzumab; and said anti-HER3 antibody comprises an antigen recognition domain an antigen recognition domain having complementarity determining region (CDR) amino acid sequences as set forth in: SEQ ID NOs: 1 (CDR1), 2 (CDR2) and 3 (CDR3), (sequentially arranged from N to C on a light chain of said polypeptide) and 4 (CDR1), 5 (CDR2) and 6 (CDR3) (sequentially arranged from N to C on a heavy chain of said polypeptide) (Clone NG33), thereby treating the resistance to a tyrosine kinase inhibitor (TKI) of an ErbB family member in a subject.

As shown in the Examples section which follows the present inventors have shown that treatment with NG33, anti-EGFR and anti-HER2 antibodies in combination with low dose AZD-9291 TKI had an improved anti-tumor effect on erlotinib resistant NSCLC tumors as compared to the triple mAb therapy or to a high dose AZD-9291 therapy. Thus, the present invention further contemplates a combined treatment comprising the isolated polypeptide of the present invention, anti-EGFR and anti-HER2 antibodies and TKI.

According to specific embodiments, the TKI is the TKI which the cancer exhibits resistance to.

According to other specific embodiments, the TKI is a TKI which the cancer exhibits sensitivity to (i.e. an additional TKI which is different from the TKI which the cancer exhibits resistance to). The additional TKI can inhibit the same ErbB family member(s) or another ErbB family member(s) targeted by the TKI the cancer exhibits resistance to.

Administration can be effected concomitantly with administration of the antibodies or following administration of the antibodies.

The TKI may be administered at a gold standard dosing as a single agent, below a gold standard dosing as a single agent or above a gold standard dosing as a single agent.

According to specific embodiments, the TKI is administered below gold standard dosing as a single agent.

As used herein the term "gold standard dosing" refers to the dosing which is recommended by a regulatory agency (e.g., FDA), for a given tumor at a given stage.

According to other specific embodiments the TKI is administered at a dose that does not exert at least one side effect which is associated with the gold standard dosing. Non-limiting examples of side effects of a TKI treatment include skin rash, diarrhea, mouth sores, paronychia, fatigue, hyperglycemia, hepatotoxicity, kidney failure, cardiovascular effects, electrolytes anomalies and GI perforations.

According to an aspect of the present invention there is provided a method of treating a subject having cancer exhibiting a resistance to a tyrosine kinase inhibitor (TKI), wherein said TKI is directed to an ErbB family member and wherein cells of the cancer express said ErbB family member, the method comprising administering to the subject a therapeutically effective amount of an additional TKI, a therapeutically effective amount of the isolated polypeptide of the present invention and a therapeutically effective amount of at least one antibody specifically binding EGFR and HER2, wherein said additional TKI is different from said TKI and wherein said cancer does not exhibit resistance to said additional TKI.

The combinations of the isolated polypeptides and the antibodies and/or the TKI described herein have combined improved anti tumor activity. As used herein the phrase "combined improved anti tumor activity" refers to at least additive but also synergistically improved anti tumor activity as explained hereinabove.

The present teachings further contemplate analyzing expression of the HER3 and/or NRG in cells of said cancer, wherein an expression above a predetermined threshold is indicative that the subject may benefit from the treatment.

As used herein "a predetermined threshold" refers to an mRNA or protein expression which is higher than in cells of the same type being non-tumorigenic.

As used herein the term "subject" refers to a mammal, preferably a human subject. According to specific embodiments the subject suffers from the pathology (e.g. HER3 associated medical condition e.g. cancer). According to specific embodiments, the subject suffer from cancer exhibiting a resistance to a tyrosine kinase inhibitor (TKI), wherein said TKI is directed to an ErbB family member and wherein cells of the cancer express said ErbB family member.

As used herein the term "treating" refers to alleviating or diminishing a symptom associated with a disease (e.g., cancerous disease). Preferably, treating means cures, e.g., substantially eliminates, the symptoms associated with the disease.

The protein e.g., antibody or antibody combinations (e.g., NG33 and optionally NG140, NG83 or XC252 or antibodies to other HER members e.g., EGFR, HER2) and/or TKI of the present invention can be administered to an organism per se, or in a pharmaceutical composition where they are mixed with suitable carriers or excipients (either individually or in a co-formulation).

The antibodies may be formulated each in a different formulation, two in one formulation and the other one in a separate formulation, or all in the same formulation.

According to specific embodiments, the pharmaceutical composition further comprises as an active ingredient a TKI.

According to specific embodiments, the active ingredients are in a co-formulation.

According to other specific embodiments, the active ingredients are in separate formulations.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the protein accountable for the intended biological effect (e.g., antibody or antibody combinations (e.g., NG33 and optionally NG140, NG83 or antibodies to other HER members e.g., HER2).

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans. Since administration of the antibody combination is expected to produce improved results over the administration of single antibodies, the therapeutically effective dose of each of the antibodies in the combined treatment may be for example less than 50%, 40%, 30%, 20% or even less than 10% the of the FDA approved dose.

Since administration of the antibody and TKI combination is expected to produce improved results over the administration of TKI as a monotherapy, the therapeutically effective dose of the TKI in the combined treatment may be for example less than 50%, 40%, 30%, 20% or even less than 10% the of the FDA approved dose.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations (e.g., weekly or bi-weekly administrations) of the antibody or antibody combinations (e.g., NG33 and optionally NG140, NG83 or antibodies to other HER members e.g., HER2), with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Typically used models for analyzing the effect of the agents described herein on tumors are provided infra.

Suitable cells for use in animal models and in vitro analyses include but are not limited to:

Lung Cancer:
LKR-13, LKR-10, NSCLC, H1437, H1299, H3255, H1819, H4006, HCC827, HCC2279;

An animal lung tumor model expressing a T790M mutated EGFR is described e.g. in Regales et al. PLoS ONE (2007) 2:e810 and Politi et al. Genes Dev. (2006) 20:1496-1510.

Suitable cells for use in animal models and in vitro analyses include but are not limited to H1975, PC9ER, H820, HCC827 and H1650.

Breast
BT-474;
Head and Neck Cancer:
HN5, PCi 15B, PCI 37°, 4PCISSC 103;
Ovarian Cancer:
OvCar3, SKOV, TOV112;

Compositions of the present invention may, if desired, be presented in a pack or dispenser device, such as an FDA-approved kit, which may contain one or more unit dosage forms containing the active ingredient. According to a specific embodiment, there is provided a kit comprising the isolated polypeptide (e.g., having the CDRs of NG33 and optionally other antibodies as described herein) and optionally a pharmaceutical agent, as described herein. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

According to specific embodiments, the article of manufacture or kit further comprises antibodies to other HER members e.g. EGFR, HER2.

According to specific embodiments the article of manufacture or kit further comprises TKI.

According to specific embodiments, the antibodies (e.g., antibody or antibody combinations e.g., NG33 and optionally NG140, NG83 or antibodies to other HER members e.g., EGFR, HER2) and/or TKI of the present invention may be packaged in separate containers.

As used herein, the term "separate containers" refers to at least two containers.

The packaging material may comprise at least one, at least two or at least three containers for packaging the antibodies. According to specific embodiments the packaging material comprises at least two containers for packaging the antibodies and optionally the TKI.

It will be appreciated that the antibodies (e.g., antibody or antibody combinations e.g., NG33 and optionally NG140, NG83 or antibodies to other HER members e.g., EGFR, HER2) and/or TKI of the present invention can be provided to the individual with additional active agents to achieve an improved therapeutic effect as compared to treatment with the antibodies alone. In such therapy, measures (e.g., dosing and selection of the complementary agent) are taken to adverse side effects which may be associated with combination therapies.

Administration of such combination therapy can be simultaneous, such as in a single capsule having a fixed ratio of these active agents, or in multiple capsules for each agent.

Thus, for example, the antibodies of the present invention can be administered along with analgesics, chemotherapeutic agents (e.g., anthracyclins), radiotherapeutic agents, hormonal therapy and other treatment regimens (e.g., surgery) which are well known in the art.

According to a specific embodiment, the method comprising administering to the subject an additional polypeptide, wherein such that said polypeptide comprises the CDRs of clone NG33 and said additional polypeptide comprises the CDRs of clone NG140 or NG83.

The protein of the invention e.g., anti-HER3 Ab e.g., NG33, disclosed herein may also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); and U.S. Pat. Nos. 4,485,045 and 4,644,646. Liposomes with enhanced circulation time are disclosed in U.S. Pat. No. 6,013,566.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 267: 286-288 (1982) via a disulfide interchange reaction. A chemotherapeutic agent (such as Doxorubicin) is optionally contained within the liposome. See Gabizon et al. J. National Cancer Inst. 81(19)1484 (1989).

Alternatively or additionally, the antibody of the present invention may also be used in ADEPT by conjugating the antibody to a prodrug-activating enzyme which converts a prodrug (e.g. a peptidyl chemotherapeutic agent, see WO81/01146) to an active anti-cancer drug. See, for example, WO 88/07378 and U.S. Pat. No. 4,976,278.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Antibodies and Reagents— mAbs XC252 and XC90 were generated as described in Chen X, et al. (1996) *The Journal of biological chemistry* 271(13):7620-7629. SEQ ID NOs: 49 and 53 depict the heavy and light chain amino acid sequences of the XC252 antibody, respectively. SEQ ID NOs: 50-52 depict amino acid sequences of CDR1, CDR2 and CDR3, respectively, sequentially arranged from N to C on a heavy chain of the XC252 antibody; and SEQ ID NOs: 54-56 depict amino acid sequences of CDR1, CDR2 and CDR3, respectively, sequentially arranged from N to C on a light chain of the XC252 antibody. mAbs 9F7 and 16D3 are described in (34) (IRCM, INSERM-U896, Montpellier France). Trastuzumab was from Genentech. For western blotting, anti-HER3, anti-AKT and anti-ERK were from Santa Cruz Biotechnology; anti-pAKT and anti-pHER3 antibodies were from Cell Signaling Technology. Antibodies against pERK, was kindly provided by Rony Seger. The secondary Abs used for isotyping were purchased from SouthernBiotech. NRG labeled with the d2 dye was kindly provided by CisBio (Bagnols-sur-Cèze, France). Lumi4® Tb is a trademark of Lumiphore Inc. Unless indicated, materials were from Sigma. Cetuximab and trastuzumab were purchased from Merck and Roche, respectively. AZD-9291 and CO-1686 were obtained from Selleckchem Cat#57297 and Cat#57284, respectively.

Cell Lines—

The human pancreatic carcinoma (BxPC3), ovarian carcinoma (OVCAR-5), breast cancer (T47D, SKBR-3, MCF-7), gastric cancer (NCI-N87), head and neck cancer (CAL-27), lung cancer (A549, NCI-H1935, NCI-H322M) cells lines were from ATCC (Rockville, Md.). The NIH/3T3-R1, -R2, -R2R3, -R3, -R1R4 and BXPC3-Luc cells were provided by C. Larbouret (IRCM, INSERM-U896, MontpellierGaborit et al., 2011 Apr. 1; 286(13):11337-45). Ovarian and lung cancer cells were cultured in Roswell Park Memorial Institute (RPMI) 1640 medium. Other cells were cultured in Dulbecco's modified Eagle's medium (DMEM). Media were supplemented as recommended by ATCC, usually with 10% fetal calf serum (FCS) (Life Technologies). The H1975 (ATCC; NCI-H1975_CRL-5908) lung cancer cell line (EGFR mutations: L858R and T790M, ATCC; Rockville, Md.), PC9 and erlotinib-resistant PC9ER lung cancer cells (del746-750+T790M) (described in de Bruin, et al. *Cancer discovery* 4, 606-619 (2014); published online EpubMay (10.1158/2159-8290.CD-13-0741) were maintained in RPMI-1640 supplemented with 10% FCS (Life technology) and antibiotics. PC9ER cells resistant to AZD-9291, denoted as PC9ER-AZDR cells were generated by incubating PC9ER cells with AZD-9291 for three months. The dose, initially provided at 0.5 nM, was increased every 4 days per 1.5 fold up to 2.5 µM.

Production of IgB3—

To produce IgB3 (recombinant HER3 extracellular domain fused to a human IgG Fc domain), the cDNA sequence was picked from the already made plasmid pCDM7-IgB3 (33). IgB3 cDNA sequence was cloned into the pENTR/D-TOPO vector, before processing to recombination into the pLenti6/V5-DEST vector (Invitrogen), following the vendor recommendation. The stop codon was maintained in order to avoid the V5-Tag. HEK-293FT cells were co-transfected using Jet-PEI (Polyplus) with the pLenti6-IgB3 vector and the ViraPower™ Packaging Mix (Invitrogen). Following 3 days in culture, the supernatant containing the lentiviral particles was used to infect HEK-293 cells. A stable cell line was established out of the infected cells by further selection with Blasticidine (10 µg/ml). The HEK-293/IgB3 cells were then maintained in DMEM-1% FCS for 6 days at 32° C. The supernatant was then loaded on an Agarose-Protein G column (2 ml). Following intensive washes with PBS, the IgB3 protein was eluted from the column using 0.1 M glycine buffer (pH 2.7). The more concentrated fractions were pooled and dialysed for 24 h against PBS buffer.

Generation of Monoclonal mAbs to HER3.

Immunization of Balb/c mice with IgB3, fusion between NSO myeloma cells and splenocytes from IgB3-immunized mice, and the subsequent hybridoma subcloning was performed as previously described (33). Hybridoma supernatant screening, using ELISA, was performed on 96 well-plates coated with IgB3 (1 µg/ml) or with Panitumumab (1 µg/ml) to detect and subtract the non-specific antibodies directed to the human IgG Fc domain. The plates were blocked with PBS-1% BSA (weight/vol) and incubated for 1 h with hybridoma supernatants, followed by a second incubation for 1 h with HRP-labeled anti-mouse IgG and subsequently detected using 2,2'-azino-bis (3-ethylbenzothiazoline-6-sulfonic acid). The OD at 415 nm was then measured using an ELISA microplate reader. The second step of the screening was performed by immunoprecipitation. Anti-mouse IgG agarose beads were incubated first with 100 µl of hybridoma supernatant and subsequently with whole cell lysate from HER3-expressing T47D cells. The mAbs directed to HER3 were then isotyped using the SBA Clonotyping System/HRP kit (SouthernBiotech). Large quantities of mAbs were produced by purification from hybridoma supernatant maintained in DCCM-2 medium supplemented with 1% FCS and loading on an Agarose-protein G column.

Western Blot Analysis.

Cells were grown under specified conditions or treated as indicated. Following the cells were washed twice with cold PBS and scraped into lysis buffer [50 mM Hepes (pH 7.5), 10% glycerol, 150 mM NaCl, 1% Triton X-100, 1 mM EDTA, 1 mM EGTA, 10 mM NaF, 0.1 mM Na3VO4, and a complete protease inhibitor cocktail]. Thereafter, lysates were centrifuged at 14,000 g for 15 minutes at 4° C. The supernatant was used for subsequent procedures. Western blot analyses were conducted following protein separation using gel electrophoresis and transfer to nitrocellulose membranes. Immunoblotting was performed according to the antibody manufacturers' recommendation. Blocking was done using 5% milk in PBST (0.5% Tween20 Sigma Cat#P9416). Antibody binding to membrane blots was detected using horseradish peroxidase-secondary antibodies (Jackson ImmunoResearch Laboratories), followed by treatment with ECL Western blotting detection reagents (GE Healthcare).

Flow Cytometry.

NIH/3T3-R2R3 cells were trypsinized and washed twice in PBS-1% BSA (weight/vol). The cells were then incubated for 1 h at 4° C. with the mAbs directed to EGFR, HER2, HER3 or HER4 (10 µg/ml). After 2 washes with PBS-1% BSA, the cells were incubated for 1 h at 1° C. with the anti-mouse Ab coupled to AlexaFluor 488. The anti-HER mAb capacity to bind the indicated HER at the cell surface was correlated with the fluorescence intensity measured using the LSRII flow cytometer. For internalization assays, N87 cells were incubated for different time intervals with NG33 mAb (10 µg/ml). Following trypsination and washing in saline containing albumin (1 mg/ml), cells were incubated for 30 minutes at 4° C. in the dark with a non-competitive human anti-HER3 mAb (clone 1B4C3, BioLegend) labeled with Phycoerythrin (PE). Fluorescence intensity signals of 10,000 cells per sample were determined using the LSRII flow cytometer.

Tag-Lite® HER3 Binding Assay.

Tag-lite Plasmid coding for HER3 fused with SNAP-Tag® (CISbio bioassays) is transiently expressed into HEK 293. Cells were plated and labeled 24 hours after transfection with the Tag-lite SNAP-Lumi4™-Tb (donor—CISbio bioassays). Antibodies (100 µl at 1 to 2 mg/ml) were labeled with d2 dye (acceptor). A set of sixteen two-fold serial dilutions spanning from 0.006 nM of labeled Ab (Ab-d2) were prepared from a 200 nM stock solution in Tag-lite labeling medium. The highest final concentration in the wells (50 nM) corresponded to the stock solution. The specific signal was obtained by mixing cells (10,000 HEK293-HER3-SNAP-Lumi4™-Tb cells in 10 µl/well), 5 µL Ab-d2 from the serial dilution and 5 µL Tag-lite labeling medium. The non-specific signal was obtained by mixing 10 µL of cells with 5 µL of corresponding unlabeled antibody (300 nM) and 5 µL Ab-d2 conjugate from the serial dilution. Eventually, the blank was performed by mixing 10 µl of cells with 10 µl of Taglite Buffer. All the different conditions were performed in triplicate. After overnight incubation (20° C.) Time resolved Fluorescence was measured on Pherastar FS Flash lamp and E665/E620 Ratio was computed. The Ratio E665/E620 values were plotted against antibody concentration to generate the binding curve on GraphPad Prism.

Antibody-Dependent Cellular Cytotoxicity (ADCC) Assay.

ADCC was evaluated with a luciferase-activity assay. Using 96-well white plates, BXPC3-luc (4,000 cells/well) were pre-incubated for 30 min with the indicated antibodies. Ficoll-purified human peripheral blood mononuclear cells (PBMCs) from buffy coat were then added at a 10:1 effector to target cell ratio (E:T). Following 24 h of incubation at 37° C., the supernatant was removed and luciferine (Promega, WI) added on the cells. Bioluminescence was determined using the Wallac Trilux 1450 Microbeta liquid scintillation and luminescence counter (Perkin-Elmer, MA). Percentage of cellular cytotoxicity was calculated using the following formula: percentage of specific lysis=[bioluminescence in experimental point−basal bioluminescence]/[bioluminescence in total lysis−basal bioluminescence]×100. Basal bioluminescence was obtained when Bxpc3-Luc cells were incubated with hPBMC alone and bioluminescence in total lysis was obtained following a 30 min incubation of BXPC3-Luc with SDS (0.1%).

Competition Assays.

Agent labeling was performed by Cisbio. NG33 and XC252 were labeled with Lumi4® Tb cryptate (K2) and NRG with the d2 dye. Antibody competition assays were performed in 96-well black plate coated with IgB3 (1.5 µg/ml). Following blocking with PBS-1% BSA (w/v), plates were incubated for 1 h with various concentrations of competing agents under gentle shaking at RT. The labeled mAb, NG33-K2 or XC252-K2, was then added at 1 nM final concentration. Following 1 h incubation, the plate was washed 4 times with KREBS buffer (146 mM NaCl, 4 mM KCl, 0.5 mM $MgCl_2$, 1 mM $CaCl_2$, 10 mM Hepes, 1 gr/L glucose, and 1 mg/mL albumin), and the fluorescent intensity (excitation: 488 nm, emission: 610 nm) was measured using a fluorescence microplate reader. NRG competition assay was performed with NIH/3T3-R2R3 cells plated in 96-well black plate (50,000 cells per well) and incubated for 24 h in full medium. Following overnight serum starvation, the cells were washed with 100 µl of KREBS buffer and incubated with increasing concentrations of competitors for 45 min at 4° C. Following addition of NRG-d2 (10 nM), the cells were incubated for 45 additional minutes at 4° C. Finally, following two washes with KREBS buffer, the fluorescence intensity was measured at 670 nm (excitation: 620 nm).

Cell Proliferation Assays.

Cell proliferation and survival was assessed using the 3-(4,5-dimethylthiazol-2-yl)-2,5 diphenyl tetrazolium bromide (MTT) assay (Sigma Cat#M2003). Cells were plated on 96-well plates (2,000-5,000 cells/well) in triplicates. After one day, the cells were treated with various treatments in fresh medium or starvation medium supplemented with NRG (between 10 pg/ml to 100 ng/ml). After 3-4 days, the MTT reagent was added to the cells, and 1 h later the formazan crystals were dissolved in SDS-DMF solution for 30 minutes. Absorbance was measured using a microplate reader, Biorad Model 680, at 570 nm.

Migration Assays.

OVCAR-5 cells ($1 \times 10^6$ cells/well) were seeded in the upper compartment of migration chambers (Transwell, Corning). The lower compartment was filled with medium supplemented with NRG (10 ng/ml) in the absence or presence of mAb NG33 (10 µg/ml). Following 24 hours, cells that reached the lower side of the filter were fixed, permeabilized with Triton X-100 (0.1%), and stained with GIEMSA solution. Images were quantified by using ImageJ.

Tumorigenic Growth in Mice.

All animal studies were approved by the Weizmann Institute's Review Board (IRB). Tumor bearing CD1/nude mice were randomized in groups of five-ten mice and injected subcutaneously in the right flank with cancer cells ($3-5 \times 10^6$ per mouse depending on the cell line). mAbs were injected intraperitoneally at a total dose of 200 µg per mouse per injection, twice a week, for 5 weeks or until tumors reached the size of 1,500 $mm^3$. In experiments evaluating the effect of the TKI AZD-9291, Vehicle (Vehicle formulation: HPMC 0.5% (sigma Cat#56340), Tween80 0.1% (Sigma Cat #P8074 in water), Erlotinib at a dose of 50 mg/kg per injection, or AZD9291 at a dose of 1 or 5 mg/kg per injection were injected daily intraperitoneally. In one experiment (FIG. 16), mice were treated daily with Erlotinib at a dose of 50 mg/kg per injection until tumors reached a size of 800 $mm^3$ and only then were treated as indicated. Tumor volume and body weight were evaluated twice and once per week, respectively. Mice were euthanized when tumor size reached 1,500 $mm^3$. Few of the tumors were harvested from mice at the indicated time points and taken for further evaluation. Survival of the tumor bearing mice was recorded and depicted by Kaplan-Meier analysis.

Data and Statistical Analysis—

FACS data were represented using the FlowJo software. The other data were represented using the Prism GraphPad software and statistical analysis was performed using this same software.

Example 1

Generation of Monoclonal Antibodies Against the Extracellular Domain of HER3

In order generate novel antibodies to HER3 (33), a HEK-293 cell derivative stably secreting a fusion protein combining the HER3 extracellular domain and the Fc domain of a human IgG1 (IgB3; FIG. 1A) was generated. IgB3 was purified from conditioned media using protein A chromatography and its purity was confirmed by gel electrophoresis. Mice were immunized repeatedly with IgB3 and were then used for hybridoma generation. To select hybridomas producing antibodies directed to HER3 and to differentiate them from those producing antibodies directed to the Fc domain, hybridoma supernatants were screened by ELISA on IgB3-coated microplates and negative selection was performed on human IgG-coated microplate (FIG. 1B). Hybridomas secreting antibodies able to recognize both IgB3 and IgG molecules were considered as Fc domain specific, hence excluded. The hybridoma supernatants presenting antibodies able to bind specifically with IgB3 were checked further for their capacity to bind with the native form of HER3 by an immunoprecipitation assay (FIG. 1C), and the corresponding positive hybridomas were then subcloned. Twelve positive antibodies were selected. Partial nucleotide sequencing of cDNAs encoding the heavy chain and the light chain of the antibodies identified four distinct groups of antibodies. These antibodies were isotyped and identified as IgG1 molecules with kappa chains (FIG. 1D). The subsequent studies employed six mAbs: 4 from the new generation and 2 from the previous generation (33). In order to find an antibody useful to perform primary immunodetection of HER3 during a western-blot experiment, the different antibodies directed to HER3 were screened. As shown in FIG. 1E, NG83 was found as the best reagent for western blotting, able to recognize the denatured form of HER3.

Example 2

The Generated Monoclonal Antibodies to IgB3 Recognize Specifically and with High Affinity the Native Form of HER3

The comparison of the capacity of purified mAbs to bind with IgB3 was evaluated using ELISA (FIG. 2A). The EC50 of the mAb for IgB3-binding (using microplate precoated with 50 µl of IgB3; 1 µg/ml) ranged between 0.21 nM (XC252) to 16.8 nM (NG140). Next, the ability of the antibodies to bind to the native form of the receptor using FACS and NIH/3T3-R2R3 cells which co-overexpress ectopic HER2 and HER3 (34) was compared (FIGS. 2B and 2C). Here the affinities differed from one antibody to another. To define the affinity of each antibody for HER3 the Tag Lite® technology (FIGS. 3A-E) was used. Each antibody was labeled with the d2-dye, and by measuring the binding of the labeled-mAb to cells presenting Lumi4(Tb)-labeled HER3 using FRET, the $K_D$ was determined and reported in Table 2, below. The values obtained correlate with the different patterns of HER3 binding determined by FACS (FIGS. 2B and 2C), although they are distinct from the patterns of IgB3 binding determined using ELISA (FIG. 2A). As expected, it was impossible to determine the affinity of mAb NG533, because its ability to bind with the native form of HER3 is barely detectable using either FACS (FIGS. 2B and 2C) or immunoprecipitation (FIG. 2D). The specificity of the antibodies to HER3 and not to the other members of the EGFR family was shown using FACS comparison of their ability to bind with engineered NIH/3T3-HER cells presenting either EGFR alone, HER2 alone, HER3 alone or EGFR and HER4 (FIGS. 4A-B).

TABLE 2

Kd determination of indicated mAb to HER3 using the Tag-Lite technology. Cells were transfected with HER3-SNAP-Tag and labeled withBG-Lumi4(Tb), a SNAP-tag subtract. Following incubation with increasing concentrations of indicated d2 labeled mAb directed to HER3, the Kd was determined from the binding curve fitting. The binding curve was obtained by measuring the FRET between the donor Lumi4(Tb) and the acceptor d2-dye.

| mAbs | $K_D$ (nM) | S.D. (nM) |
|---|---|---|
| NG33 | 2.96 | 0.66 |
| NG83 | >14 | — |
| NG140 | 6.12 | — |
| NG533 | un. | — |
| XC90 | 2.30 | 0.02 |
| XC252 | 1.09 | 0.17 | un. = undetermined.

Example 3

Specific Monoclonal Antibodies Trigger HER3 Degradation, Internalization and Cell-Mediated Cytotoxicity The capacity of the mAbs to decrease abundance of HER3 was determined using western blotting. Gastric cancer N87 cells were treated for 3 h with each mAb (10 µg/ml) and HER3 expression levels were analyzed using western blotting (FIG. 5A). The results and their quantification are shown in FIG. 5B. NG33 induced a strong HER3 degradation, similar to the one obtained using another HER3 specific mAb, 16D3, which was previously reported (34) (data not shown). XC90 and XC252 mAbs also caused HER3 degradation, but their impact was weaker. As shown, NG533 is able to bind IgB3 with a good affinity but it presents a slight affinity for the native form of HER3 (as noticed by the FACS experiment or immunoprecipitation). Considering its minor binding to HER3, which is enough to provoke ADCC, it is suggested that this mAb may be a strong inducer of ADCC.

Next, cell dependence effect on HER3 degradation was determined by testing additional different cancer cell lines. Similar patterns of receptor degradation were observed in the other cell lines (FIGS. 5C and 6). As with N87 cells, the strongest HER3 degradation signal was obtained using NG33 mAb. Next, the pattern of HER3 degradation using NG33 (10 µg/ml) was compared to the signal obtained using NRG (20 ng/ml) (FIGS. 7A-B). Interestingly, NG33 induced faster and higher HER3 degradation than NRG. In addition, flow cytometry analysis demonstrated that treatment of N87 cells with NG33 (10 µg/ml) induced HER3 receptor internalization (FIGS. 8A-B). Furthermore, the mAb ability to lead to Antibody-Dependant Cell-mediated Cytotoxicity (ADCC) was determined using BxPC3-luc cells incubated with the studied mAb and thereafter with human PBMC. Cell killing was detected by measuring luminescence after addition of luciferine, and shown in FIG. 5D. Trastuzumab was used as a positive control of ADCC. Three mAbs, NG33, NG83 and NG533 strongly or moderately induced ADCC.

Example 4

NG33, an Anti-HER3 mAbs, Competes with NRG for Binding to HER3 and Inhibits NRG-Induced Migration and Proliferation of Cancer Cells A competition assay between mAbs to HER3 and d2-labeled NRG was used to find out which of the mAbs was able to reduce NRG binding to HER3 (FIG. 9A). NIH/3T3-R2R3 cells overexpressing an ectopic HER3 were treated for 45 min at 4° C. with increasing concentrations of each mAb, under conditions that allow mAb binding but avoid HER3 internalization and degradation. Thereafter, the cells were incubated for 30 min at 4° C. with d2-labeled NRG. Fluorescence intensity measured after several washes correlated with the level of D2-labelled NRG. Unlabelled-NRG was used as a positive control of competition. NG33 was able to compete with NRG binding. Presumably, NG33 directly displaces NRG from the ligand binding site or binding of the mAb modifies HER3's conformation in a way that does not allow NRG binding. Antibodies NG83 and NG140, like the irrelevant IgG, did not disturb NRG binding, while NG140 slightly competed with NRG, and XC90 and XC252 slightly enhanced NRG binding. To check if the effect of the mAb on NRG binding impacts the phosphorylation of HER3 and subsequently the downstream phosphorylation of AKT and ERK, N87 cells were treated with each mAb for 20 min, followed by a short stimulation with NRG (20 ng/ml; FIG. 9B). It appears that NG33 can completely prevent NRG-induced HER3 phosphorylation and subsequent AKT and ERK activation. Similarly, XC252 was able to partly decrease the phosphorylation level of HER3, but this was not mediated by direct competition with NRG.

Next, the impact of NG33 on ligand-induced cell proliferation and migration was studied. First, the effect of NG33 on NRG-induced migration of ovarian cancer cells was evaluated (FIG. 9C). The results confirmed that NG33 treatment can avoid NRG-induced migration. Likewise, NG33 ability to decrease survival of different cancer cells was evaluated in vitro using the MTT assay (FIGS. 10A and 10C). Cells were first selected for their ability to proliferate following NRG stimulation (data not shown). In several cancer cell lines (breast: MCF7 and SKBR-3, lung: NCI-H322M, ovarian: OVCAR-5, pancreatic: BxPC3 and gastric: N87), NG33 inhibited NRG-induced cell survival, between 20% to 50%. Antibodies NG83, XC252, and XC90 were tested as well. XC252 significantly inhibited NRG-induced cell survival only in the pancreatic PxPC3 cells with no marked inhibition on any other cell line tested. XC90 exerted no marked decrease on cell survival hardly reaching 30% inhibition in MCF-7 cells (data not shown). Similarly NG83 did not impact survival at all, but this might be explained by its low affinity (10-fold weaker than the other mAbs) (Table 2, above).

Example 5

NG33 is as Efficient as Trastuzumab in Inhibiting N87 Cell Proliferation In Vitro and in Animals In order to examine the ability of NG33 to decrease cancer cell growth, N87, a gastric cancer cell line overexpressing HER2 and coexpressing EGFR and HER3 was used. The comparison of the geometric mean taken from the FACS experiment showed that N87 cells express 2.2-fold more HER2 than HER3 (FIG. 10B). Hence, two different ways to decrease N87 cell growth were compared, by disturbing HER2-HER3 activated pathways: one approach used mAb NG33 to HER3 and the other used trastuzumab, a clinical approved therapeutic mAb directed against HER2 (Herceptin™) The effects of the antibodies were compared both in vitro, using a MTT assay on NRG-stimulated N87 cells, and in vivo on N87 cell xenografts (FIGS. 10C, 10D and 11). The in vitro comparison was extended to additional cell lines (FIG. 10A). The results obtained indicated that NG33 is as efficient as Trastuzumab in decreasing cell survival in vitro and N87 tumor growth in vivo ($p<0.05$).

Example 6

Improvement of the In Vitro Effects of NG33 by Combinations with Another mAb Directed to HER3

Combinations of antibodies directed against two different epitopes of the same receptor, as has been previously shown, can improve the effect of treatment with a single mAb (28, 29). To try and improve the effects of NG33, it was combined with another anti-HER3 mAb targeting a distinct epitope of the receptor. First, it was determined which antibody from the anti-HER3 series targets an epitope distinct from that targeted by NG33. For this, a Lumi4(Tb)-labeled NG33 and IgB3-coated microplates were used (FIG. 12A). The results indicated that XC90 was the only mAb able to compete with NG33. The NG140 and XC252 mAbs did not alter NG33 binding, in line with the result obtained using an irrelevant mouse IgG. Interestingly, mAb NG83 potentiated NG33 binding to IgB3. To corroborate these observations a Lumi4(Tb)-labeled XC252 (FIG. 12B), as well as labeled forms of NG83 or NG140 (data not shown) were used. In order to test the selected anti-HER3 mAb combinations for their efficacy in vitro, their abilities to degrade HER3 (FIG. 12C) and to decrease phosphorylation of HER3, AKT and ERK (FIG. 12D) were examined in NRG-stimulated cells. The study of HER3 degradation following 2 h mAb treatment identified NG33+NG83 and NG33+NG140 as candidate combinations. However, the analysis of NRG-induced phosphorylation of HER3, ERK and particularly, of AKT following 20 min mAb combinations treatment, identified NG33+XC252 and NG33+NG140 as candidates.

To further evaluate the effect of the selected anti-HER3 mAb combinations for their efficacy in vitro, the effect of the NG33+NG140 combination was determined using a MTT assay on NRG-stimulated N87 cells (FIG. 13). The results obtained indicated that the NG33+NG140 combination significantly enhances the inhibitory effect of the NG33 single mAb treatment on N87 cell survival.

Example 7

The Combination of Two Anti-HER3 mAbs is not Systematically More Efficient than a Single mAb Targeting the NRG Binding Site of Hers in Decreasing Tumor Growth in Animals To determine if the combination of NG33 mAb with another anti-HER3 mAb is more efficient than using NG33 alone, the combination of two mAbs, NG33 and XC252, was tested on several tumor cell lines, which were grafted subcutaneously (gastric: N87, lung: A549, pancreatic: BxPC3, ovarian: OVCAR-5, and head and neck: CAL-27, FIG. 14). This pilot was performed with 3 mice per group. Mice were injected twice a week with the mAb combination or with PBS. The best responder of these in vivo models for solid tumor growth was the BxPC3 xenograft model. Hence, the efficacy of 3 different mAb combinations was evaluated on BxPC3 xenografts. This experiment was performed on 7 to 8 mice per group. The mice were treated every 3 days with PBS, each mAb alone or a mAb combination, for 5 weeks (0.2 mg/injection). Tumor growth curves are shown in FIGS. 15A-F. The ability of NG33 to decrease tumor growth, compared to PBS, was confirmed ($p<0.0001$, after 3 weeks of treatment). The other mAbs, NG83, NG140 and XC252, showed no statistically significant ability to decrease tumor growth by themselves. However, the combination of NG83 (FIG. 15A) or NG140 (FIG. 15B) with NG33 showed a clear trend toward an improvement of NG33's anti-tumor efficacy. The combination of NG33 with XC252 (FIG. 15C) was clearly as efficient as NG33 alone. In order to reinforce the in vivo data, the cytotoxicity of each mAb alone or in combination with NG33 was tested on BxPC3 cells in culture (FIGS. 15D, 15E and 15F). Decreasing concentrations of mAb were used and a MTT assay was performed following 3 days of treatment. NG83 and NG140 used alone did not interfere with cell proliferation. However at high concentration, NG83 or NG140 used in combination with NG33 showed a better efficacy to decrease BxPC3 proliferation than NG33 alone (FIGS. 15D and 15E). NG33 alone induced 38% inhibition of cell survival, but the use of NG33 combination with NG83 or NG140 induced 73% or 60% inhibition, respectively. This result is highly significant ($p<0.0001$) and correlate with the data obtained in animals (FIGS. 15A and 15B). On the contrary, XC252 used alone has a strong cytotoxic impact on BxPC3 proliferation leading to 60% inhibition of cell survival at high concentration. Nevertheless, the combination of NG33 and XC252 did not show any synergistic or additive impact to decrease cell survival (FIG. 15F).

Example 8

Combined Treatment with Cetuximab, Trastuzumab and Anti-HER3 Synergistically Affect Tumor Growth In-Vivo The effect of combined antibody treatment on in-vivo tumor growth was tested using the triple mAbs combination composed of the commercial antibodies cetuximab (anti-EGFR), trastuzumab (anti-HER2) and the anti-HER3 mAb 33 and was evaluated in a tumor-bearing mouse model. To this end, PC9ER NSCLC cells ($4\times10^6$) were subcutaneously inoculated into CD1-nu/nu mice. Eleven days following inoculation, mice were treated once every three days with cetuximab, trastuzumab and anti-HER3 mAb 33 as well as with all possible combinations of the three. The results presented in FIG. 20 demonstrate that combined treatment consisting of two antibodies had an increased effect on tumor growth inhibition as compared to each of the antibodies alone. Furthermore, the triple mAbs combination exerted strong and lasting inhibitory effects on tumor growth, almost completely abolishing tumor growth.

Second and third generation TKIs are being developed (Liao et al. Current Opinion Oncology, 2015); for example, the commercially available AZD-9291, CO-1686, and HM-61713 inhibit both EGFR activating and resistance mutations, while sparing wild-type EGFR. To compare the effect of such third-generation TKI to the triple antibody combination, CD1-nu/nu mice were subcutaneously inoculated with H1975 NSCLC cells ($3\times10^6$) and treated with the irreversible TKI AZD-9291 or the triple mAbs combination cetuximab, trastuzumab and the anti-HER3 mAb 33. The results presented in FIGS. 21A-B, demonstrate that the two treatments, although utilizing very different mechanisms of action, comparably inhibited growth of the erlotinib-resistant human NSCLC. Importantly, AZD-9291 slightly inhibited body weight gain compared with the triple mAb combination (FIG. 21C), which might suggests higher toxicity in animals.

In the next step, a combination of the triple mixture of mAbs (cetuximab+Trastuzumab+mAb33) and AZD9291 was evaluated in CD1-nu/nu mice subcutaneously inoculated with H1975 NSCLC cells ($3\times10^6$). As shown in FIG. 22, the combination of the triple mAb and a low dose AZD-9291 had an improved anti-tumor effect as compared to the triple mAb therapy or to a high dose AZD-9291 therapy. These results raise the possibility of combining the two treatment modalities (i.e. triple mAb therapy and TKI) using sub-dosing of the TKI in order to limit adverse effects.

Example 9

NSCLC Develop Resistance to AZD-9291 Therapy while Maintaining Sensitivity to Combined Treatment with Cetuximab, Trastuzumab and Anti-HER3

To evaluate the effect of the triple antibody combination therapy on cells resistant to third-generation TKI, PC9ER NSCLC cells were incubated with AZD-9291 for three months. The surviving cells, denoted herein as PC9ER-AZDR, lost sensitivity to AZD-9291, as evaluated by MTT assay (FIG. 23); and their EGFR remained phosphorylated when exposed to both AZD-9291 and another third generation TKI, CO-1686 (FIG. 24).

On the contrary, the colorimetric MTT assay indicated that treatment with cetuximab, trastuzumab and antiHER3 mAB33 most potently inhibited survival of both PC9ER cells and PC9ER-AZDR cells (FIG. 23).

Taken together, these results indicate that the third-generation TKIs might evoke new resistance mechanisms but the offered treatment using three mAbs can overcome emergence of this resistance.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. Barros F F, Powe D G, Ellis I O, & Green A R (2010) Understanding the HER family in breast cancer: interaction with ligands, dimerization and treatments. *Histopathology* 56(5):560-572.
2. Lax I, et al. (1988) Localization of a major receptor-binding domain for epidermal growth factor by affinity labeling. *Molecular and cellular biology* 8(4):1831-1834.
3. Burgess A W (2008) EGFR family: structure physiology signalling and therapeutic targets. *Growth factors* 26(5): 263-274.
4. Clayton A H, et al. (2005) Ligand-induced dimer-tetramer transition during the activation of the cell surface epidermal growth factor receptor-A multidimensional microscopy analysis. *The Journal of biological chemistry* 280 (34):30392-30399.
5. Garrett T P, et al. (2002) Crystal structure of a truncated epidermal growth factor receptor extracellular domain bound to transforming growth factor alpha. *Cell* 110(6): 763-773.
6. Yarden Y & Sliwkowski M X (2001) Untangling the ErbB signalling network. *Nature reviews. Molecular cell biology* 2(2): 127-137.
7. Kozer N, et al. (2013) Exploring higher-order EGFR oligomerisation and phosphorylation—a combined experimental and theoretical approach. *Molecular bioSystems* 9(7):1849-1863.
8. Walker F, et al. (2012) Ligand binding induces a conformational change in epidermal growth factor receptor dimers. *Growth factors* 30(6):394-409.
9. Shi F, Telesco S E, Liu Y, Radhakrishnan R, & Lemmon M A (2010) ErbB3/HER3 intracellular domain is competent to bind ATP and catalyze autophosphorylation. *Proceedings of the National Academy of Sciences of the United States of America* 107(17):7692-7697.
10. Berger M B, Mendrola J M, & Lemmon M A (2004) ErbB3/HER3 does not homodimerize upon neuregulin binding at the cell surface. *FEBS letters* 569(1-3):332-336.
11. Jaiswal B S, et al. (2013) Oncogenic ERBB3 mutations in human cancers. *Cancer cell* 23(5):603-617.
12. Lurje G & Lenz H J (2009) EGFR signaling and drug discovery. *Oncology* 77(6):400-410.
13. Schmitz K R & Ferguson K M (2009) Interaction of antibodies with ErbB receptor extracellular regions. *Experimental cell research* 315(4):659-670.
14. Narayan M, et al. (2009) Trastuzumab-induced HER reprogramming in "resistant" breast carcinoma cells. *Cancer research* 69(6):2191-2194.
15. Lu Y, et al. (2007) Epidermal growth factor receptor (EGFR) ubiquitination as a mechanism of acquired resis- 16. Wheeler D L, et al. (2008) Mechanisms of acquired resistance to cetuximab: role of HER (ErbB) family members. *Oncogene* 27(28):3944-3956.
17. Desbois-Mouthon C, et al. (2009) Insulin-like growth factor-1 receptor inhibition induces a resistance mechanism via the epidermal growth factor receptor/HER3/AKT signaling pathway: rational basis for cotargeting insulin-like growth factor-1 receptor and epidermal growth factor receptor in hepatocellular carcinoma. *Clinical cancer research: an official journal of the American Association for Cancer Research* 15(17):5445-5456.
18. Kruser T J & Wheeler D L (2010) Mechanisms of resistance to HER family targeting antibodies. *Experimental cell research* 316(7): 1083-1100.
19. Aurisicchio L, Marra E, Roscilli G, Mancini R, & Ciliberto G (2012) The promise of anti-ErbB3 monoclonals as new cancer therapeutics. *Oncotarget* 3(8):744-758.
20. Schoeberl B, et al. (2009) Therapeutically targeting ErbB3: a key node in ligand-induced activation of the ErbB receptor-PI3K axis. *Science signaling* 2(77):ra31.
21. Li C, et al. (2013) Human epidermal growth factor receptor 3 (HER3) blockade with U3-1287/AMG888 enhances the efficacy of radiation therapy in lung and head and neck carcinoma. *Discovery medicine* 16(87):79-92.
22. Hoffmann-LaRoche (2011) Clinical trial; protocols IDs: BP27771; 2011-002698-53; NCT01482377.
23. McDonagh C F, et al. (2012) Antitumor activity of a novel bispecific antibody that targets the ErbB2/ErbB3 oncogenic unit and inhibits heregulin-induced activation of ErbB3. *Molecular cancer therapeutics* 11(3):582-593.
24. Huang S, et al. (2013) Dual targeting of EGFR and HER3 with MEHD7945A overcomes acquired resistance to EGFR inhibitors and radiation. *Cancer research* 73(2): 824-833.
25. Schaefer G, et al. (2011) A two-in-one antibody against HER3 and EGFR has superior inhibitory activity compared with monospecific antibodies. *Cancer cell* 20(4): 472-486.
26. Fitzgerald J B, et al. (2014) MM-141, an IGF-IR- and ErbB3-directed bispecific antibody, overcomes network adaptations that limit activity of IGF-IR inhibitors. *Molecular cancer therapeutics* 13(2):410-425.
27. Ben-Kasus T, Schechter B, Sela M, & Yarden Y (2007) Cancer therapeutic antibodies come of age: targeting minimal residual disease. *Molecular oncology* 1(1):42-54.
28. Ferraro D A, et al. (2013) Inhibition of triple-negative breast cancer models by combinations of antibodies to EGFR. *Proceedings of the National Academy of Sciences of the United States of America* 110(5): 1815-1820.
29. Ben-Kasus T, Schechter B, Lavi S, Yarden Y, & Sela M (2009) Persistent elimination of ErbB-2/HER2-overexpressing tumors using combinations of monoclonal antibodies: relevance of receptor endocytosis. *Proceedings of the National Academy of Sciences of the United States of America* 106(9):3294-3299.
30. Friedman L M, et al. (2005) Synergistic down-regulation of receptor tyrosine kinases by combinations of mAbs: implications for cancer immunotherapy. *Proceedings of the National Academy of Sciences of the United States of America* 102(6): 1915-1920.
31. Miles D, et al. (2013) Treatment of older patients with HER2-positive metastatic breast cancer with pertuzumab, trastuzumab, and docetaxel: subgroup analyses from a randomized, double-blind, placebo-controlled phase III trial (CLEOPATRA). *Breast cancer research and treatment* 142(1):89-99.
32. Gala K & Chandarlapaty S (2014) Molecular Pathways: HER3 Targeted Therapy. *Clinical cancer research: an official journal of the American Association for Cancer Research* 20(6):1410-1416.
33. Chen X, et al. (1996) An immunological approach reveals biological differences between the two NDF/heregulin receptors, ErbB-3 and ErbB-4. *The Journal of biological chemistry* 271(13):7620-7629.
34. Lazrek Y, et al. (2013) Anti-HER3 domain 1 and 3 antibodies reduce tumor growth by hindering HER2/HER3 dimerization and AKT-induced MDM2, XIAP, and FoxO1 phosphorylation. *Neoplasia* 15(3): 335-347.
35. Baselga J & Swain S M (2009) Novel anticancer targets: revisiting ERBB2 and discovering ERBB3. *Nature reviews. Cancer* 9(7):463-475.
36. Jiang N, Saba N F, & Chen Z G (2012) Advances in Targeting HER3 as an Anticancer Therapy. *Chemotherapy research and practice* 2012:817304.
37. Kol A, et al. (2014) HER3, serious partner in crime: Therapeutic approaches and potential biomarkers for effect of HER3-targeting. *Pharmacology & therapeutics*.
39. Warren C M & Landgraf R (2006) Signaling through ERBB receptors: multiple layers of diversity and control. *Cellular signalling* 18(7):923-933.
40. Sak M M, et al. (2012) The oncoprotein ErbB3 is endocytosed in the absence of added ligand in a clathrin-dependent manner. *Carcinogenesis* 33(5):1031-1039.
41. Warren C M, Kani K, & Landgraf R (2006) The N-terminal domains of neuregulin 1 confer signal attenuation. *The Journal of biological chemistry* 281(37): 27306-27316.
42. Cao Z, Wu X, Yen L, Sweeney C, & Carraway K L, 3rd (2007) Neuregulin-induced ErbB3 downregulation is mediated by a protein stability cascade involving the E3 ubiquitin ligase Nrdp1. *Molecular and cellular biology* 27(6):2180-2188.
43. Huang Z, et al. (2014) The E3 ubiquitin ligase NEDD4 negatively regulates HER3/ErbB3 level and signaling. *Oncogene*.
44. Alaoui-Jamali M A, et al. (2003) Regulation of multiple tumor microenvironment markers by overexpression of single or paired combinations of ErbB receptors. *Cancer research* 63(13):3764-3774.
45. Andrique L, et al. (2012) ErbB3 (80 kDa), a nuclear variant of the ErbB3 receptor, binds to the Cyclin D1 promoter to activate cell proliferation but is negatively controlled by p14ARF. *Cellular signalling* 24(5): 1074-1085.

What is claimed is:

1. An isolated antibody comprising an antigen recognition domain specifically binding human HER-3 with a $K_D$ value of 10 nM or lower, wherein said antigen recognition domain comprises complementarity determining region (CDR) amino acid sequences as set forth in SEQ ID NOs: 1 (CDR1), 2 (CDR2) and 3 (CDR3), being sequentially arranged from N to C on a light chain of said antibody; and 4 (CDR1), 5 (CDR2) and 6 (CDR3) being sequentially arranged from N to C on a heavy chain of said antibody) (Clone NG33), wherein said antibody inhibits neuregulin (NRG) binding to said human HER3 and NRG-induced cancer cell migration and proliferation.

2. The isolated antibody of claim 1, wherein said antibody is attached to a heterologous moiety.

3. The isolated antibody of claim 2, wherein said heterologous moiety is a pharmaceutical agent.

4. The isolated antibody of claim 3, wherein said pharmaceutical agent comprises a cytotoxic agent.

5. A kit comprising the isolated antibody of claim 1 and instructions for using the isolated antibody to detect a HER3 polypeptide.

6. A kit comprising the isolated antibody of claim 1 and a pharmaceutical agent.

7. A method of determining presence of HER3 polypeptide in a cell suspected of containing the HER3 polypeptide, the method comprising contacting the cell with the isolated antibody of claim 1 under conditions which allow formation of an immunocomplex comprising the HER3 polypeptide and the isolated antibody, and determining presence of said immunocomplex, thereby determining presence of HER3 polypeptide in the cell.

8. A method of treating a HER3 associated cancer in a subject in need thereof, the method comprising administering to the subject a therapeutically effective amount of the isolated antibody of claim 1, thereby treating the HER3 associated cancer.

9. The method of claim 8, further comprising analyzing expression of said HER3 and/or NRG in cells of said cancer.

10. The method of claim 8 wherein said cancer is selected from the group consisting of ovarian cancer, breast cancer, lung cancer, pancreatic cancer and gastric cancer.

11. The method of claim 8, wherein said cancer is gastric cancer.

* * * * *